(12) United States Patent
Yang et al.

(10) Patent No.: US 10,188,754 B2
(45) Date of Patent: Jan. 29, 2019

(54) COMPOSITIONS AND METHODS FOR CHEMICAL EXCHANGE SATURATION TRANSFER (CEST) BASED MAGNETIC RESONANCE IMAGING (MRI)

(71) Applicant: THE JOHNS HOPKINS UNIVERSITY, Baltimore, MD (US)

(72) Inventors: Xing Yang, Baltimore, MD (US); Xiaolei Song, Baltimore, MD (US); Sangeeta Ray, Ellicott City, MD (US); Martin G. Pomper, Baltimore, MD (US); Michael T. McMahon, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 255 days.

(21) Appl. No.: 14/891,531

(22) PCT Filed: May 16, 2014

(86) PCT No.: PCT/US2014/038444
§ 371 (c)(1),
(2) Date: Nov. 16, 2015

(87) PCT Pub. No.: WO2014/186737
PCT Pub. Date: Nov. 20, 2014

(65) Prior Publication Data
US 2016/0082132 A1   Mar. 24, 2016

Related U.S. Application Data

(60) Provisional application No. 61/942,754, filed on Feb. 21, 2014, provisional application No. 61/824,185, filed on May 16, 2013.

(51) Int. Cl.
| | | |
|---|---|---|
| A61K 49/10 | (2006.01) |
| G01R 33/56 | (2006.01) |
| A61B 5/05 | (2006.01) |
| A61B 6/03 | (2006.01) |
| A61B 5/055 | (2006.01) |
| A61B 5/00 | (2006.01) |
| A61B 6/00 | (2006.01) |

(52) U.S. Cl.
CPC ............. *A61K 49/10* (2013.01); *A61B 5/055* (2013.01); *A61B 5/4842* (2013.01); *A61B 6/037* (2013.01); *A61B 6/481* (2013.01); *G01R 33/5601* (2013.01); *G01R 33/5605* (2013.01)

(58) Field of Classification Search
CPC ...... A61K 49/10; A61B 5/055; A61B 5/4842; A61B 6/481; A61B 6/037; G01R 33/5601; G01R 33/5605
See application file for complete search history.

(56) References Cited

U.S. PATENT DOCUMENTS

| | | | |
|---|---|---|---|
| 2,135,474 A | * | 11/1938 | Parsons .............. A61K 49/0433 424/9.45 |
| 3,940,422 A | | 2/1976 | Harita et al. |
| 5,137,797 A | | 8/1992 | Nakamura |
| 2006/0275215 A1 | | 12/2006 | Hiscock et al. |
| 2010/0135913 A1 | | 6/2010 | Aime et al. |
| 2012/0315233 A1 | | 12/2012 | Schmaus et al. |

FOREIGN PATENT DOCUMENTS

| | | |
|---|---|---|
| WO | 2010071865 A1 | 6/2010 |
| WO | 2012082874 A2 | 6/2012 |

OTHER PUBLICATIONS

International Search Report and Written Opinion dated Sep. 16, 2014, from related PCT Patent Application No. PCT/US14/38444.

* cited by examiner

*Primary Examiner* — Michael G. Hartley
*Assistant Examiner* — Leah H Schlientz
(74) *Attorney, Agent, or Firm* — Casimir Jones, S.C.; Jeffrey W. Childers

(57) ABSTRACT

Compositions and methods for chemical exchange saturation transfer (CEST) based magnetic resonance imaging (MRI) or frequency labeled exchange (FLEX) imaging are disclosed. Beta-hydroxycarboxylate and beta-aminocarboxylate derivatives including salicylic acid, salicylates, salicylic acid prodrugs, N-alkyl/aryl/acyl/sulfonyl-anthranilic acid analogs, and any aromatic compound with OH/NH group ortho to the carboxylic acid group are disclosed. Such compounds can be used as general MRI organic contrast agents and produce significantly improved contrast in MR images detectable through CEST or FLEX.

13 Claims, 38 Drawing Sheets

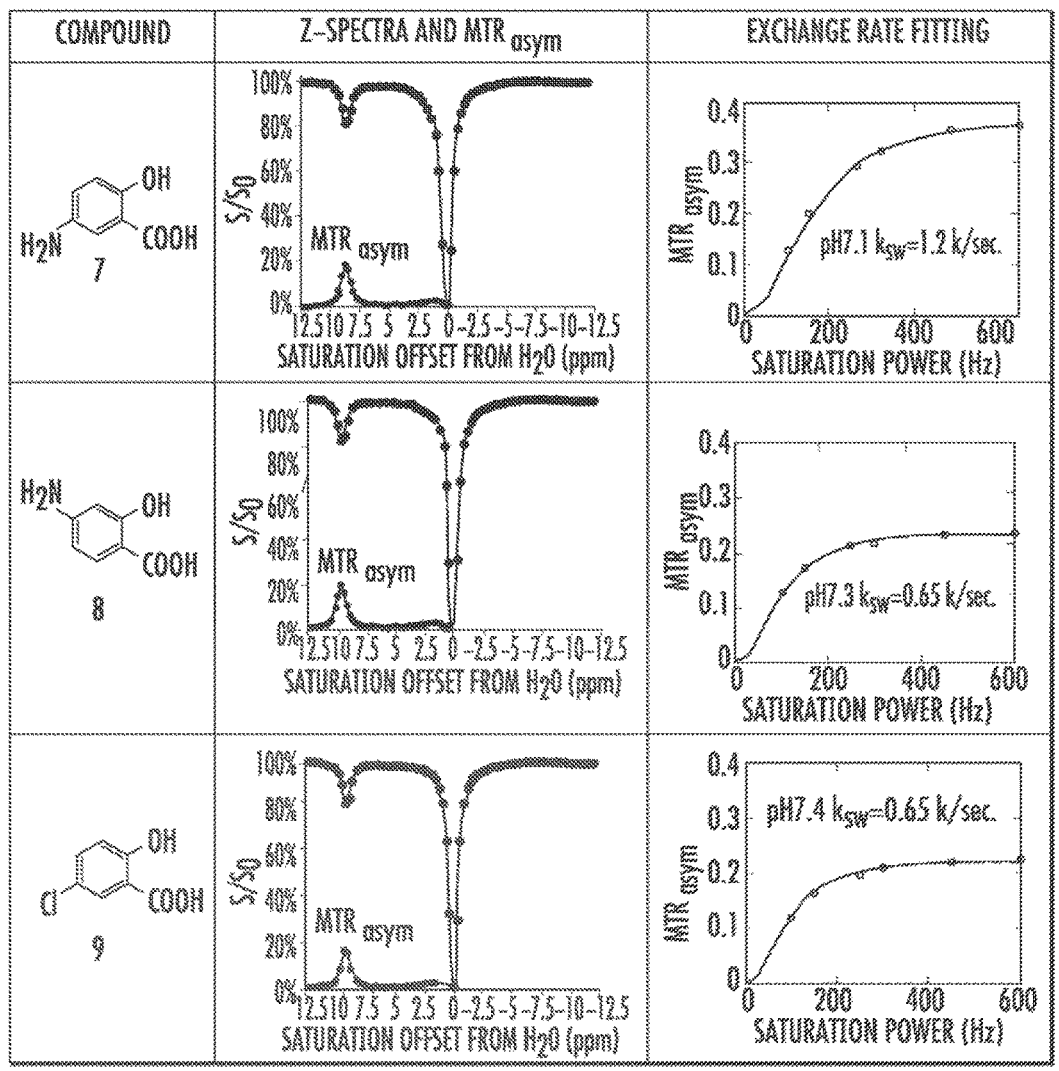
FIG. 3B (CON'T)

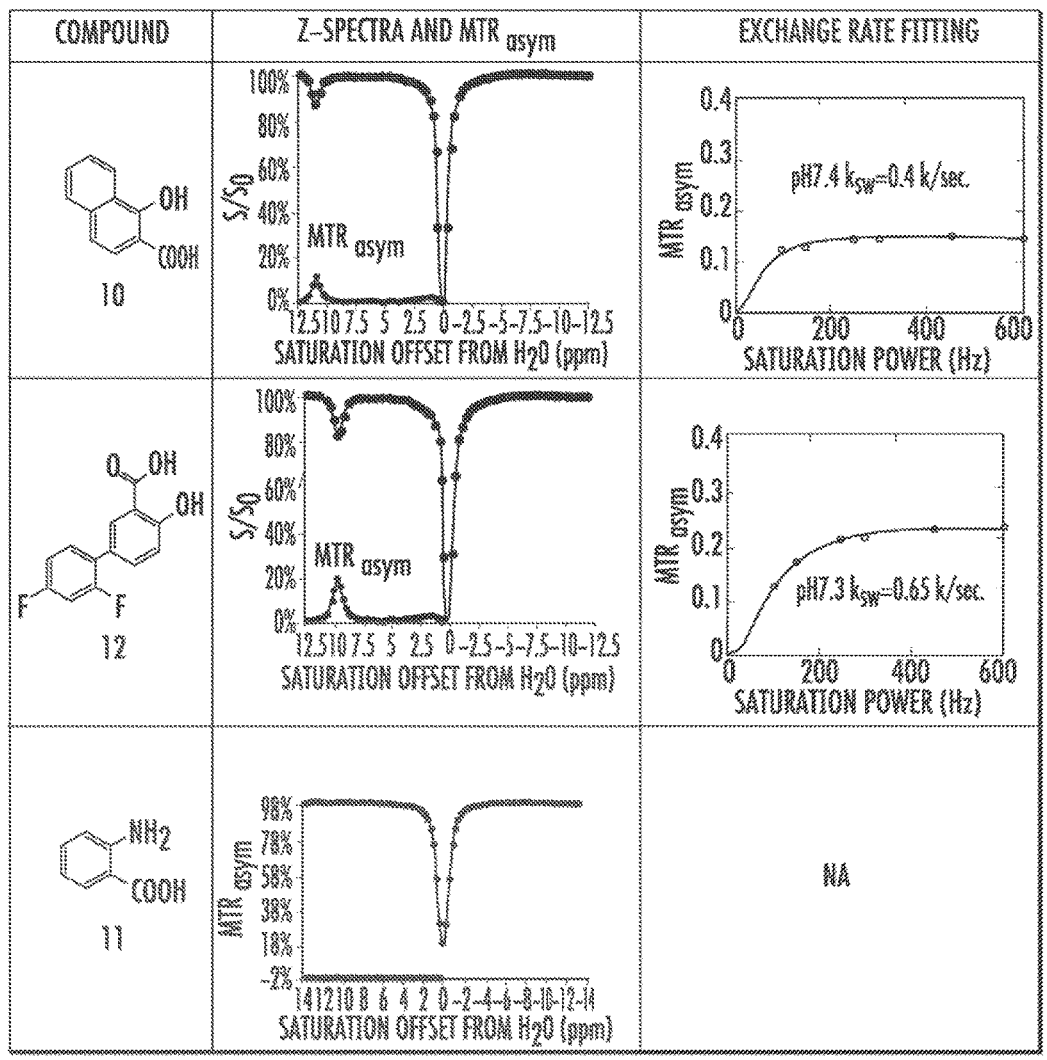
FIG. 3B (CON'T)

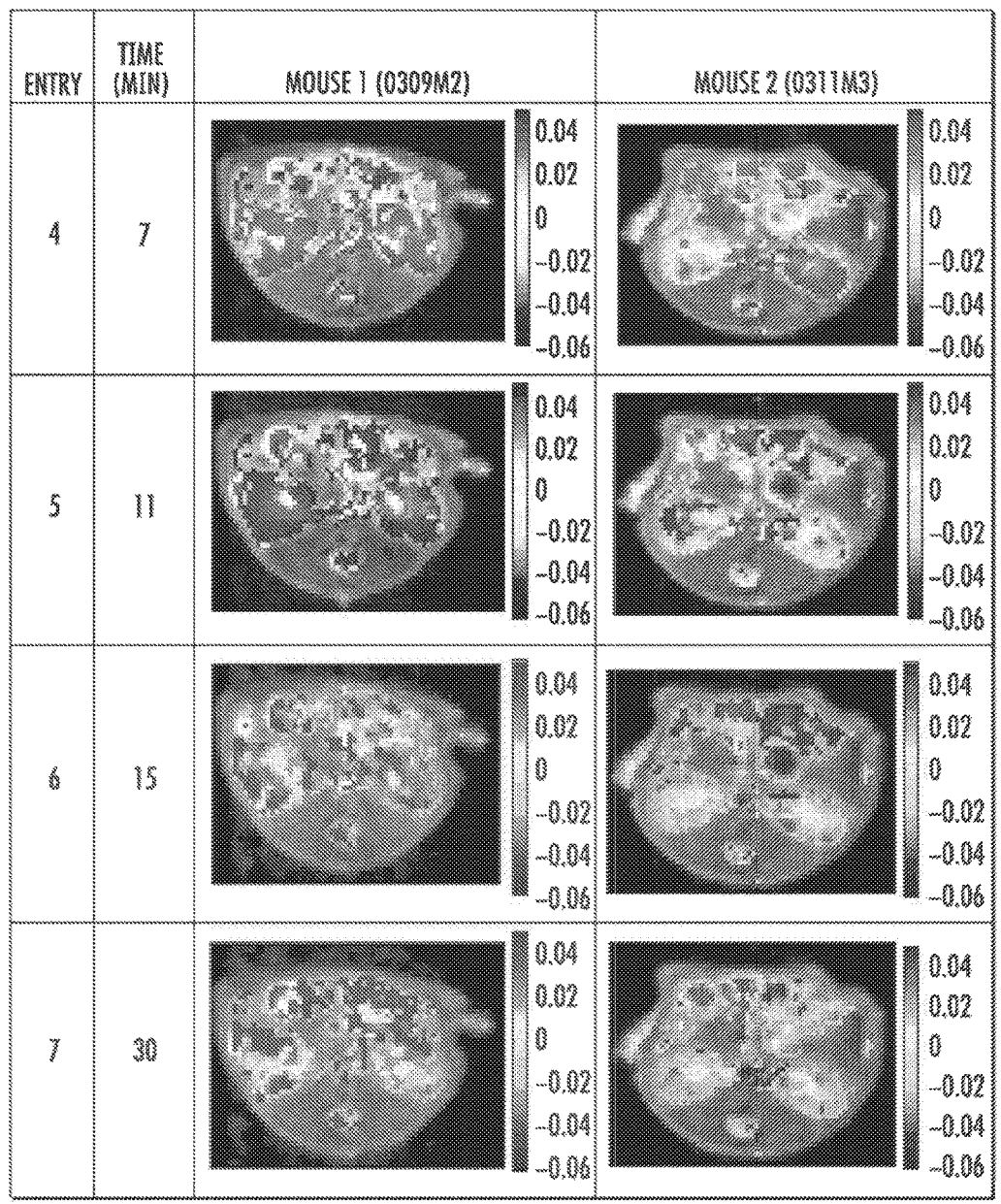
FIG. 4H (CON'T)

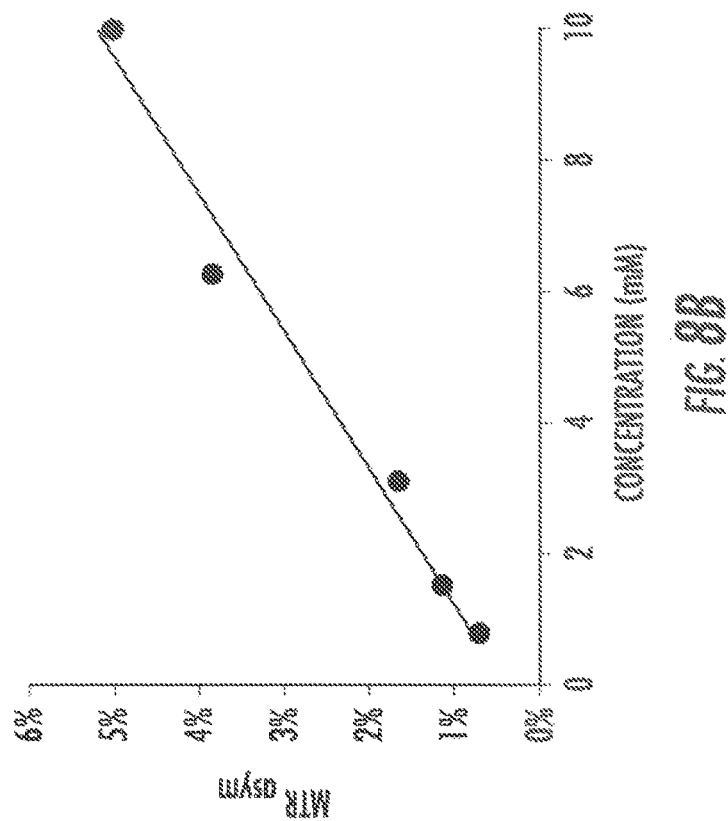
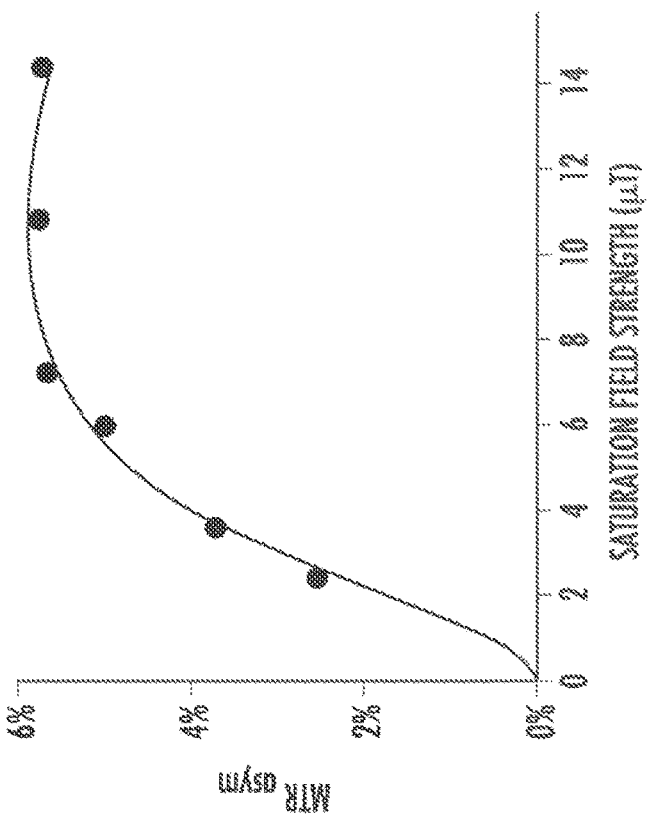
FIG. 8B
FIG. 8A

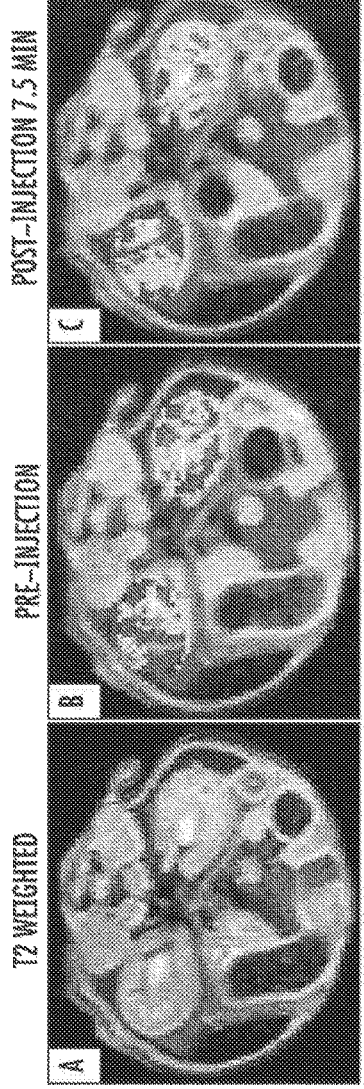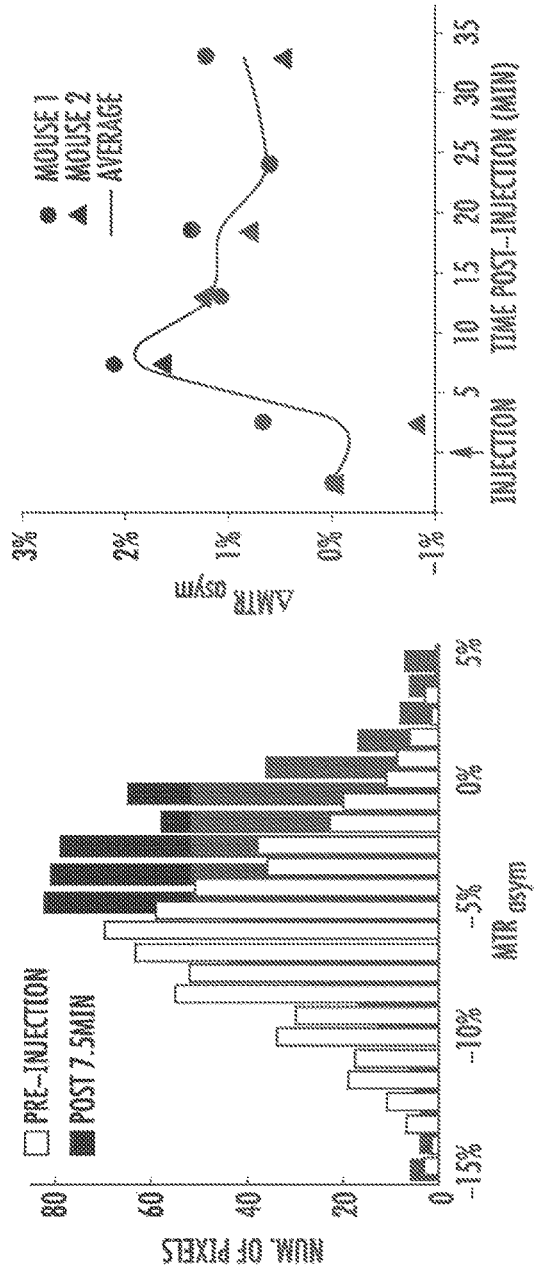
FIG. 10A  T2 WEIGHTED
FIG. 10B  PRE-INJECTION
FIG. 10C  POST-INJECTION 7.5 MIN
FIG. 10D
FIG. 10E

| entry | pH | QUESP fitting[1] | Exchange rate (k/sec.) |
|---|---|---|---|
| 1 | 5.8 |  | 9.7 |
| 2 | 6.2 |  | 4.2 |
| 3 | 6.5 |  | 2.4 |

| entry | pH | QUESP fitting[1] | Exchange rate (k/sec.) |
|---|---|---|---|
| 4 | 7.0 |  | 1.2 |
| 5 | 7.4 |  | 0.6 |
| 6 | 7.8 |  | 0.4 |

| Structure | Z-spectrum | $k_{sw}$ ($k \cdot s^{-1}$) | pH | Conc. (mM) |
|---|---|---|---|---|
| 2 | | -- | 7.4 | 25 |
| 3 | | -- | 7.4 | 25 |
| 4 | | 2.0 | 7.4 | 15 |
| Flufenamic acid (5) | | 1.0 | 7.4 | 10 |

*FIG. 24*

| Structure | Z-spectrum | $k_{sw}$ ($k \cdot s^{-1}$) | pH | Conc. (mM) |
|---|---|---|---|---|
| Meclofenamic acid (6) | | -- | 7.5 | 5 |
| Mefenamic acid (7) | | -- | 8 | 5 |
| Tolfenamic acid (8) | | -- | 7.5 | 5 |
| Niflumic acid (9) | | -- | 7.3 | 10 |

*FIG. 24 (Cont.)*

| Structure | Z-spectrum | $k_{sw}$ (kHz) | pH | Conc. (mM) |
|---|---|---|---|---|
| 10 | | -- | 7.4 | 25 |
| 11 | | 0.3 | 7.4 | 25 |
| 12 | | 0.6 | 7.1 | 25 |
| 13 | | 1.0 | 7.2 | 25 |

*FIG. 25*

| Structure | Z-spectrum | $k_{sw}$ (kHz) | pH | Conc. (mM) |
|---|---|---|---|---|
| 14 | | 0.5 | 7.2 | 25 |
| 15 | | 0.6 | 7.3 | 25 |
| 16 | | 0.5 | 7.6 | 25 |
| 17 | | -- | 7.1 | 25 |

*FIG. 25 (Cont.)*

COMPOSITIONS AND METHODS FOR CHEMICAL EXCHANGE SATURATION TRANSFER (CEST) BASED MAGNETIC RESONANCE IMAGING (MRI)

REFERENCE TO RELATED APPLICATIONS

This application is a 35 U.S.C. § 371 National Stage Entry of International Application No. PCT/US14/38444 having an international filing date of May 16, 2014, which claims the benefit of U.S. Provisional Application No. 61/824,185, filed May 16, 2013, and U.S. Provisional Application No. 61/942,754, filed Feb. 21, 2014, the content of each of the aforementioned applications is herein incorporated by reference in its entirety.

FEDERALLY SPONSORED RESEARCH OR DEVELOPMENT

This invention was made with government support under grant numbers EB015031, CA134675, and CA148901, awarded by the National Institutes of Health (NIH). The government has certain rights in the invention.

BACKGROUND

To study proteins and enzymes in their natural context in living organisms, a noninvasive imaging technique with high spatial and temporal resolution is required. Such resolution can be achieved using magnetic resonance imaging (MRI), which has been used extensively in the last two decades for anatomical, functional, and dynamic imaging. The imaging probes for magnetic resonance imaging (MRI) are termed "contrast agents," since they enhance the water proton-based contrast between the imaging target and the surrounding tissue. Detection with MRI relies on contrast in the MRI signal between the tissue of interest and its surrounding tissue, which can be further enhanced by expression of certain exogenous proteins that increase MRI contrast.

Recently, a new type of MRI contrast that relies on direct chemical exchange of protons with bulk water has been developed, and is referred to as chemical exchange saturation transfer (CEST) MRI. CEST MRI is a technique in which low-concentration marker molecules are labeled by either saturating or labeling their exchangeable protons spins by radio-frequency (RF) irradiation. If such saturation or labeling can be achieved rapidly (i.e., before the spin exchanges), exchange of such labeled spins with water leads to transfer of the magnetization, allowing indirect detection of the solute via the water resonance through a change in signal intensity in MRI.

A variety of organic molecules possessing protons that exchange rapidly with the surrounding water protons have been suggested as new contrast agents. These exchangeable protons can be "magnetically tagged" using a radiofrequency saturation pulse applied at their resonance frequency. The tagged protons exchange with the protons of surrounding water molecules and consequently reduce the MRI signal. This in and of itself would not be visible at the low concentrations of solute, but the exchanged protons are replaced with fresh, unsaturated protons and the same saturation process is repeated. Over time (e.g., several seconds) this repetition results in signal amplification, and very low concentrations of agents can be detected. Hence, these agents are termed CEST contrast agents.

Each CEST contrast agent can have a different saturation frequency, which depends on the chemical shift of the exchangeable spin. The magnitude of proton transfer enhancement (PTE) due to this effect, and the resulting signal reduction from equilibrium ($S_0$) to saturated ($S_{sat}$), are given by:

$$PTE = \frac{NM_w \alpha k_{ex}}{(1-x_{CA})R_{1wat} + x_{CA}k_{ex}} \cdot \{1 - e^{-[(1-x_{CA})R_{1wat}+x_{CA}k_{ex}]t_{sat}}\}, \quad [\text{Eq. 1}]$$

$$\text{and } (1 - S_{sat}/S_0) = \frac{PTE \cdot [CA]}{2 \cdot [H_2O]}. \quad [\text{Eq. 2}]$$

"CA" is the contrast agent containing multiple exchangeable protons, $x_{CA}$ its fractional exchangeable proton concentration, $\alpha$ the saturation efficiency, k the pseudo first-order rate constant, N the number of exchangeable protons per molecular weight unit, and $M_w$ the molecular weight of the CA. The exponential term describes the effect of back exchange and water longitudinal relaxation ($R_{1wat}=1/T_{1wat}$) on the transfer during the RF saturation period ($t_{sat}$). This effect will be bigger when spins exchange faster, but the catch is that saturation must occur faster as well, which increases the radio-frequency power needed. In addition, the resonance of the particular spins must be well separated from the bulk in the NMR spectrum, which requires a slow exchange on the NMR time scale. This condition means that the frequency difference of the exchangeable spins with the bulk is much larger than the exchange rate ($\Delta\omega$>k).

Thus, the CEST technology becomes more applicable at higher magnetic fields or when using paramagnetic shift agents. Any molecule that exhibits a significant PTE effect can be classified as a CEST (contrast) agent. The concept of these agents as MR contrast agents is somewhat similar to the chemical amplification of colorimetric labels in in situ gene expression assays. For instance, CEST agents can be detected by monitoring the water intensity as a function of the saturation frequency, leading to a so-called Z-spectrum. In such spectra, the saturation effect of the contrast agent on the water resonance is displayed as a function of irradiation frequency.

Since the first report of CEST contrast in 2000, CEST MR imaging has become a widely used MRI contrast mechanism, and CEST contrast is generated by the dynamic exchange process between an exchangeable proton of a biomarker of interest and the surrounding water protons. To detect the biomarkers, the magnetization of some of their exchangeable protons is nullified by applying a selective radiofrequency saturation pulse at the specific resonance frequency (chemical shift) of the target protons. Due to exchange of the "saturated" agent protons with surrounding water protons, the net water signal is reduced, thus enhancing the MRI contrast.

Molecular MRI is an attractive technique for many applications because it can track metabolite dynamics in vivo with better spatial resolution and anatomical co-registration than traditional techniques. While CEST MRI has been employed for many applications in molecular and cellular MRI, there remains an urgent need for the design and development of MRI contrast agents that offer improved sensitivity and contrast effects in producing MR images.

SUMMARY

The presently disclosed subject matter, in some aspects, provides compositions and methods for improving the sensitivity and contrast effects of MRI.

In one aspect, the presently disclosed subject matter provides a method of producing a magnetic resonance (MR) image of a target, comprising:

introducing a magnetic resonance imaging (MRI) contrast agent to the target; and imaging the target using a Chemical Exchange Saturation Transfer (CEST) or frequency labeled exchange (FLEX) based MRI technique to produce the MR image of the target, wherein the MRI contrast agent is a compound of Formula (I), or a salt or stereoisomer thereof:

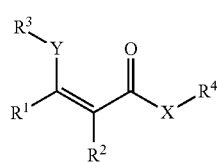

(I)

wherein:

$R^1$ and $R^2$ are each independently H, SR, phosphorus, alkyl, amino, alkoxyl, cycloalkyl, arylalkyl, cycloalkyl-alkyl, heterocyclic, heteroaryl-alkyl, aryl, heteroaryl, —C(O)-alkyl, or —C(O)O-alkyl; or $R^1$, and $R^2$, taken together with the bonds they are attached to, form an aryl or heteroaryl group; wherein said amino, alkyl, alkoxyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted;

when Y is O, $R^3$ is H, and when Y is $NR^5$, $R^3$ is selected from the group consisting of H, phosphorus, alkyl, —S(O)$_2$R, cycloalkyl, arylalkyl, cycloalkyl-alkyl, heterocyclic, heteroaryl-alkyl, aryl, heteroaryl, —C(O)-alkyl, or —C(O)O-alkyl, wherein said alkyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted, provided that at least one of $R^3$ and $R^5$ is H;

$R^4$ is H, phosphorus, halogen, SR, hydroxyl, amino, alkoxyl, alkyl, cycloalkyl, arylalkyl, cycloalkyl-alkyl, heterocyclic, heteroaryl-alkyl, aryl, heteroaryl, —C(O)— alkyl, or —C(O)O-alkyl, wherein said alkyl, amino, alkoxyl, cycloalkyl, arylalkyl, cycloalkyl-alkyl, heterocyclic, heteroaryl-alkyl, aryl, heteroaryl, —C(O)-alkyl, —C(O)O— alkyl moiety is optionally substituted; and X is O, $NR^5$, alkyl, or S;

Y is O or $NR^5$; and wherein each $R^5$ is independently selected from the group consisting of H, alkyl, cycloalkyl, arylalkyl, cycloalkyl-alkyl, heterocyclic, heteroaryl-alkyl, aryl, heteroaryl, —C(O)-alkyl, or —C(O)O-alkyl, wherein said alkyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted.

In particular aspects, the target is selected from the group consisting of a cell, a biological tissue, an organ, a tumor, a ligand, a biomarker, a therapeutically active agent, a metal ion, a chemotherapeutic, an antigen, a nanoparticle, a receptor, and a cation.

In yet more particular aspects, the method further comprises measuring a chemical shift change of exchangeable protons in said MRI contrast agent. In some aspects, the target is imaged using CEST MRI. In other aspects, the target is imaged using FLEX MRI.

In further aspects, the method further comprises diagnosing, based on the MR image of the target, a disease or disorder in a subject.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
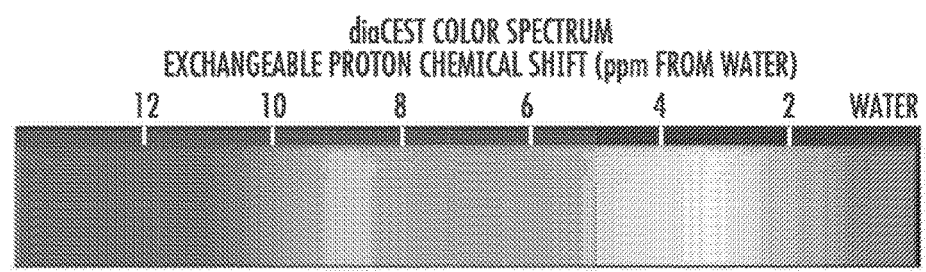
Figure 1B:
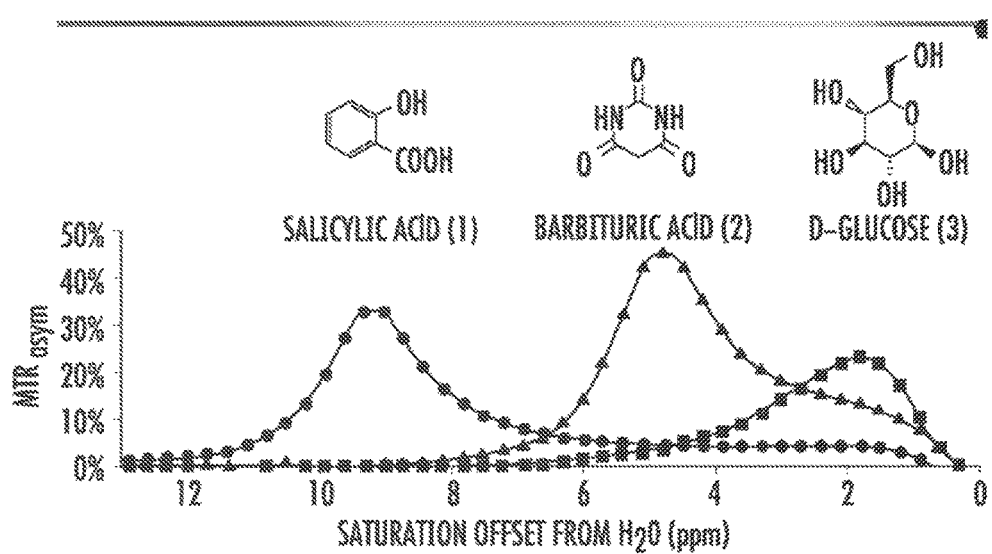
Figure 2A:
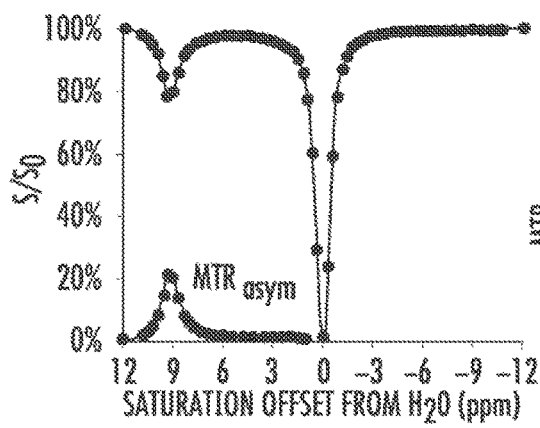

Having thus described the presently disclosed subject matter in general terms, reference will now be made to the accompanying Figures, which are not necessarily drawn to scale, and wherein:

FIGS. 1A and 1B show a proton shift spectrum and a graph, respectively, that illustrate the color spectrum for diaCEST agents according to an exemplary embodiment of the presently disclosed subject matter. FIG. 1A shows the range of exchangeable proton shifts observed presently for diaCEST agents. FIG. 1B shows CEST contrast curves for three representative agents: Salicylic Acid (1), Barbituric Acid (2), and D-Glucose (3) at concentrations of 25 mM, pH 7.0, 37° C. using ω1=7.2 μT, tsat=3 s for saturation;

FIGS. 2A-2H show four line graphs, a contrast map, a H-NMR spectra, Z-spectra graphs, and a table, respectively, that illustrate CEST properties of compound 1 according to an exemplary embodiment of the presently disclosed subject matter. FIG. 2A shows a Z-spectrum and $MTR_{asym}$ for 25 mM at pH 7.0 using ω1=3.6 μT.

Figure 2B:
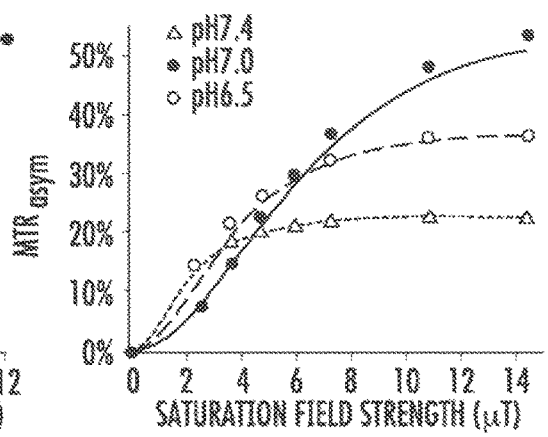
Figure 2C:
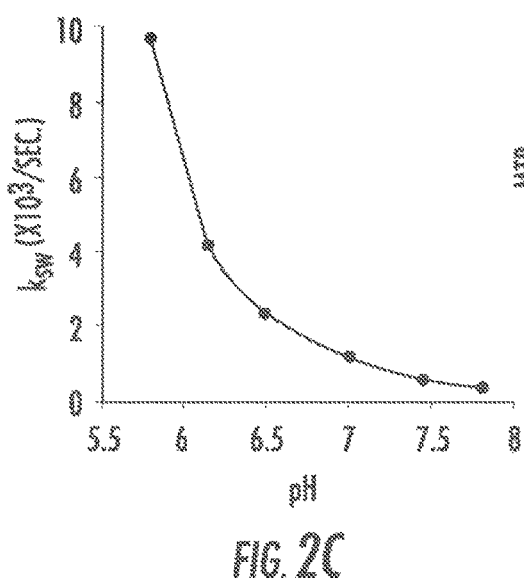
Figure 2D:
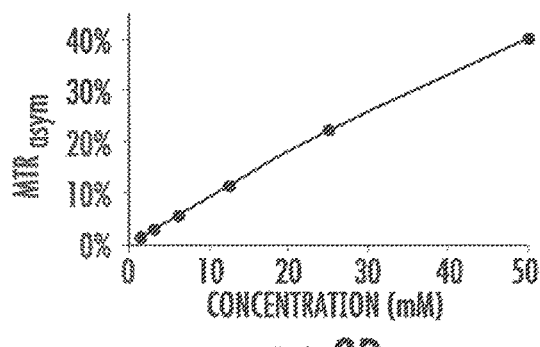
Figure 2E:
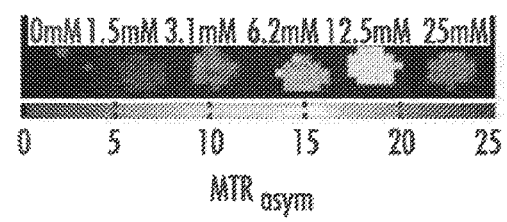
Figure 2F:
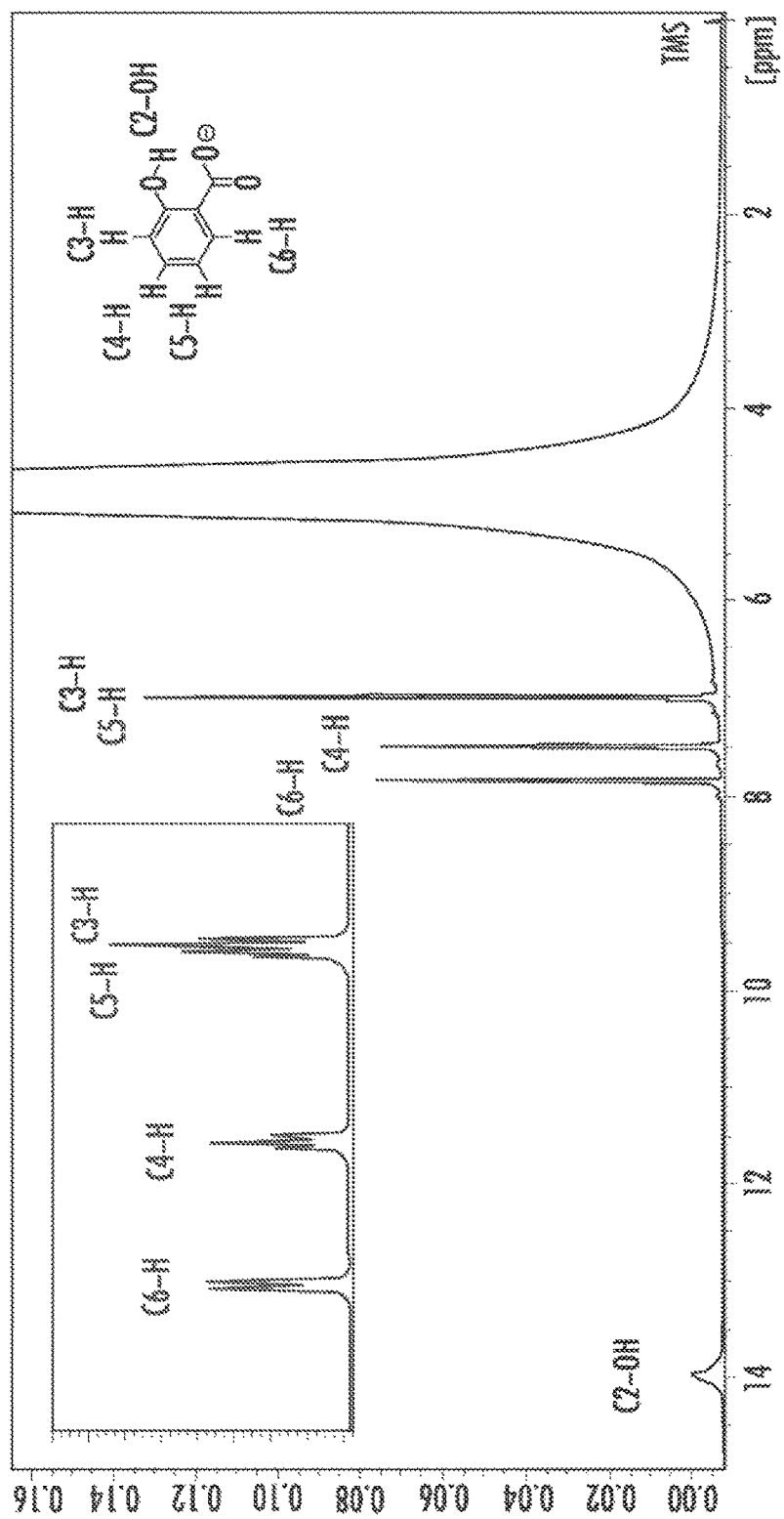
Figure 2G:
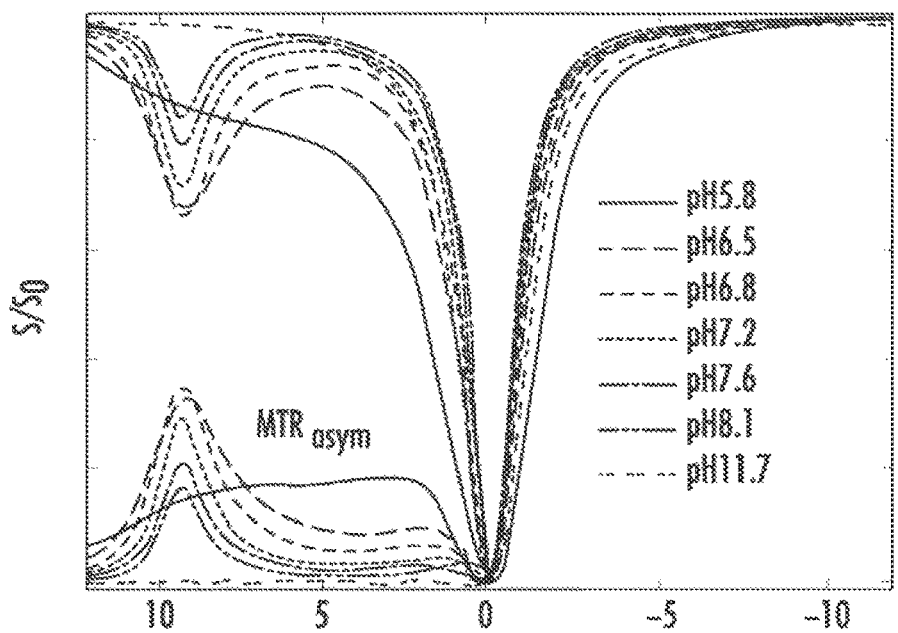
Figure 2H:
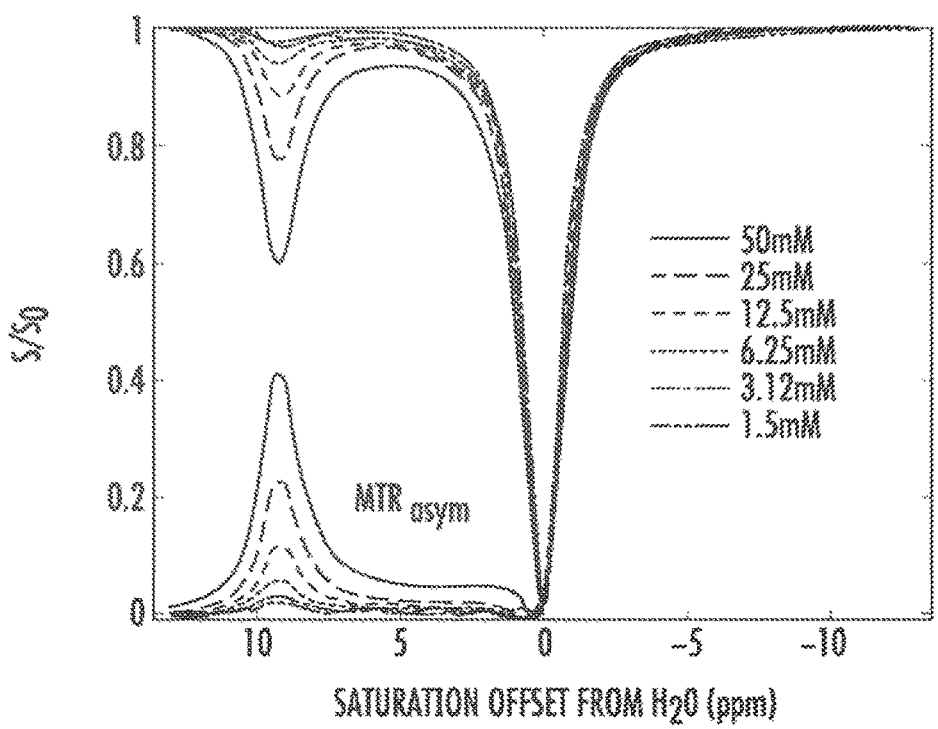
Figure 3A:
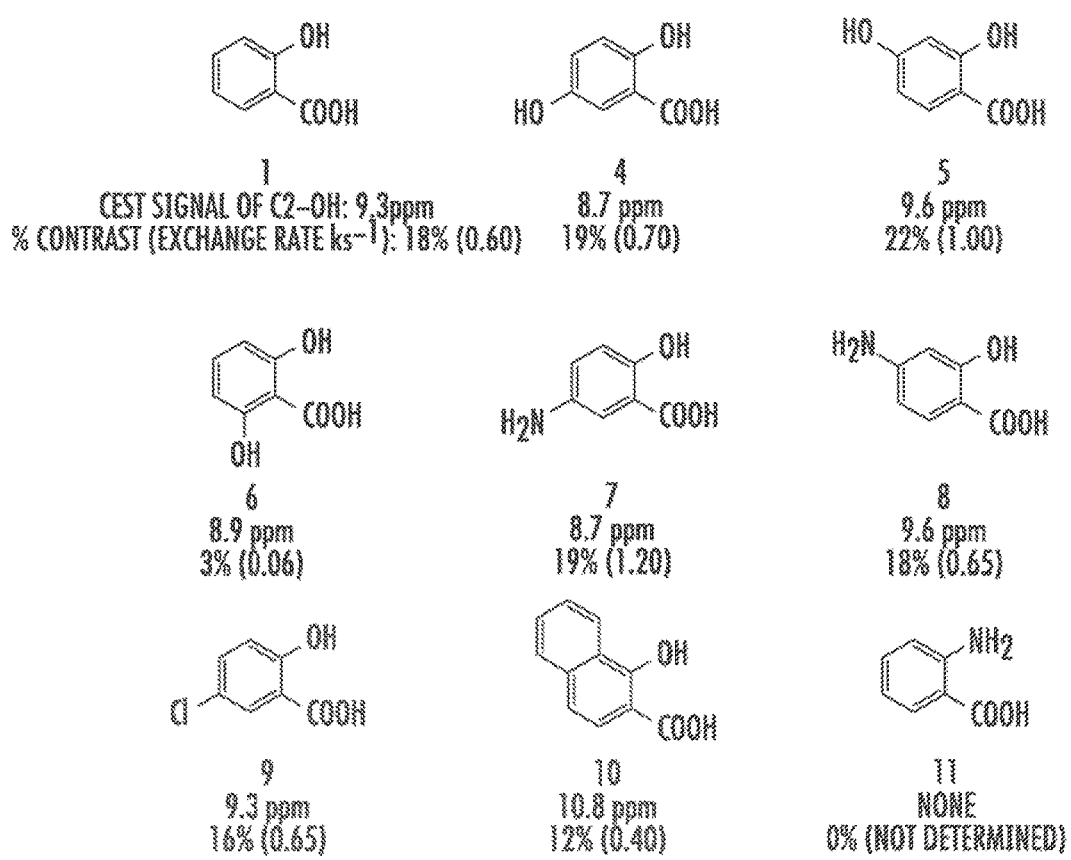
Figure 3B:
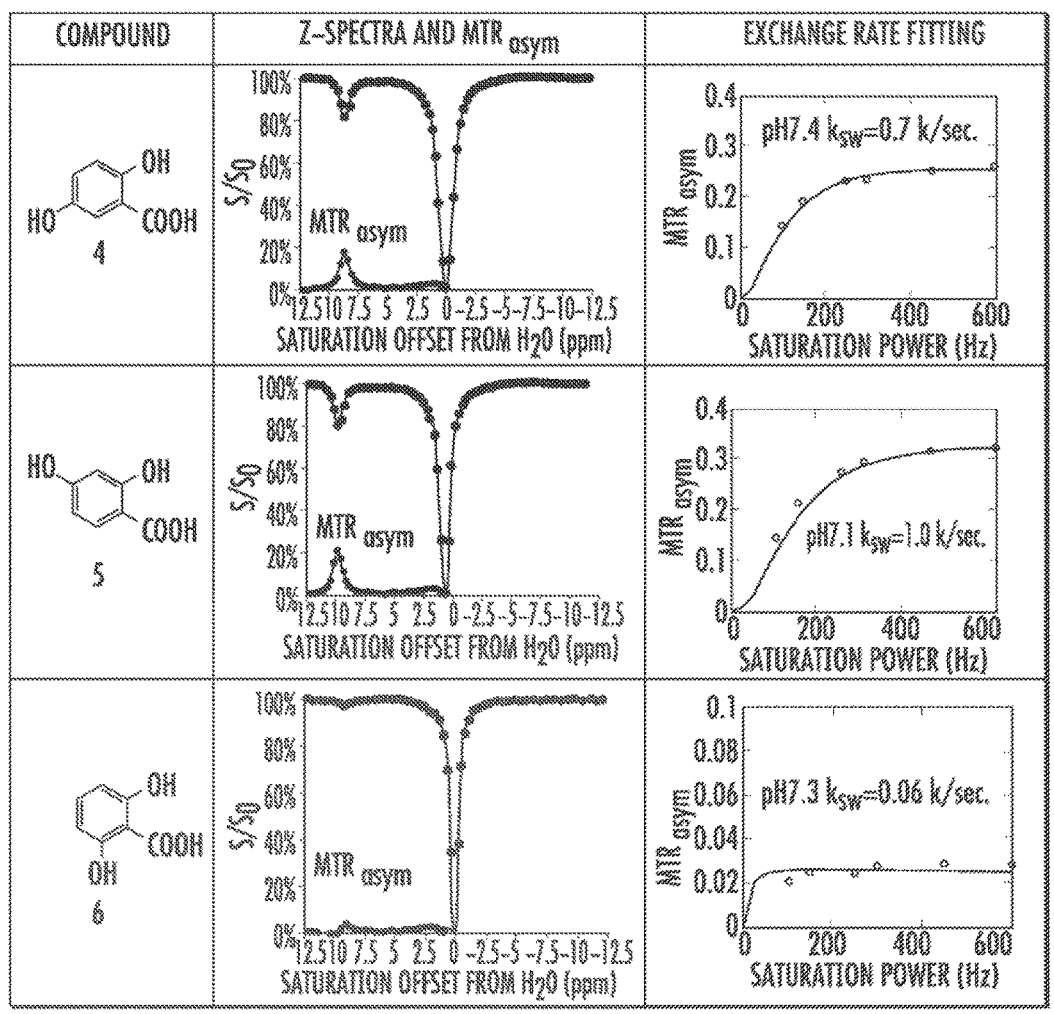
Figure 4A:
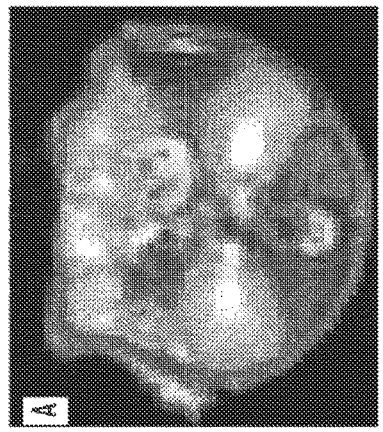
Figure 4B:
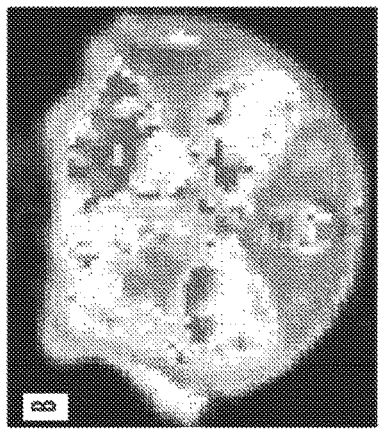
Figure 4C:
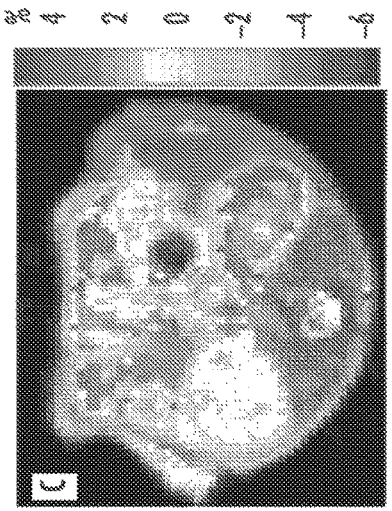
Figure 4D:
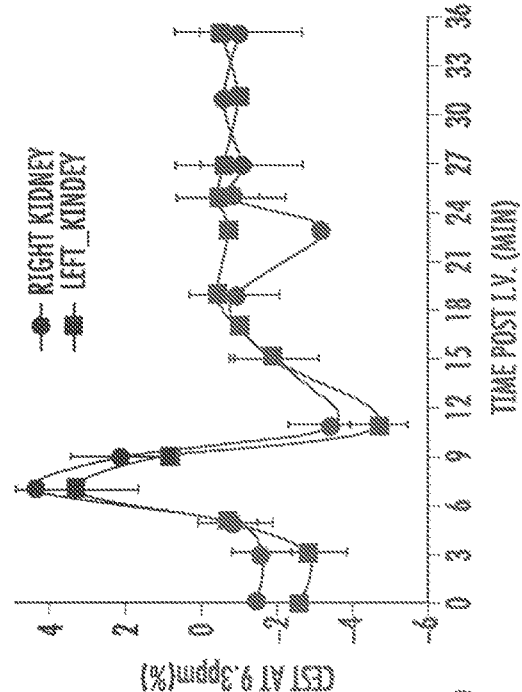
Figure 4E:
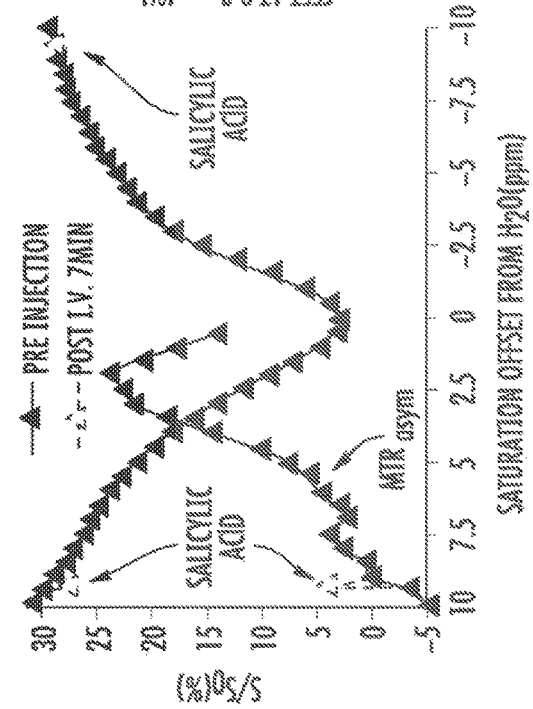
Figure 4F:
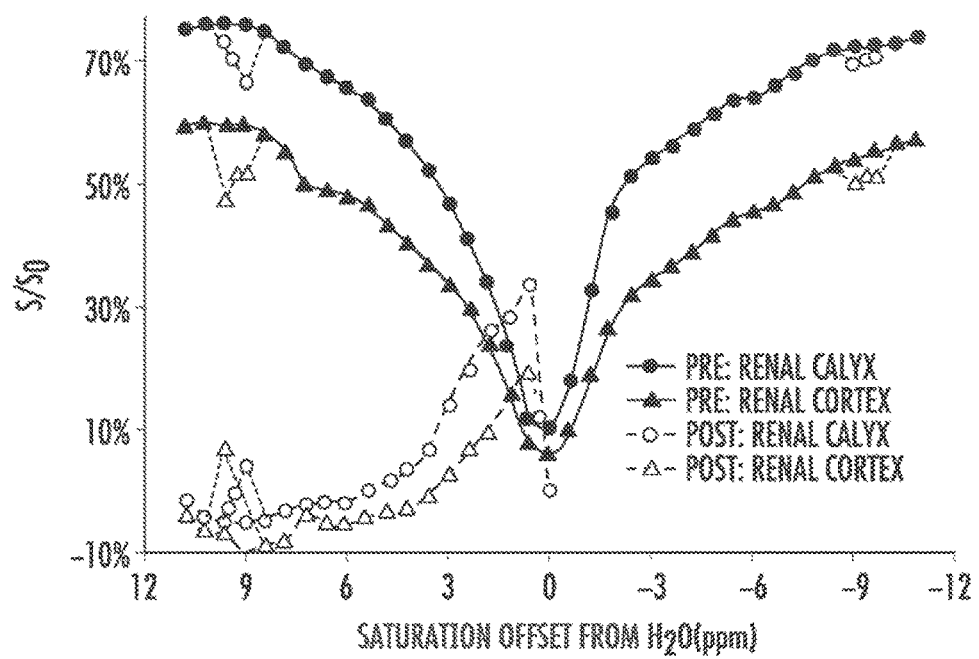
Figure 4G:
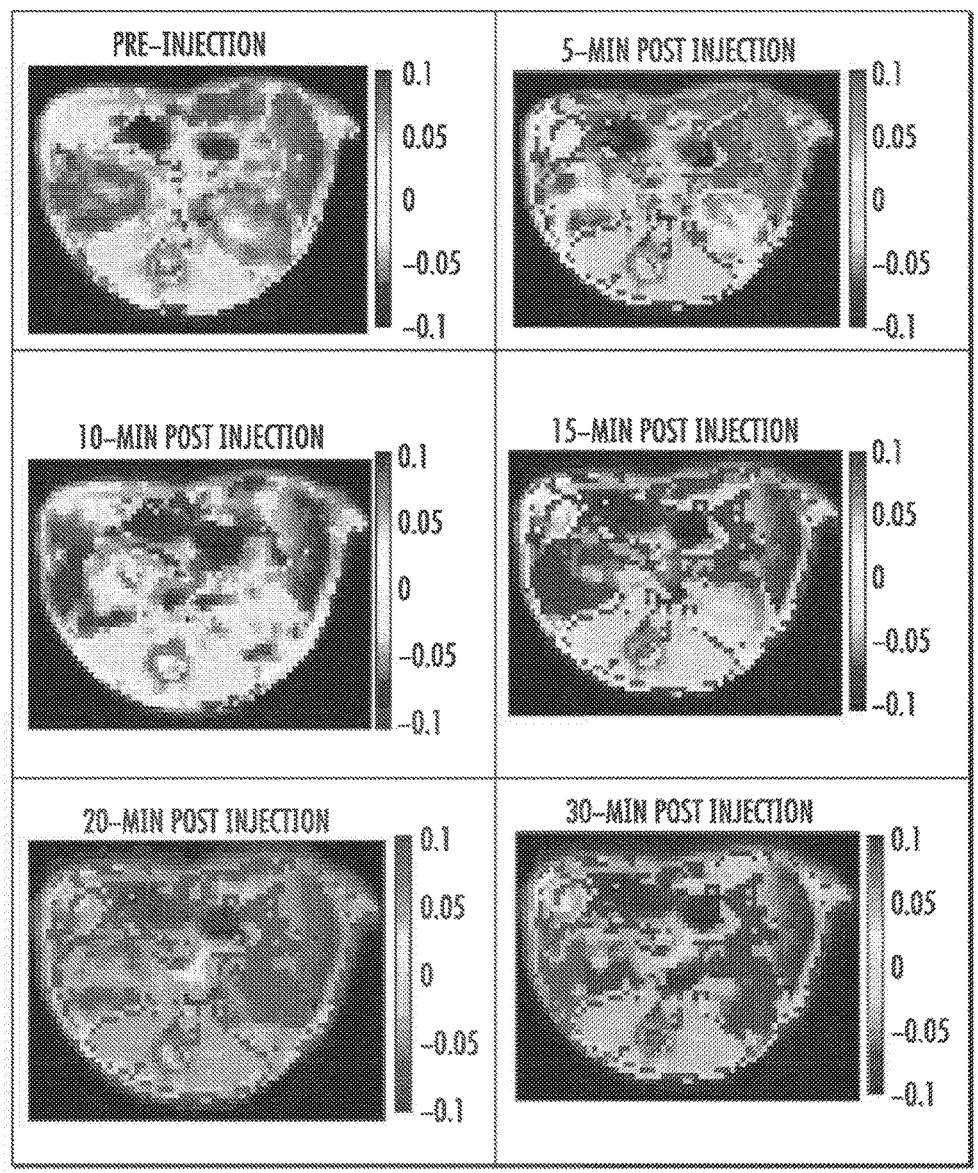
Figure 4H:
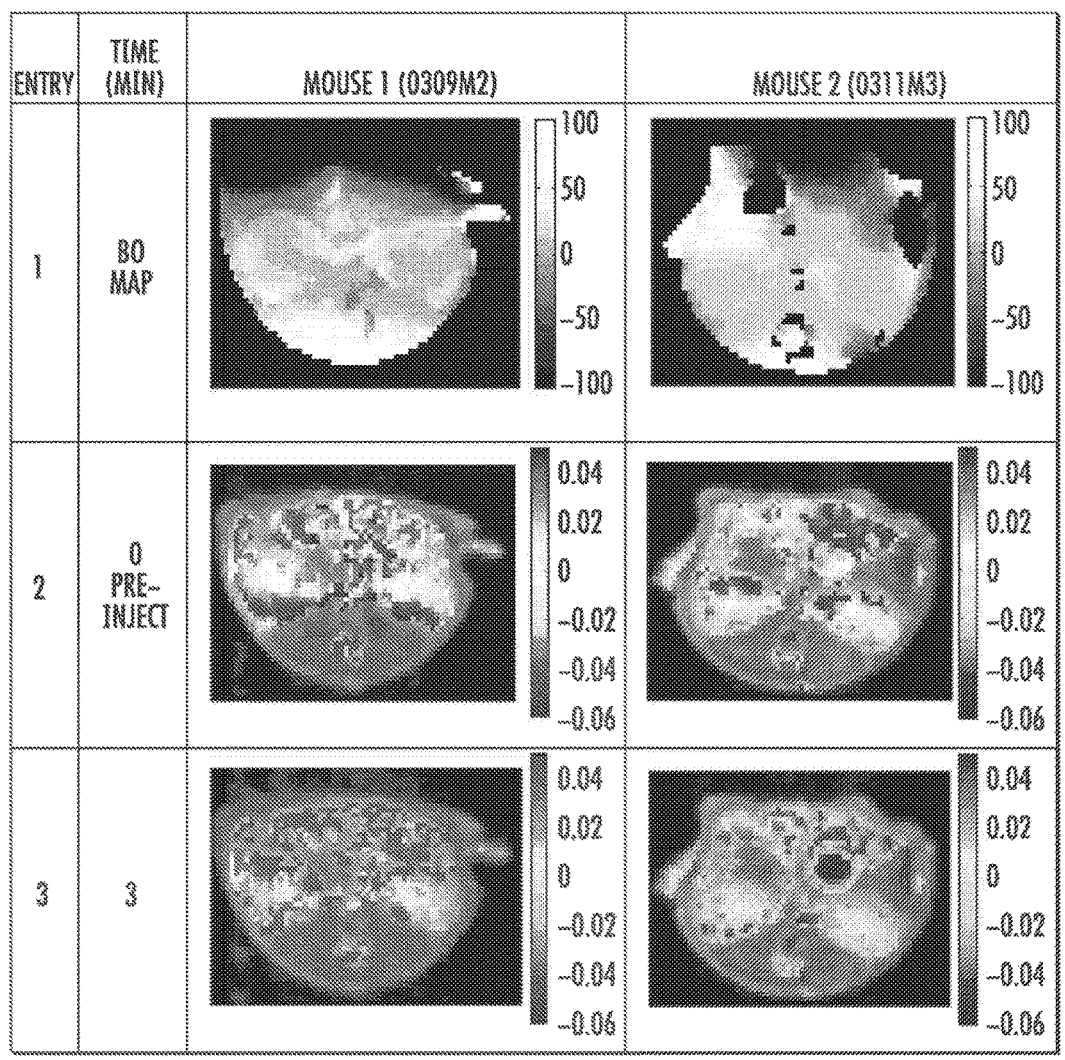
Figure 4E:
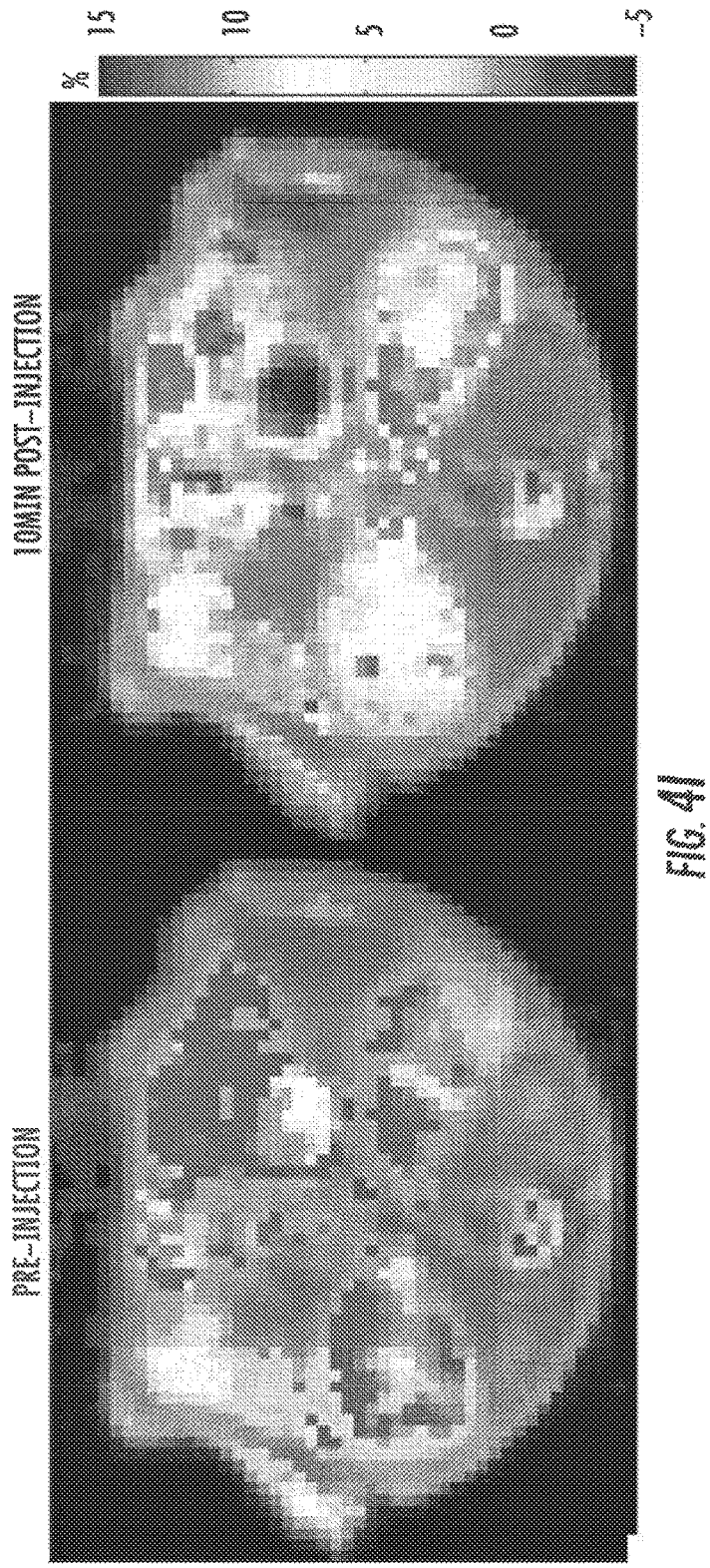
Figure 5A:
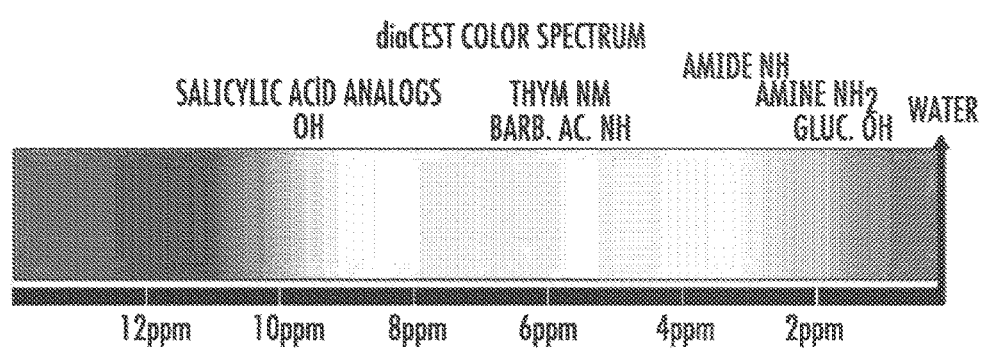
Figure 5B:
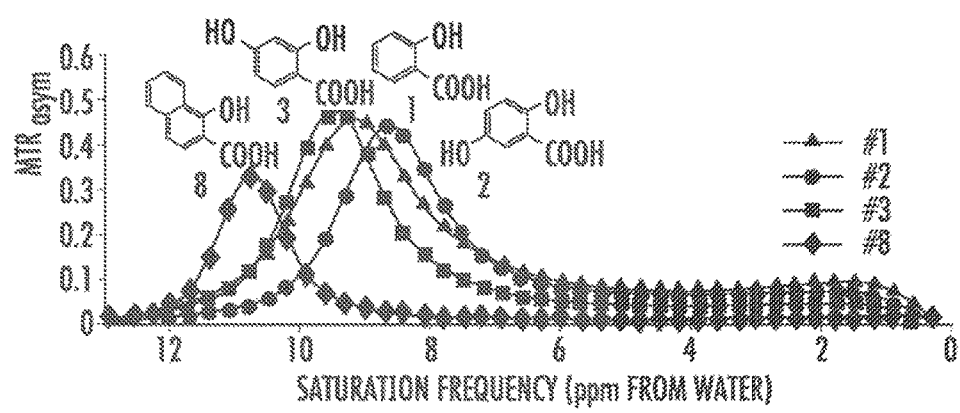
Figure 6:
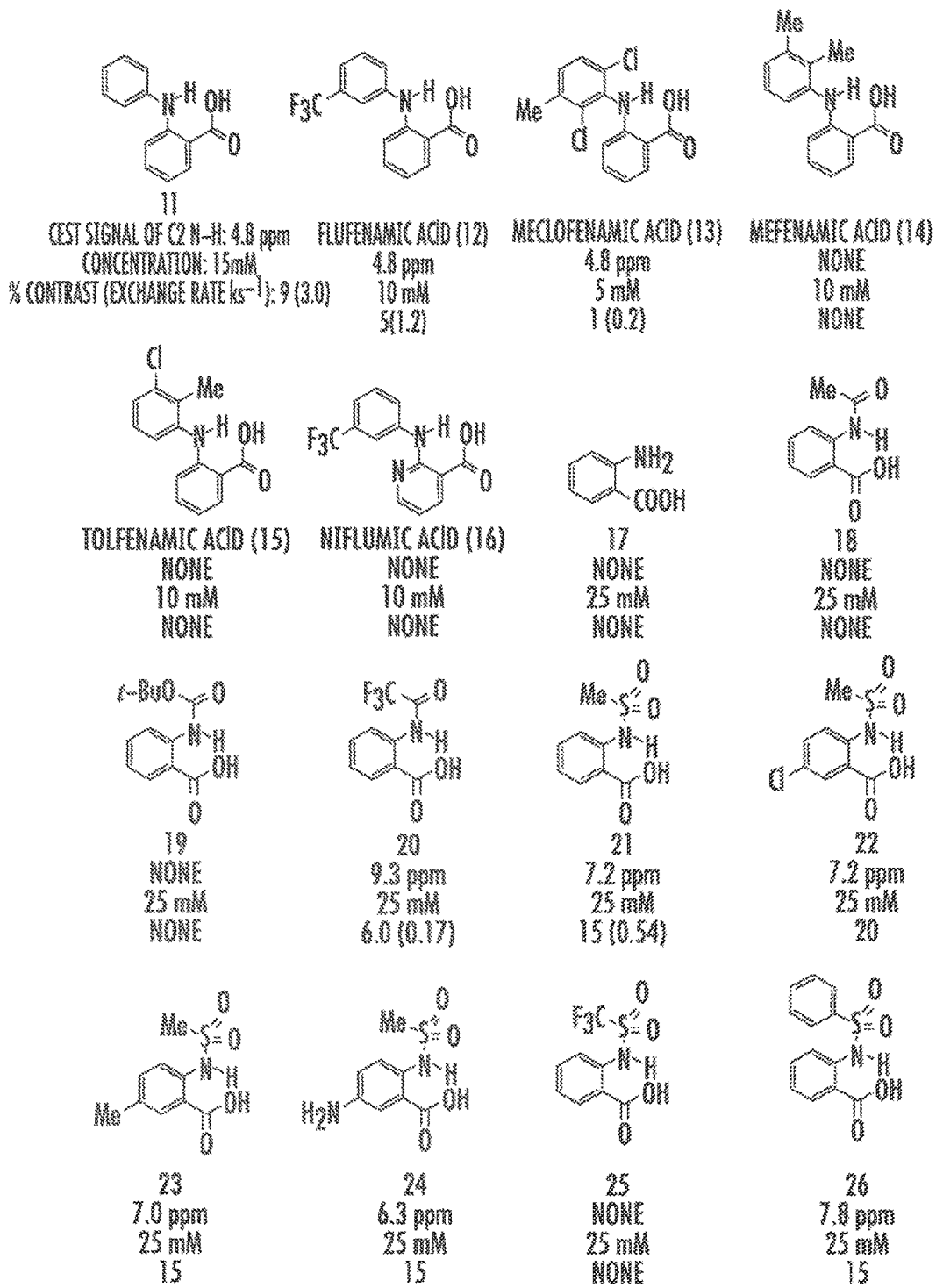
Figure 7:
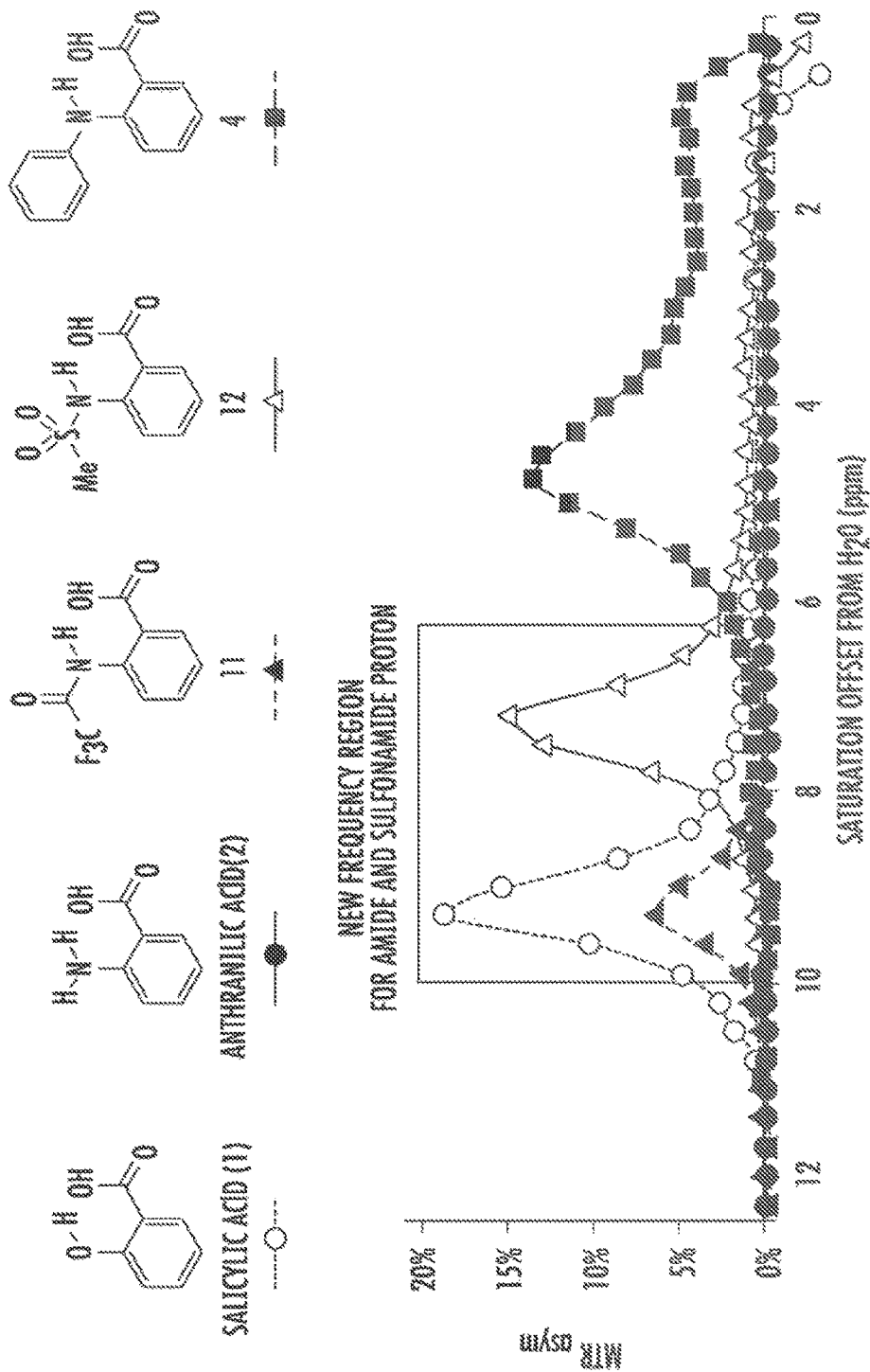
Figure 11A:
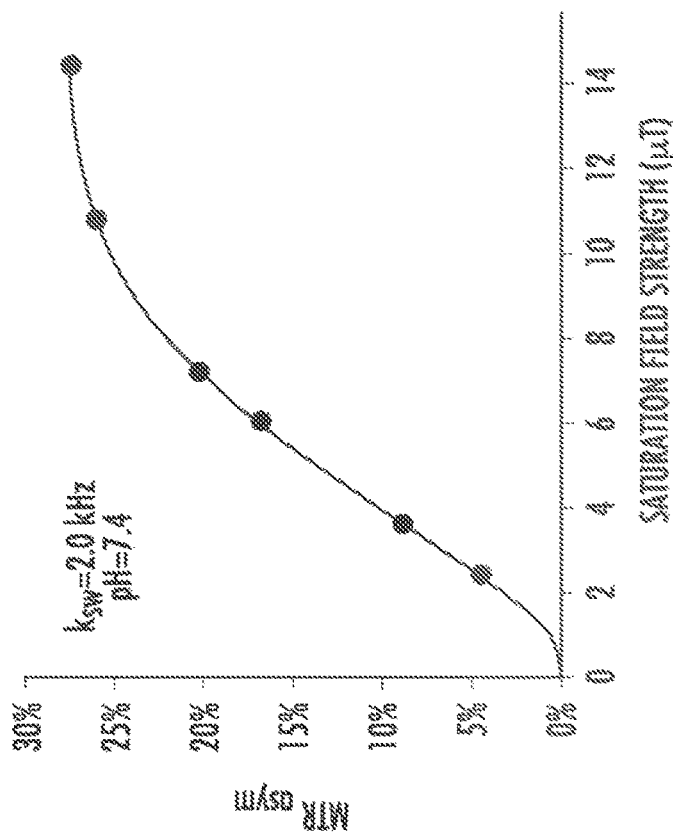
Figure 11B:
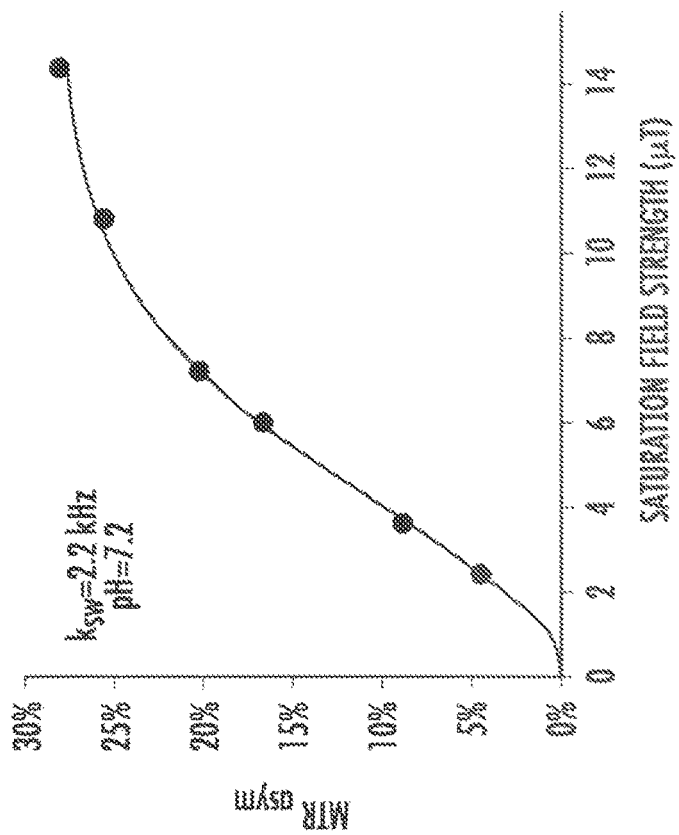

FIG. 2B shows QUESP data for 25 mM, at pH values 6.5, 7.0, 7.4. FIG. 2C shows the pH dependence of $k_{sw}$ based on QUESP data. FIG. 2D shows CEST contrast at 9.3 ppm as a function of concentration, using ω1=7.2 μT. FIG. 2E shows a CEST contrast map on phantom with assorted concentrations using ω1=7.2 μT. FIG. 2F shows an H-NMR spectrum of salicylic acid in water that depicts the spectra and proton assignment of salicylic acid (1) dissolved in 0.01 M PBS with 10% deuterium oxide at the concentration of 25 mM and titrated with HCl/NaOH to pH 7.0 according to an exemplary embodiment of the presently disclosed subject matter. FIGS. 2G and 2H show graphs depicting Z-spectra data for at different pH and concentrations, respectively;

FIGS. 3A and 3B show an array of salicylic acid analogs and a table, respectively. FIG. 3A shows CEST signals of salicylic acid and selected analogs according to an exemplary embodiment of the presently disclosed subject matter with the following experimental conditions: CEST contrast were obtained at 25 mM concentration, pH 7.1-7.4, using saturation pulse tsat=3 sec, ω1=3.6 μT. FIG. 3B shows a table of Z-spectra and $MTR_{asym}$ for exemplary salicylic acid analogs;

FIGS. 4A-4I show three images, three graphs, and a three contrast image montages, respectively, according to an exemplary embodiment of the presently disclosed subject matter. FIGS. 4A to 4C show in vivo contrast for compound 1, where FIG. 4A is a T2w image, FIG. 4B is an overlay $MTR_{asym}$ (9.3 ppm) map pre-injection, and FIG. 4C is an overlay $MTR_{asym}$ (9.3 ppm) map at 7 min post-injection. FIG. 4D is Z-spectra and $MTR_{asym}$ for a region of interest (ROI) enclosing the entire right kidney with pre-injection data (black), 7 min post-injection; (light blue) and FIG. 4E is a dynamic time course of the $MTR_{asym}$ (9.3 ppm) for ROIs enclosing the whole left kidney and right kidney. ω1=7.2 μT (n=2). FIG. 4F shows in vivo Z-spectra and $MTR_{asym}$ spectra for renal calyx and cortex, acquired both pre-injection and at 5 min post injection according to an exemplary embodiment of the presently disclosed subject matter. FIG. 4G shows dynamic CEST contrast maps pre- and post-injection at 5.9 µT, according to an exemplary embodiment of the presently disclosed subject matter. FIG. 4H shows dynamic contrast maps for two mice, according to an exemplary embodiment of the presently disclosed subject matter. FIG. 4I shows CEST contrast maps map at 9.5 ppm pre-(left panel) and 10 min post-(right panel) of a mouse abdomen both pre- and post-i.v. injection of salicylic acid, respectively;

FIGS. 5A-5B show a proton shift spectrum and a graph, respectively, that illustrate the color spectrum for diaCEST agents according to an exemplary embodiment of the presently disclosed subject matter;

FIG. 6 shows a summary of CEST signal of beta-aminocarboxylates derivatives according to an exemplary embodiment of the presently disclosed subject matter;

FIG. 7 shows CEST contrast curves for representative salicylic acid (1) and anthranilic acid derivatives (2, 4, 11 and 12) at concentrations of 25 mM (pH 7.1-7.4) using B1=3.6 µT, Tsat=3 s. The gray box indicates this group of agents includes a new frequency region for amide and sulfonamide protons;

FIGS. 8A and 8B are CEST properties of 5. (a) QUESP data at 10 mM at pH=7.4, with $k_{sw}$=1.0 kHz where the data are shown as points and the solid line represents the best fit after numerically solving the two-pool Bloch equations; (b) CEST contrast at 4.8 ppm as a function of concentration using B1=3.6 µT (solid line: linear fitting);

FIGS. 9A-9E show CEST properties of 10-16: (a) Z-spectra and $MTR_{asym}$ for 10-12 at 25 mM, pH=7.2, Tsat=3 s and B1=3.6 µT; (b) CEST contrast of 12 at 7.5 ppmas a function of concentration, using B1=3.6 µT; (c) QUESP data of 12 at 25 mM, pH=7.1, with $k_{sw}$=0.6 kHz; (d) pH dependence of percentage contrast for 12; and (e) analogs of 12 with different CEST peak frequencies from 6 to 8 ppm;

FIGS. 10A-10E show in vivo contrast for 13. (a) T2w image; (b) overlay $MTR_{asym}$ map pre-injection for mouse 1; (c) overlay $MTR_{asym}$ map at 10 min post-injection for mouse 1; (d) histogram displaying the distribution of $MTR_{asym}$ for mouse 1 pre- and post-injection (c, d). (e) Dynamic time course of $\Delta MTR_{asym}$ based on regions of interest enclosing both left and right kidneys for the two mice using ω1=3.6 µT (circle: mouse 1; triangle: mouse 2; solid line, average value of mouse 1 and mouse 2);

FIGS. 11A and 11B are QUESP data for compound 4 at 15 mM was acquired at pH 7.2 and 7.4. As shown, $k_{sw}$ dropped slightly from 2.2 kHz at pH 7.2, to 2.0 kHz at pH 7.4.

Figure 12:
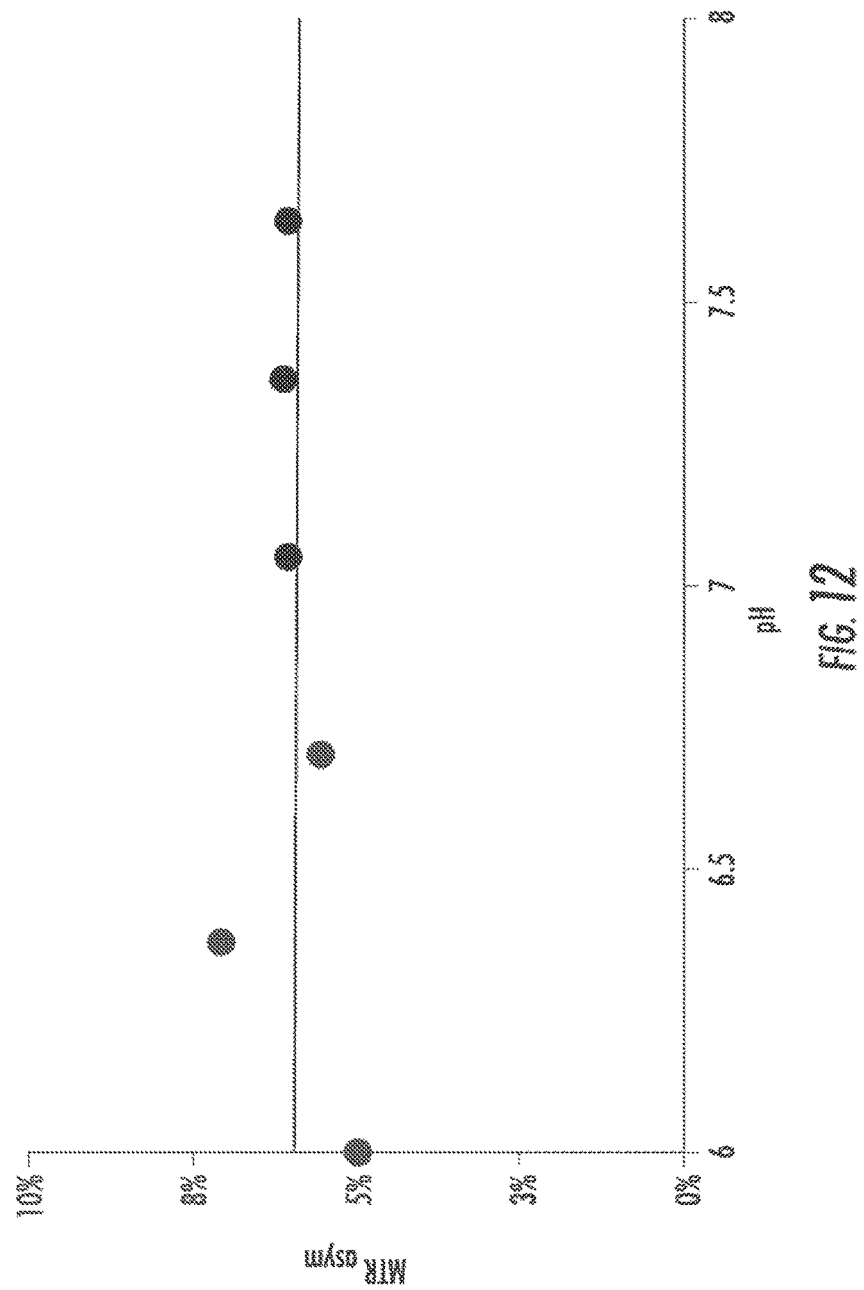
Figure 13C:
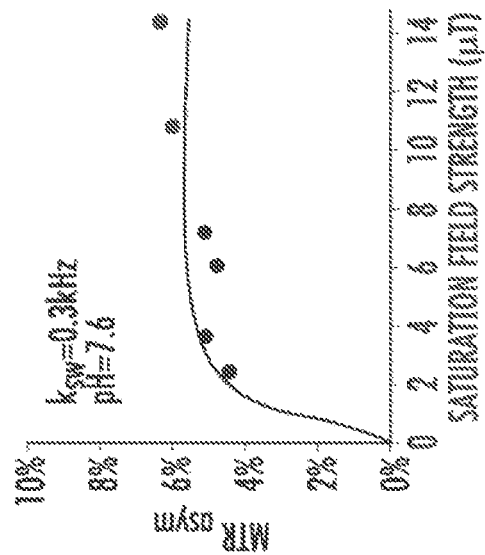
Figure 13B:
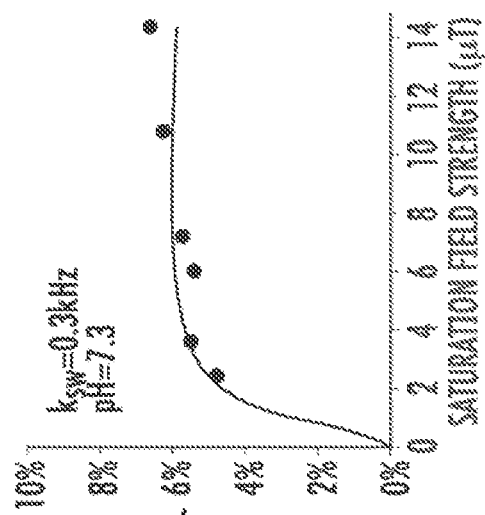
Figure 13A:
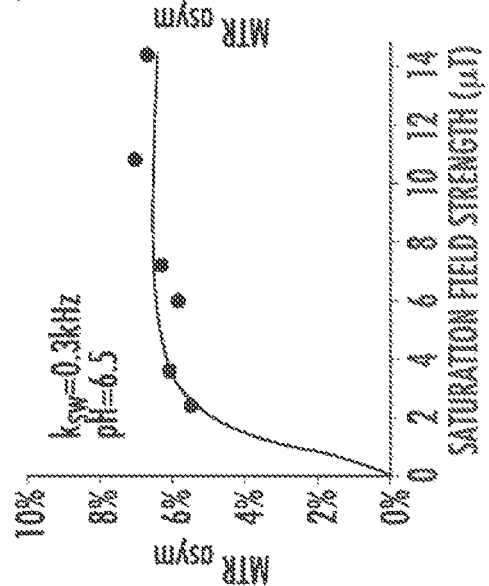
Figure 14:
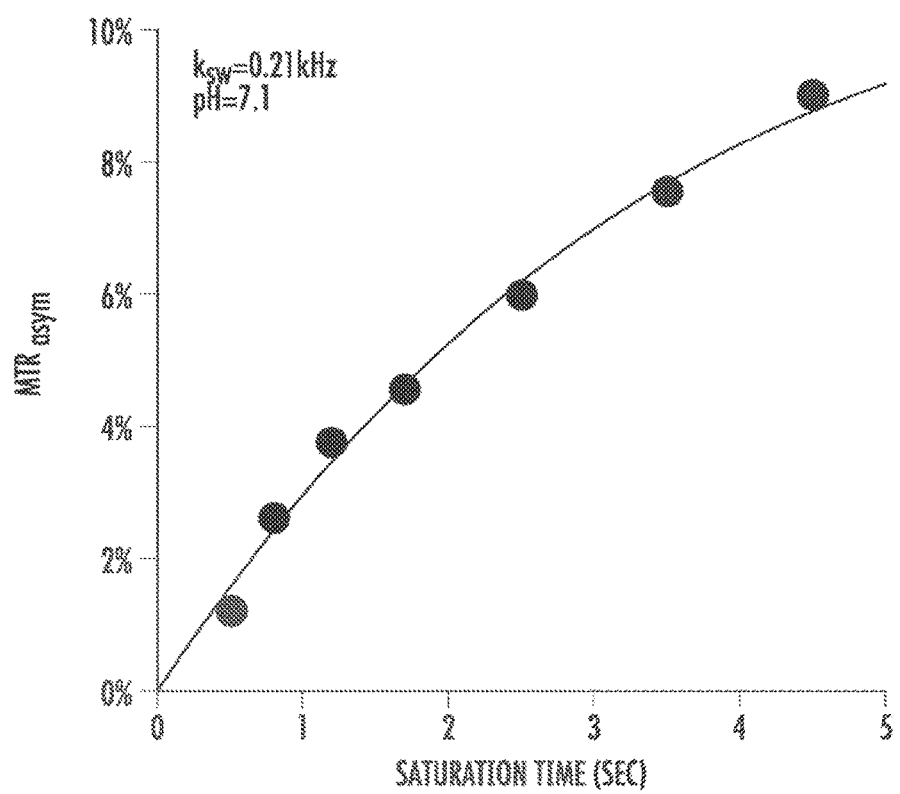
Figure 15A:
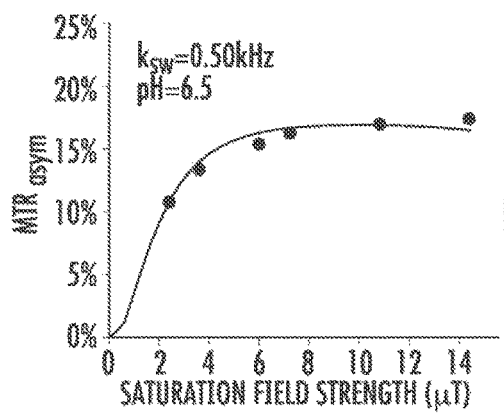
Figure 15B:
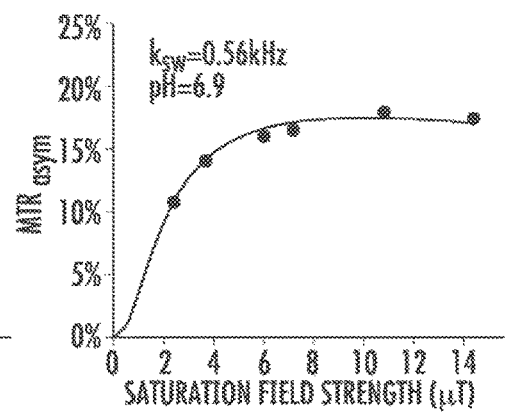
Figure 15C:
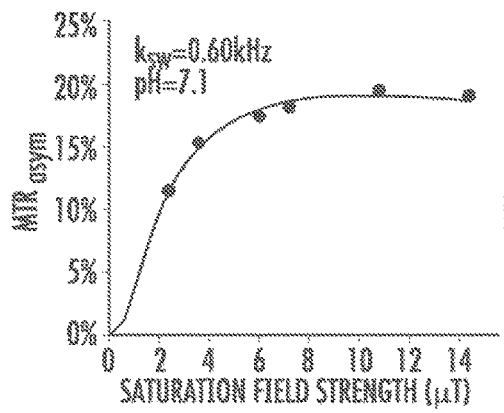
Figure 15D:
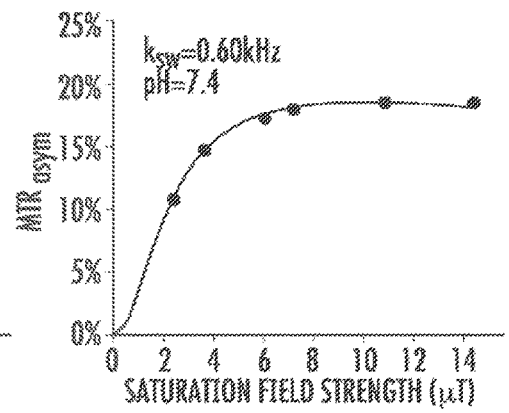
Figure 16:
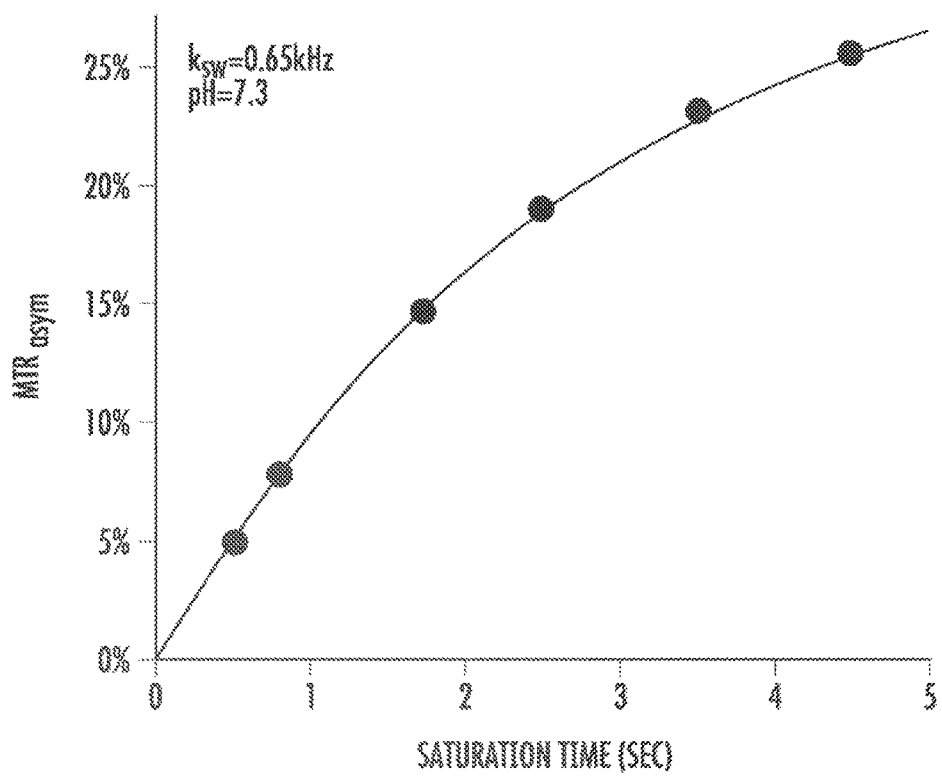
Figure 17:
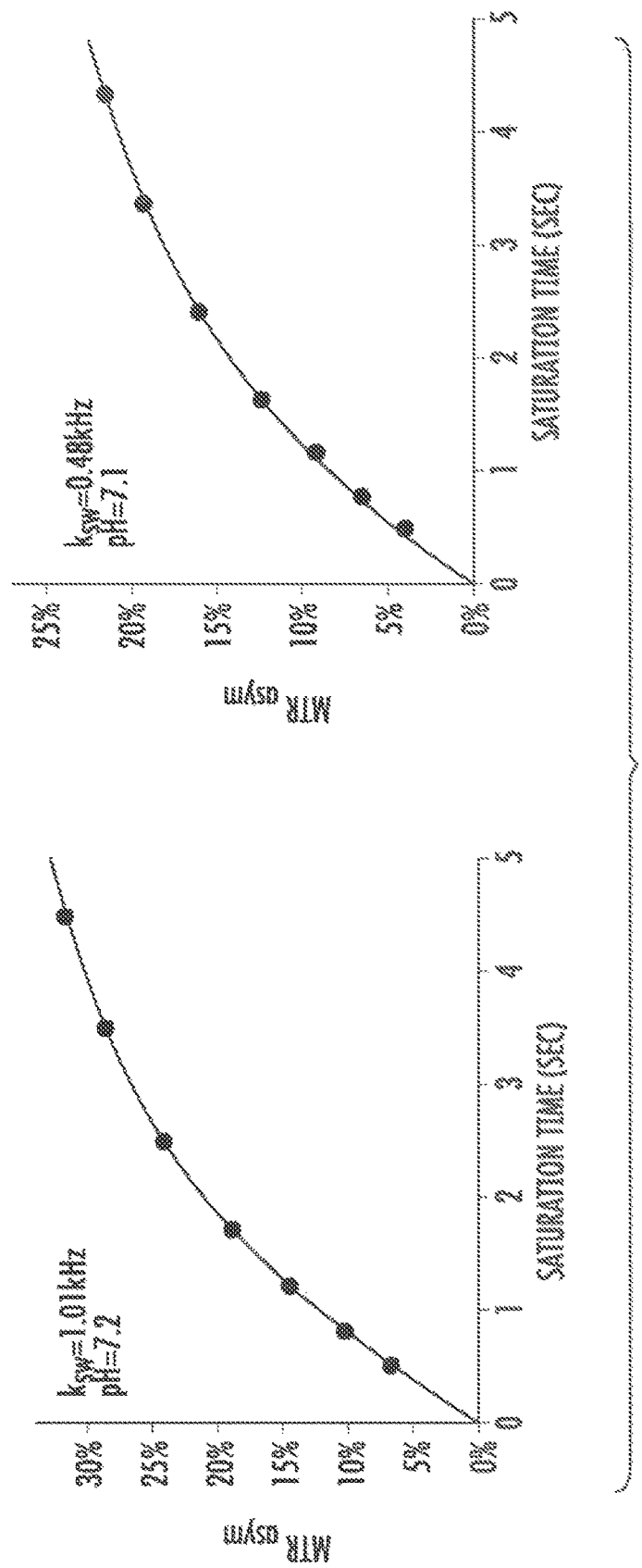
Figure 18:
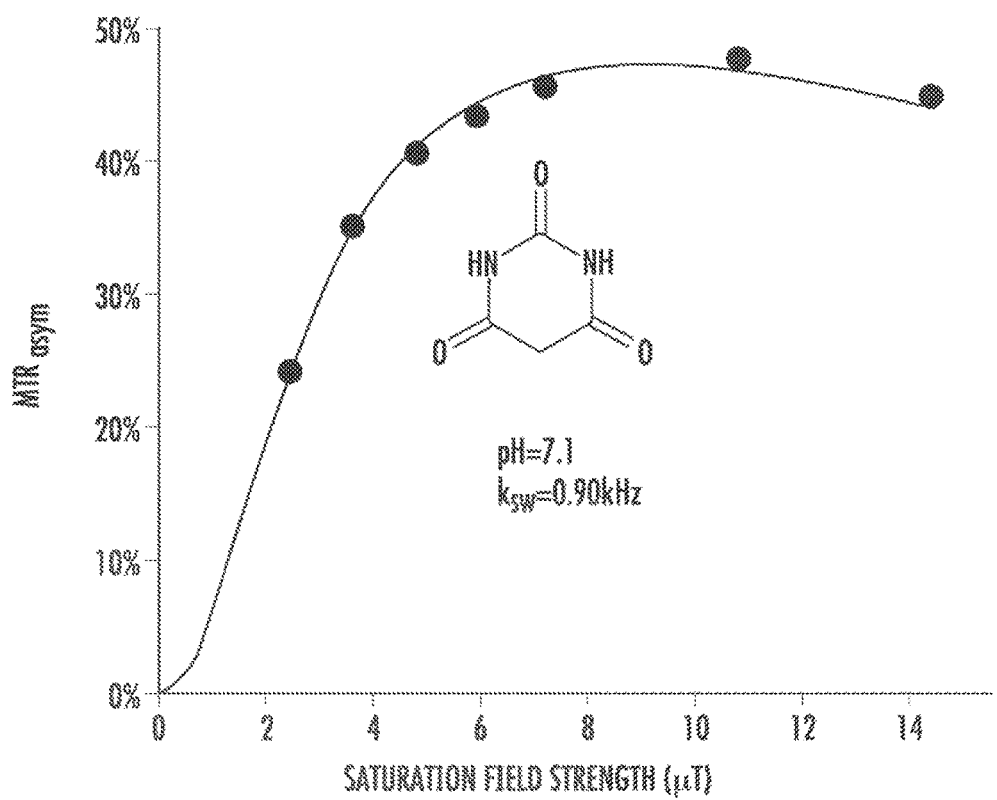
Figure 19:
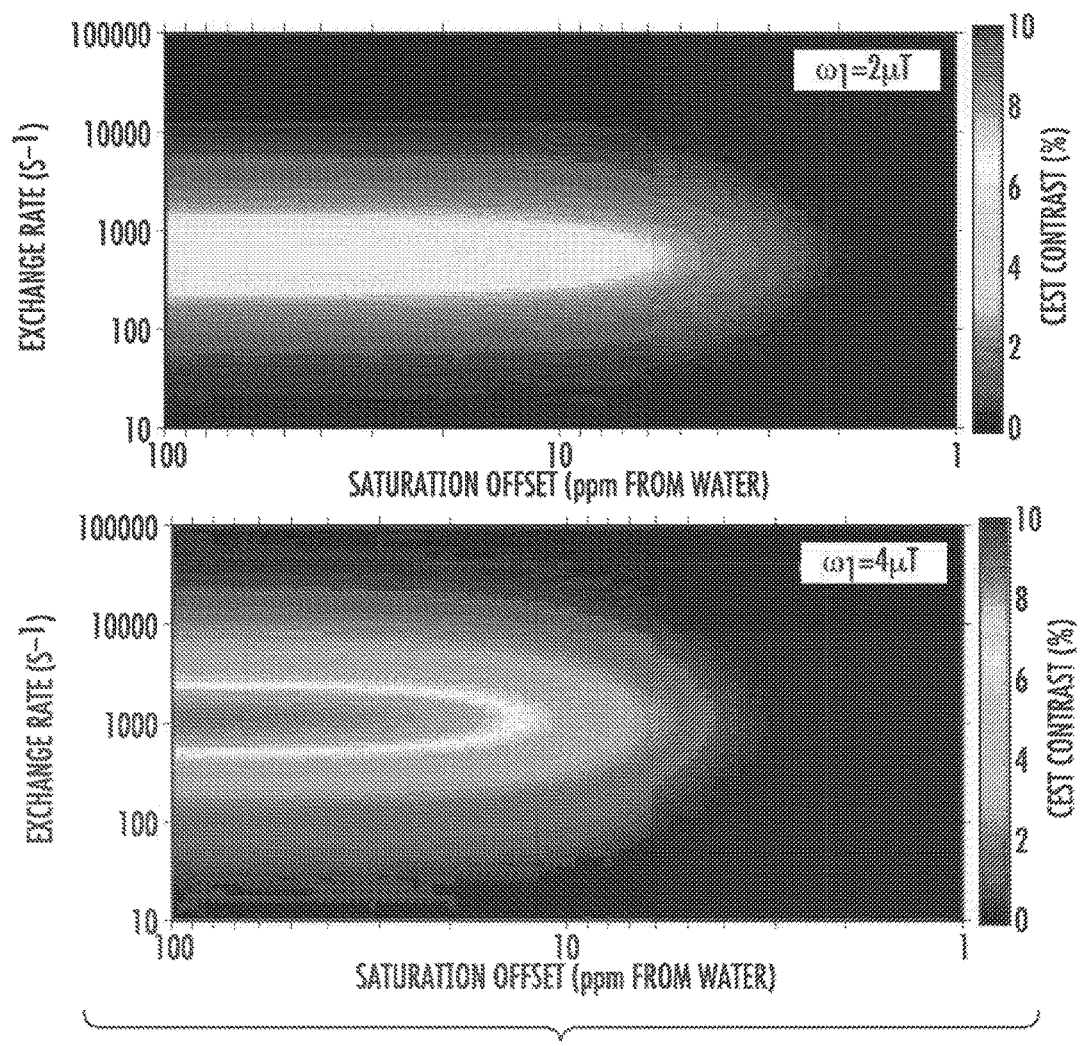
Figure 20:
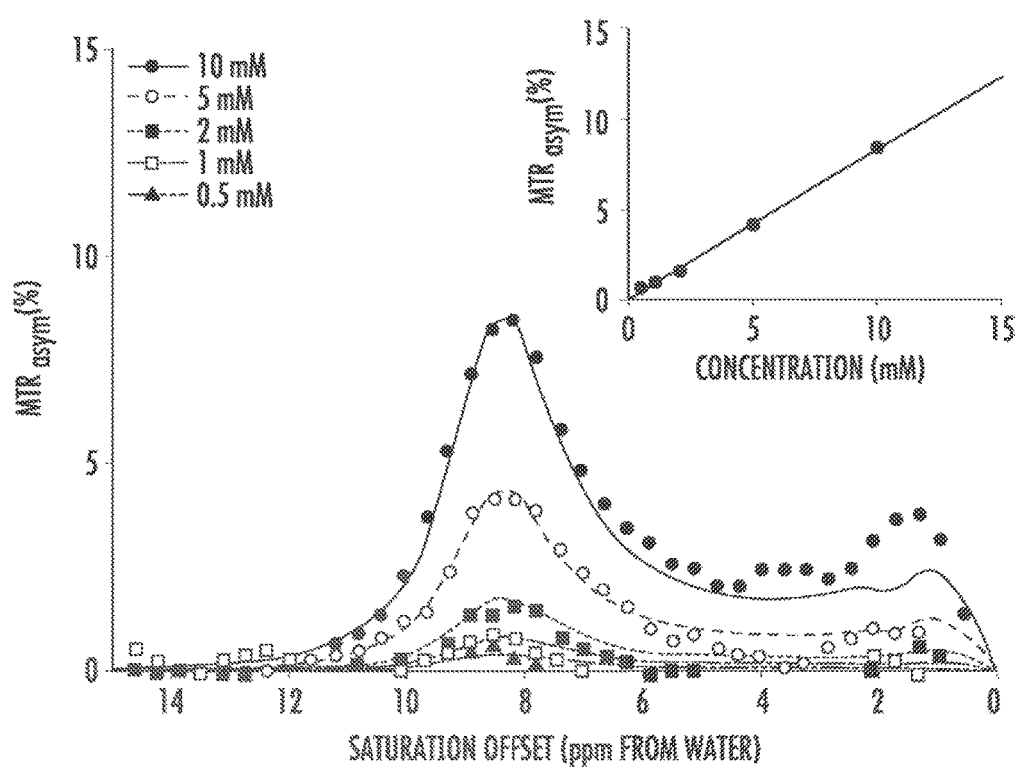
Figure 21:
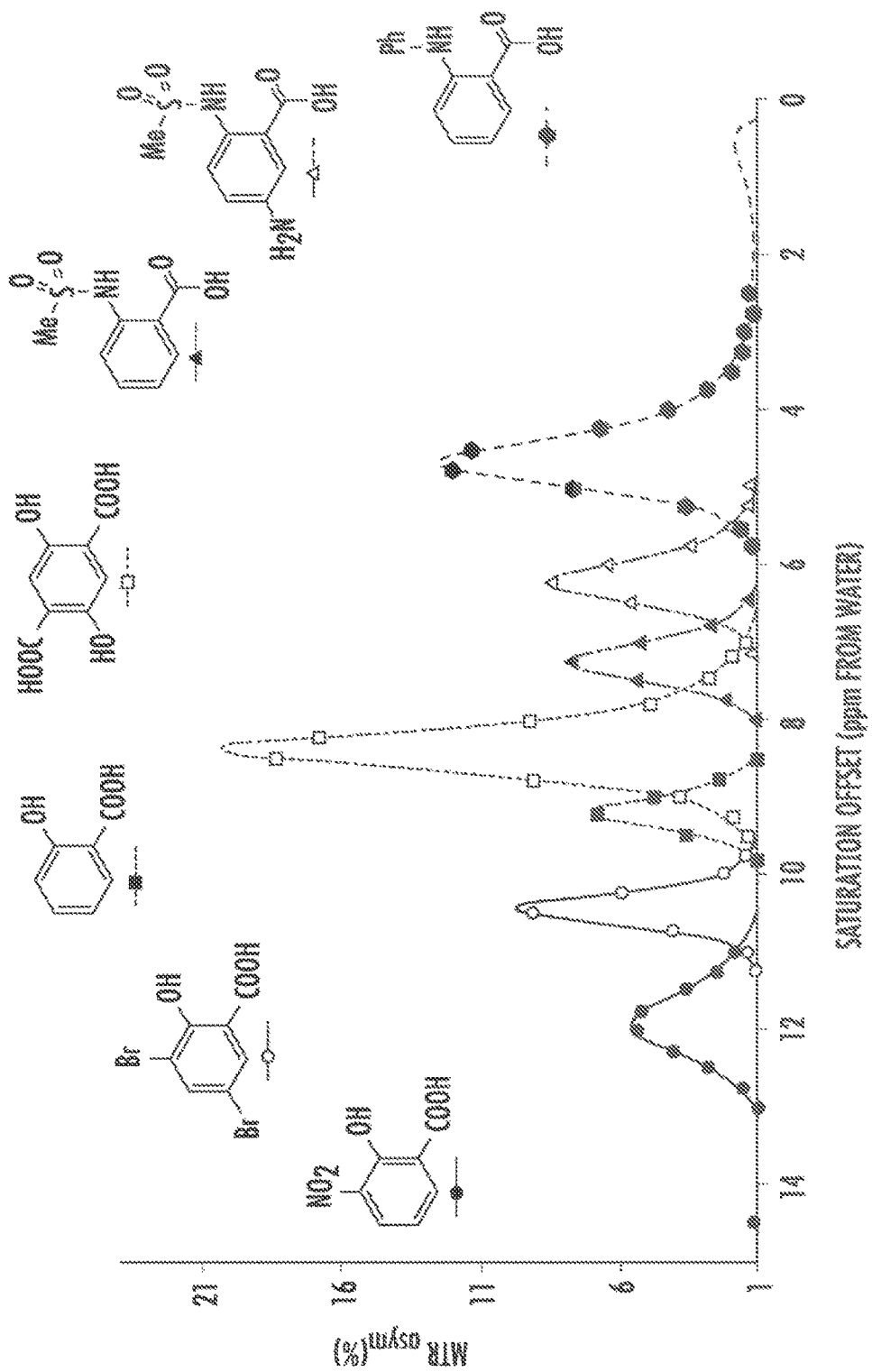
Figure 22:
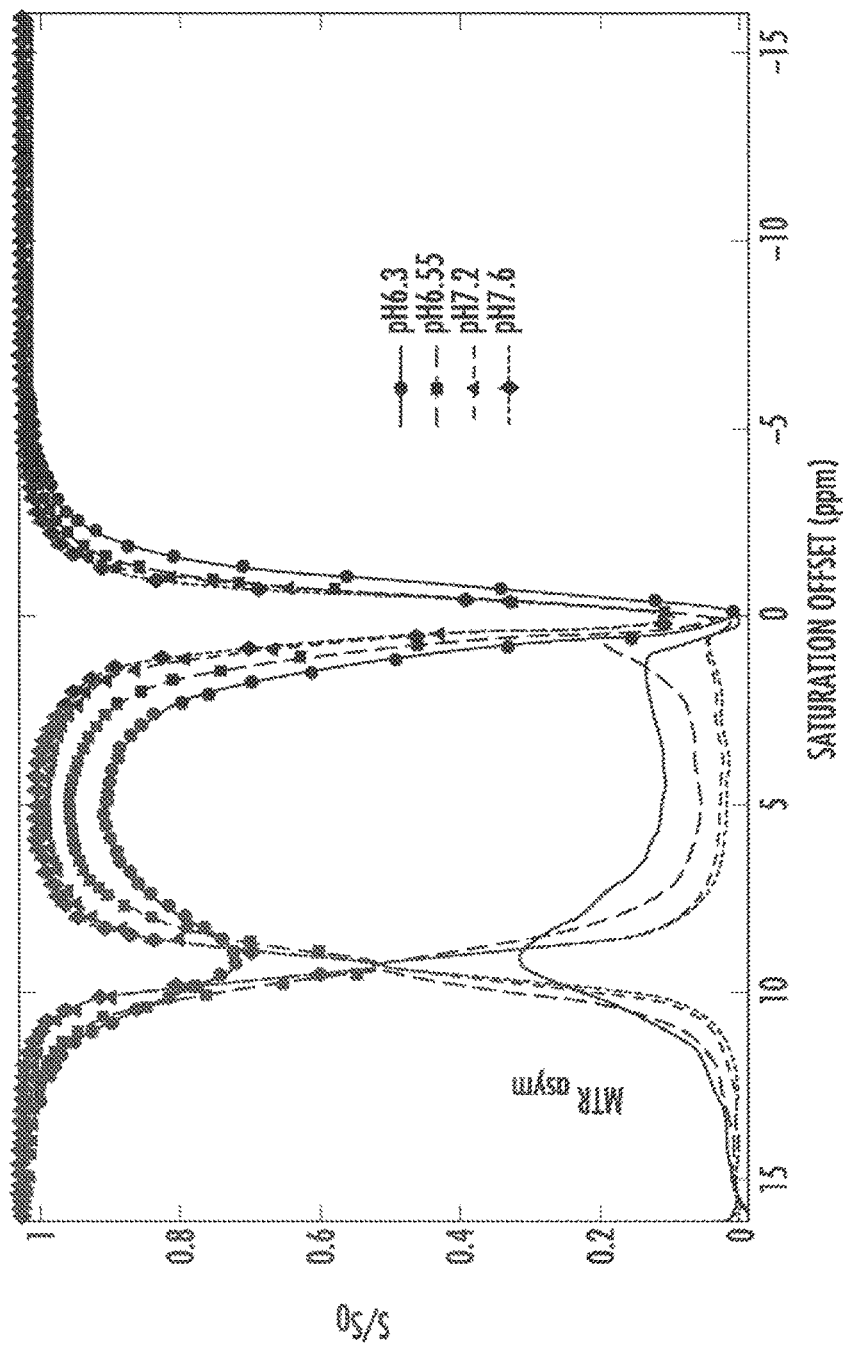
Figure 23:
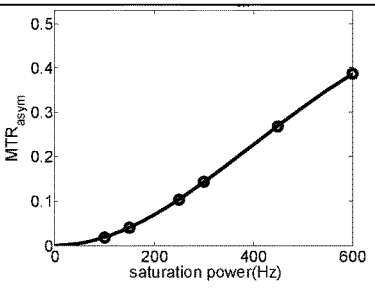
Figure 23:
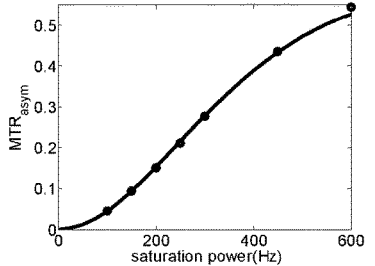
Figure 23:
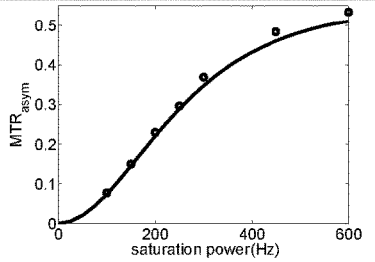
Figure 23:
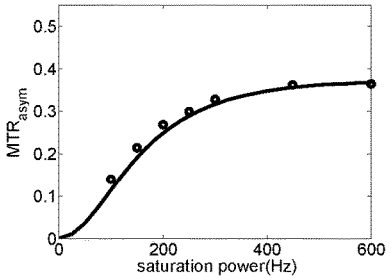
Figure 23:
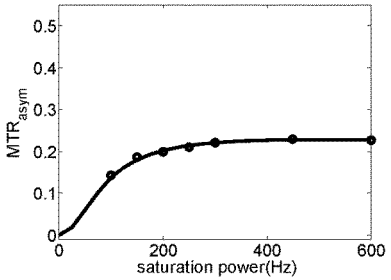
Figure 23:
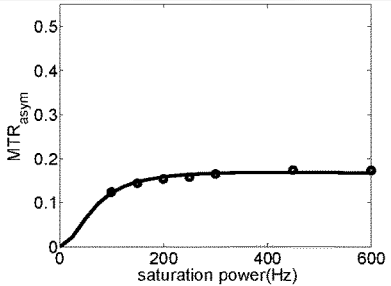

FIG. 12 shows the pH dependence of CEST contrast for compound 11;

FIGS. 13A-13C are QUESP data for compound 11 as a function of pH at 25 mM, According to QUESP fittings, $k_{sw}$=0.3 kHz at pH 6.5, 0.3 kHz at pH 7.3, and 0.3 kHz at pH 7.6;

FIG. 14 shows QUEST data for compound 11 (25 mM) with $B_1$=4.8 µT;

FIGS. 15A-15D are QUESP data to determine $k_{sw}$ as a function of pH for compound 12. According to the fits, k sw only changed slightly for different pH values (0.50 kHz at pH 6.5, 0.56 kHz at pH 6.9, 0.60 kHz at pH 7.1 and 0.60 kHz at pH 7.4);

FIG. 16 shows QUEST data for compound 12 (25 mM) with $B_1$=4.8 µT;

FIG. 17 shows QUEST data for compound 13 (Left) and 14 (Right) (25 mM) with $B_1$=4.8 µT;

FIG. 18 shows QUESP data to determine $k_{sw}$ for barbituric acid, an agent reported by Balaban and co-workers. Ward, et al., *J Magn Reson* (2000);

FIG. 19 shows simulated CEST contrast at 3 T as a function of labile proton chemical shift and exchange rate;

FIG. 20 shows the concentration dependence and detection limit of 2,5-dihydroxyterephthalic acid (42) at 3 T; Conditions: CEST data were obtained at 10 mM, 5 mM, 2 mM, 1 mM, 0.5 mM concentrations, pH 7.3-7.4, tsat=3 sec, ω1=2.1 µT and T=32° C. For the inner panel, the CEST contrast at 8.5 ppm was plotted. Experimental data are shown as closed circles, while the lines represent Bloch simulations;

FIG. 21 shows high performance IM-SHY agents with different exchangeable proton frequencies. Conditions: CEST data were obtained at 17.6 T using 10 mM concentrations, pH 7.3-7.4, tsat=3 sec, ω1=3.6 µT and T=37° C. Experimental data are shown as closed circles, while the lines represent Bloch simulations;

FIG. 22 shows CEST Zspectra and $MTR_{asym}$ spectra for 100 mM salicylic acid at different pH values ($B_0$=11.7 T);

FIG. 23 shows calculated proton exchange rate of salicylic (1) at different pH;

FIG. 24 shows Z-spectra of N-alkyl/aryl-anthranilic acid analogues (2-9); and

FIG. 25 shows Z-spectra of N-acyl and 2-(methylsulfonamido) benzoic acid analogues (10-17).

DETAILED DESCRIPTION

The presently disclosed subject matter now will be described more fully hereinafter with reference to the accompanying Examples and Figures, in which some, but not all embodiments of the presently disclosed subject matter are illustrated. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Examples and Figures. Therefore, it is to be understood that the presently disclosed subject matter is not to be limited to the specific embodiments disclosed and that modifications and other embodiments are intended to be included within the scope of the appended claims.

I. Compositions and Methods for Chemical Exchange Saturation Transfer (CEST) Based Magnetic Resonance Imaging (MRI)

Magnetic Resonance Imaging (MRI) has been widely used as a diagnostic tool to detect changes in soft tissue due to its exquisite spatial resolution. One of the standard methods to detect pathologies involves injection of a magnetic resonance (MR) contrast agent, such as the gadolinium (III) complexes routinely used for angiography (see e.g., Caravan, *Chem. Soc. Rev.* (2006); Kubicek and Toth, *Advances in Inorganic Chemistry* (2009)). Chemical exchange saturation transfer (CEST) contrast agents are a new alternative, which have become popular due to the unique features of these agents (see e.g., Hancu, et al., *Acta Radiol* (2010); Terreno, et al., *Contrast Media Mol. Imaging* (2010); Liu, et al., *NMR Biomed* (2013); van Zijl and Yadav, *Magn. Reson. Med.* (2011)). One of the attractive features of CEST probes is that MR contrast can be produced by a variety of organic diamagnetic compounds possessing exchangeable protons with suitable proton transfer rates (see e.g., Caravan, *Chem. Soc. Rev.* (2006); Kubicek and Toth, Advances in Inorganic Chemistry (2009) and Ward, et al., *J. Magn. Reson.* (2000)) such as, for example, glucose (see e.g., Chan, et al., *Magn. Reson. Med.* (2012); Jin. et al., *Magn. Reson. Med.* (2011); Torrealdea, et al., *Contrast Media Mol. Imaging* (2013)), glycogen (see e.g., van Zijl, et al., *Proc. Natl. Acad. Sci.*), myoinositol (see e.g., Haris, et al., *Neurosci. Meth.* (2013)), glutamate (see e.g., Cai, et al., *Nat. Med.* (2012)), creatine (see e.g., Hancu, et al., *Acta Radiol* (2010); Terreno, et al., *Contrast Media Mol. Imaging* (2010); Liu, et al., *NMR Biomed* (2013); van Zijl and Yadav, *Magn. Reson. Med.* (2011)), L-arginine (see e.g., Ward, et al., *J. Magn. Reson.* (2000)), glycosaminoglycans (see e.g., Ling, et al., *Proc. Natl. Acad. Sci. USA* (2008)), nucleic acids (see e.g., Chan, et al., *Magn. Reson. Med.* (2012); Jin. et al., *Magn. Reson. Med.* (2011); Torrealdea, et al., *Contrast Media Mol. Imaging* (2013)), and peptides (see e.g., McMahon, et al., *Magn. Reson. Med.* (2008); Airan, et al., *Magn. Reson. Med.* (2012); Salhotra, et al., *NMR Biomed* (2008)).

The CEST contrast mechanism involves selective irradiation of labile protons on the diamagnetic CEST (diaCEST) agent in order to perturb their signal, with this signal change then transferred to water via a dynamic exchange process between these labile protons and bulk water (see e.g., van Zijl, *Proc. Natl. Acad. Sci.* (2007)). Because a number of common metabolites possess labile protons, there can be challenges in discriminating the signal loss associated with the metabolite of interest and background (see e.g., Liu, et al., *NMR Biomed* (2013)), with most of the exchangeable protons on metabolites resonating between 1 to 3.6 ppm from water. Recently, iopamidol, a computed tomography (CT) agent approved for clinical use, was reported to produce strong CEST contrast at shifts that are further from water, from 4.2 to 5.5 ppm (see e.g., Haris, et al., *Neurosci. Meth.* (2013)).

The presently disclosed subject matter features compositions and methods for CEST MRI that are useful for a variety of in vivo imaging applications such as, for example, imaging soft tissues (e.g., tendons, ligaments, fascia, skin, fibrous tissues, fat, synovial membranes, muscles, nerves, blood vessels, etc.), the brain, pathologies, cancers, and the like. In particular, the presently disclosed subject matter provides organic CEST MRI contrast agents capable of producing strong CEST contrast at shifts that are greater than, for example, 5.5 ppm.

The present presently disclosed subject matter is based, at least in part, on the unexpected discovery that salicylic acid (1), one of the main metabolites of aspirin, possesses a suitable exchangeable proton that resonates 9.3 ppm from water, a frequency far removed from all other organic diaCEST agents reported to date. It has also been discovered that salicylic acid analogs produce similar CEST contrast to salicylic acid 1. For example, at least seven salicylic acid analogs (4-10) have been discovered to produce similar CEST contrast to 1, with chemical shifts that range from about 6.0 ppm to about 12 ppm from water.

The presently disclosed subject matter further provides beta-hydroxycarboxylate and beta-aminocarboxylate derivatives including, but not limited to, salicylic acid, salicylates, salicylic acid prodrugs, N-alkyl/aryl/acyl/sulfonyl-anthranilic acid analogs, and any aromatic compound with OH/NH group ortho to the carboxylic acid are general types of MRI organic contrast agents that produce significantly improved contrast in MR images detectable through CEST or frequency labeled exchange (FLEX) imaging. The agents may be used for various purposes including, but not limited to, tumor detection, MRI visualization of nanoparticles, receptor imaging, MRI sensing the concentration of cations, MR imaging of metabolic changes, MR visualization of transplanted cells, and the like.

The presently disclosed subject matter further provides improved CEST MRI organic contrast agents capable of producing strong CEST contrast at shifts that may range from about 8.7 ppm to about 10.8 ppm. In particular, the presently disclosed subject matter provides improved CEST MRI organic contrast agents capable of producing strong CEST contrast at shifts that may occur at about 6.0 ppm, about 6.5 ppm, about 7.0 ppm, about 7.5 ppm, about 8.0 ppm, about 8.5 ppm, about 9.0 ppm, about 9.5 ppm, about 10.0 ppm, about 10.5 ppm, about 11.0 ppm, about 11.5 ppm, about 12.0 ppm, about 12.5 ppm, about 13.0 ppm, about 13.5 ppm, about 14.0 ppm, about 14.5 ppm, or about 15.0 ppm. The presently disclosed subject matter further provides improved CEST MRI organic contrast agents capable of producing strong CEST contrast at shifts that may occur at about 8.7 ppm, 8.9 ppm, 9.3 ppm, 9.6 ppm, or 10.8 ppm.

The presently disclosed subject matter also provides: salicylic acid and N-alkyl/aryl/acyl/sulfonyl-anthranilic acid with improved CEST contrast properties; salicylic acid analogs and anthranilic acid derivatives with aromatic OH/NH group ortho to the carboxylic acid group with improved CEST contrast properties; methods of cation sensing using salicylic acid analogs and anthranilic acid derivatives; methods of in vivo imaging using salicylic acid analogs and anthranilic acid derivatives; and methods of improving MR image quality using drug and prodrugs of salicylic acid and anthranilic acid.

The presently disclosed subject matter further provides MRI contrast agents that may be used for various clinical or non-clinical purposes. Compared with paraCEST contrast agents, organic CEST contrast agents of the presently disclosed subject matter have many advantages such as, for example, lower toxicity due to the absence of lanthanide metals, ease of modification, and clearance through breakdown during natural biochemical processes. This is in sharp contrast to convention organic CEST agents, which suffer from sensitivity drawbacks, especially due to a small chemical shift difference between exchangeable proton and water. According to the presently disclosed subject matter, the contrast agents disclosed herein produce significantly improved contrast in MR images through CEST or FLEX imaging.

More particularly, in some embodiments, the presently disclosed subject matter provides a method of producing a magnetic resonance (MR) image of a target, comprising: introducing a magnetic resonance imaging (MRI) contrast agent to the target; and imaging the target using a Chemical Exchange Saturation Transfer (CEST) or frequency labeled exchange (FLEX) based MRI technique to produce the MR image of the target, wherein the MRI contrast agent is a compound of Formula (I), or a salt or stereoisomer thereof:

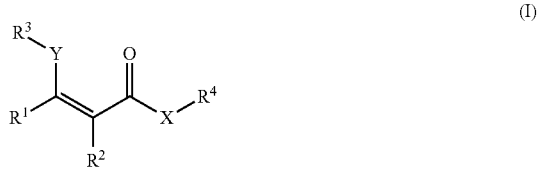

(I)

wherein:

$R^1$ and $R^2$ are each independently H, SR, phosphorus, alkyl, amino, alkoxyl, cycloalkyl, arylalkyl, cycloalkylalkyl, heterocyclic, heteroaryl-alkyl, aryl, heteroaryl, —C(O)-alkyl, or —C(O)O-alkyl; or $R^1$, and $R^2$, taken together with the bonds they are attached to, form an aryl or heteroaryl group; wherein said amino, alkyl, alkoxyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted;

when Y is O, $R^3$ is H, and when Y is $NR^5$, $R^3$ is selected from the group consisting of H, phosphorus, alkyl, —S(O)$_2$R, cycloalkyl, arylalkyl, cycloalkyl-alkyl, heterocyclic, heteroaryl-alkyl, aryl, heteroaryl, —C(O)-alkyl, or —C(O)O-alkyl, wherein said alkyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted, provided that at least one of $R^3$ and $R^5$ is H;

$R^4$ is H, phosphorus, halogen, SR, hydroxyl, amino, alkoxyl, alkyl, cycloalkyl, arylalkyl, cycloalkyl-alkyl, heterocyclic, heteroaryl-alkyl, aryl, heteroaryl, —C(O)— alkyl, or —C(O)O-alkyl, wherein said alkyl, amino, alkoxyl, cycloalkyl, arylalkyl, cycloalkyl-alkyl, heterocyclic, heteroaryl-alkyl, aryl, heteroaryl, —C(O)-alkyl, —C(O)O— alkyl moiety is optionally substituted; and X is O, $NR^5$, alkyl, or S;

Y is O or $NR^5$; and wherein each $R^5$ is independently selected from the group consisting of H, alkyl, cycloalkyl, arylalkyl, cycloalkyl-alkyl, heterocyclic, heteroaryl-alkyl, aryl, heteroaryl, —C(O)-alkyl, or —C(O)O-alkyl, wherein said alkyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted.

In particular embodiments, the compound of formula (I) is selected from the group consisting of:

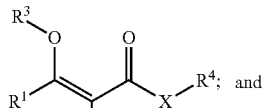
(Ia)

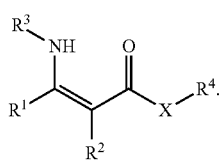
(Ib)

In more particular embodiments, the compound of formula (Ib) is selected from the group consisting of:

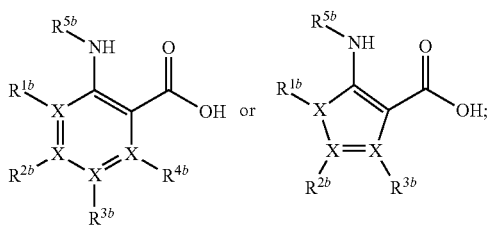

wherein:

$R^{1b}$, $R^{2b}$, and $R^{3b}$, independently, are absent, H, amino, alkoxyl, phosphorus, halogen, alkyl, alkyl-S—, cycloalkyl, arylalkyl, cycloalkyl-alkyl, heterocyclic, heteroaryl-alkyl, hydroxyl, aryl, heteroaryl, —C(O)-alkyl, or —C(O)O-alkyl, wherein said alkyl, amino, alkoxyl, alkyl-S—, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted;

$R^{4b}$ is H, phosphorus, halogen, amino, alkoxyl, alkyl, alkyl-S—, cycloalkyl, arylalkyl, cycloalkyl-alkyl, heterocyclic, heteroaryl-alkyl, hydroxyl, aryl, heteroaryl, —C(O)-alkyl, or —C(O)O-alkyl, wherein said alkyl, amino, alkoxyl, alkyl-S—, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted;

$R^{5b}$ is H, —S(O)$_2$—$R^{6b}$, alkyl, alkyl, cycloalkyl, arylalkyl, cycloalkyl-alkyl, heterocyclic, heteroaryl-alkyl, aryl, heteroaryl, —C(O)-alkyl, or —C(O)O-alkyl, wherein said alkyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted;

$R^{6b}$ is H, amino, halogen, alkyl, cycloalkyl, arylalkyl, cycloalkyl-alkyl, heterocyclic, heteroaryl-alkyl, aryl, heteroaryl, —C(O)-alkyl, or —C(O)O-alkyl, wherein said amino, alkyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted;

each X is independently C, NR, O, or S; and

R is H, alkyl, cycloalkyl, arylalkyl, cycloalkyl-alkyl, heterocyclic, heteroaryl-alkyl, aryl, heteroaryl, or —C(O)-alkyl, wherein said alkyl, cycloalkyl, arylalkyl, cycloalkyl-alkyl, heterocyclic, heteroaryl-alkyl, aryl, heteroaryl, or —C(O)-alkyl moiety is optionally substituted.

In yet more particular embodiments, the compound of formula (Ia) or (Ib) is selected from the group consisting of:

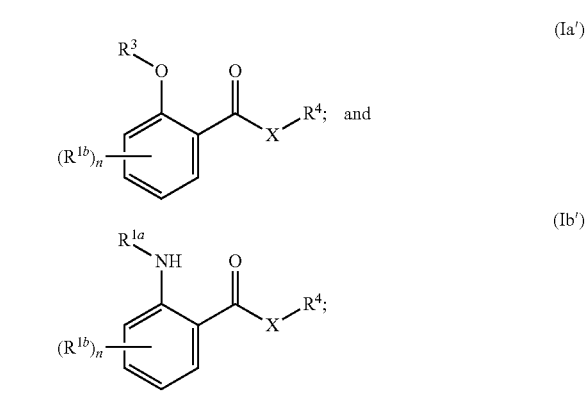

wherein:

each n is independently an integer selected from the group consisting of 0, 1, 2, 3, and 4;

each $R^{1b}$ is independently selected from the group consisting of hydrogen, substituted or unsubstituted alkyl, alkoxyl, hydroxyl, hydroxyalkyl, carboxyl, acyl, carbonyl, carbamoyl, alkylcarbamoyl, halogen, amino, nitro, nitrile, amide, haloalkyl, aryl, cycloalkyl, aralkyloxyl, and —SO$_3$H.

In particular embodiments, the compound is selected from the group of compounds and analogs or derivatives thereof presented in Tables 2A-3A and Tables 1-6, herein below.

The compounds of the presently disclosed subject matter can be prepared according to a variety of methods, which are known to one of ordinary skill in the art. Methods for optimizing reaction conditions, if necessary minimizing competing by-products, are also known in the art. The methods may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

In general, the compounds of the presently disclosed subject matter possess excellent CEST contrast properties. Thus, the compounds of the presently disclosed subject matter are useful as MRI contrast agents. In particular, compounds of the presently disclosed subject matter can be used for various purposes including but not limited to determining intratumoral pH, determining encapsulated cell pH, determining kidney pH, monitoring the delivery of chemotherapeutics, targeted imaging studies through conjugation of a receptor ligand or an antigen, tumor detection, MRI visualization of nanoparticles, receptor imaging, MRI sensing the concentration of cations, MR imaging of metabolic changes, MR visualization of transplanted cells, sensing the presence of enzymes, and the like.

The methods of the presently disclosed subject matter are useful for detecting, sensing, or imaging various types of material (e.g., enzymes, vitamins, ligands, tissues, metal ions, organic substrates, and biologically active chemical elements).

The methods of the presently disclosed subject matter are also useful for diagnosing, based on an MR image of a target in a subject, whether the subject may have a particular disease (e.g., cancer, diabetes and epilepsy, infectious diseases, neoplasms, endocrine, nutritional, and metabolic diseases, diseases of the blood and blood-forming organs, inflammatory diseases, immune diseases, including autoimmune diseases, diseases of the nervous system, diseases of the circulatory system, diseases of the respiratory system, diseases of the digestive system, diseases of the skin, diseases of the musculoskeletal system, and the like). The methods also allow monitoring, based on an MR image of a target in a subject, progression or regression of a disease or disorder in the subject.

Also provided is a method of identifying a compound useful as a MRI contrast agent, which includes a step of screening the compound for its CEST properties. In certain embodiments, the compound is a beta-hydroxycarboxylate and beta-aminocarboxylate derivatives including, but not limited to, salicylic acid, salicylates, salicylic acid prodrugs, N-alkyl/aryl/acyl/sulfonyl-anthranilic acid analogs, and any aromatic compound with OH/NH group ortho to the carboxylic acid.

The presently disclosed subject matter also includes a method of designing and/or preparing (e.g., synthesizing) compounds that are useful as MRI contrast agents. The method comprises one or more following steps: evaluating the structures of existing MRI contrast agents for their CEST contrast properties, designing and synthesizing new compounds, and screening the new compounds for their CEST contrast properties.

The CEST approach of the presently disclosed subject matter can be further extended to designing other novel responsive agents for molecular and cellular MRI applications. Any potential novel responsive agents may be assessed by an optical assay (using multi-well plates) for their potentiality for the CEST approach.

Certain design criteria for creating MRI contrast agents can be found in Que et al. (Chem Soc. Rev. 2010, 39, 51-60) and Hyman et al. (Coordination Chemistry Reviews, 256 (2012), 2333-2356).

Further featured are methods that embody the use of the MRI contrast agents of the presently disclosed subject matter.

By "making an image", it is meant using a presently disclosed method, such as a method that is magnetic resonance (MR)-based (magnets that polarize and excite hydrogen nuclei in water molecules in tissue to produce a detectable signal) to form an image of a cell, tissue, tumor, part of body, and the like.

In some embodiments, the tumor or cell is found in a subject. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments, the subject is human. In other embodiments, the subject is non-human.

In some embodiments, a detectably effective amount of the imaging agent of the presently disclosed methods is administered to a subject. In accordance with the presently disclosed subject matter, "a detectably effective amount" of the imaging agent is defined as an amount sufficient to yield an acceptable image using equipment which is available for clinical use. A detectably effective amount of the imaging agent may be administered in more than one injection. The detectably effective amount of the imaging agent can vary according to factors such as the degree of susceptibility of the individual, the age, sex, and weight of the individual, idiosyncratic responses of the individual, the dosimetry, and instrument and film-related factors. Optimization of such factors is well within the level of skill in the art.

It is preferable to have the compound comprising the imaging agent to localize to the tumor or cell quickly after administration so as to minimize any side effects to the subject. Accordingly, in some embodiments, the compound comprising the imaging agent substantially localizes to the tumor or cell within about 60 minutes of administration. In other embodiments, the compound comprising the imaging agent substantially localizes to the tumor or cell within about 30 minutes of administration. In still other embodiments, the compound comprising the imaging agent substantially localizes to the tumor or cell within about 10 minutes of administration.

It is also preferable that the compounds of the presently disclosed subject matter are excreted from tissues of the body quickly to prevent prolonged exposure to the radiation of the radiolabeled compound administered to the patient. Typically compounds of the presently disclosed subject matter are eliminated from the body in less than about 24 hours. More preferably, compounds of the presently disclosed subject matter are eliminated from the body in less than about 16 hours, 12 hours, 8 hours, 6 hours, 4 hours, 2 hours, 90 minutes, or 60 minutes.

In some embodiments, the presently disclosed methods comprise clearance of the compound comprising the imaging agent from the tumor or cell in the subject. At least one advantage of the presently disclosed methods is that, in some embodiments, there is more rapid clearance of the compound comprising the imaging agent from the kidneys than from the tumor of the subject.

In some embodiments, the presently disclosed methods use compounds that are stable in vivo such that substantially all, e.g., more than about 50%, 60%, 70%, 80%, or more preferably 90% of the injected compound is not metabolized by the body prior to excretion. In other embodiments, the compound comprising the imaging agent is stable in vivo.

B. Magnetic Resonance Imaging System

The presently disclosed subject matter also features a magnetic resonance imaging system. Magnetic resonance imaging systems are known in the art and commercially available. In certain aspects, the magnetic resonance imaging system comprises an imaging apparatus configured to perform a CEST or FLEX MR technique using one or more compounds as described herein.

C. Kits

Kits are also provided herein. For example, in certain aspects, the presently disclosed subject matter features kits for MRI imaging comprising one or more compounds as described herein, and instructions for use.

The kits may also provide means for administering the compounds (e.g., beta-hydroxycarboxylate and beta-aminocarboxylate derivatives including, but not limited to, salicylic acid, salicylates, salicylic acid prodrugs, N-alkyl/aryl/acyl/sulfonyl-anthranilic acid analogs, and any aromatic compound with OH/NH group ortho to the carboxylic acid), by, for example, syringes. The kits may also provide buffers, pharmaceutically suitable carriers and the like. The instructions may provide information, for example, regarding storage, use, subject selection, administration, and the like.

D. Definitions i. Chemical Definitions

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

As used herein, where an internal substituent is flanked by bonds (for example, —NRC(O)—) the order of the atoms is fixed, the orientation of the group may not be reversed, and is inserted into a structure in the orientation presented. In other words —NRC(O)— is not the same as —C(O)NR—. As used herein the term C(O) (for example —NRC(O)—) is used to indicate a carbonyl (C=O) group, where the oxygen is bonded to the carbon by a double bond.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

In certain embodiments, alkyl groups are $C_1$-$C_6$ alkyl groups or $C_1$-$C_4$ alkyl groups. The term "$C_1$-$C_6$ alkyl" as used herein means straight-chain, branched, or cyclic $C_1$-$C_6$ hydrocarbons which are completely saturated and hybrids thereof, such as (cycloalkyl)alkyl. Examples of $C_1$-$C_6$ alkyl substituents include methyl (Me), ethyl (Et), propyl (including n-propyl (n-Pr, $^n$Pr), iso-propyl (i-Pr, $^i$Pr), and cyclopropyl (c-Pr, $^0$Pr)), butyl (including n-butyl (n-Bu, $^n$Bu), iso-butyl (i-Bu, $^i$Bu), sec-butyl (s-Bu, $^s$Bu), tert-butyl (t-Bu, $^t$Bu), or cyclobutyl (c-Bu, $^0$Bu)), and so forth.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

In the term "(cycloalkyl)alkyl", cycloalkyl, and alkyl are as defined above, and the point of attachment is on the alkyl group. This term encompasses, but is not limited to, cyclopropylmethyl, cyclopentylmethyl, and cyclohexylmethyl. The alkyl group may be substituted or unsubstituted.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopropyl, cyclobutyl, cyclopentyl, cyclohexyl, and cycloheptyl.

Multicyclic cycloalkyl rings include adamantyl, octahydronaphthyl, decalin, camphor, camphane, and noradamantyl, and fused ring systems, such as dihydro- and tetrahydronaphthalene, and the like.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —CH$_2$CH$_2$CH$_2$CH$_2$—, —CH$_2$CH=CHCH$_2$—, —CH$_2$CsCCH$_2$—, —CH$_2$CH$_2$CH (CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently.

The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, indazolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). The term "haloaryl," however, as used herein, is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

As used herein, the term "alkylaryl" includes alkyl groups, as defined above, substituted by aryl groups, as defined above. The aryl group may be connected at any point on the alkyl group. The term $C_4$-$C_{16}$ alkylaryl includes alkylaryl groups having a total of 4 to 16 carbon atoms, counting the carbon atoms on the alkyl group and aryl group together. Examples of alkylaryl groups include but are not limited to benzyl (phenylmethyl), phenyl ethyl, and naphthylmethyl. The alkylaryl group may be substituted or unsubstituted. Substituents are not counted towards the total number of atoms in the alkylaryl group, so long as the total atoms in the substituent(s) are not larger than the alkylaryl group.

Further, a structure represented generally by the formula:

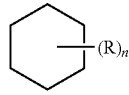

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

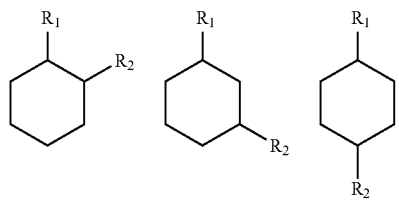

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

A substituent bearing a broken bond, such as the example shown below, means that the substituent is directly bonded to the molecule at the indicated position. No additional methylene ($CH_2$) groups are implied. The symbol (∿∿∿∿) denotes the point of attachment of a moiety to the remainder of the molecule.

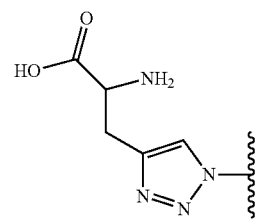 [SMILES: *n1cc(CC(N)C(=O)O)nn1]

Substituents bearing two broken bonds, such as the example shown below, means that the orientation of the atoms is as-indicated, left to right and should be inserted into a molecule in the orientation shown. No additional methylene ($CH_2$) groups are implied unless specifically indicated.

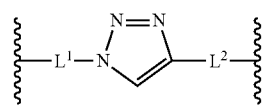

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxyl or thioalkoxy groups, or arylalkyl groups. As used herein, an "alkoxyl" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxy l" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R''', wherein R', R", and R''' are each independently selected from the group consisting of alkyl groups. Additionally, R', R", and/or R''' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like also can be present in the compounds described herein, and all such stable isomers are contemplated in the presently disclosed subject matter. Cis and trans geometric isomers of the compounds of the presently disclosed subject matter are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated. In certain embodiments, the salt or counter-ion may be pharmaceutically acceptable, for administration to a subject. Pharmaceutically acceptable salts are discussed later.

As used herein, a "protecting group" is a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Specific examples of protecting groups include but are not limited to, benzyl, p-methoxybenzyl (PMB), tertiary butyl ('Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

ii. Pharmaceutical Salts

The compounds of the present disclosure may exist as pharmaceutically acceptable salts. The term "pharmaceutically acceptable salts" is meant to include salts of active compounds which are prepared with relatively nontoxic acids or bases, depending on the particular substituent moieties found on the compounds described herein. Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrates, (e.g. (+)-tartrates, (−)-tartrates or mixtures thereof including racemic mixtures), or teoclate. These salts may be prepared by methods known to those skilled in art. Other pharmaceutically acceptable salts may be found in, for example, Remington: The Science and Practice of Pharmacy (20th ed.) Lippincott, Williams & Wilkins (2000).

Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like.

Also included are salts of amino acids such as arginate and the like, and salts of organic acids like glucuronic or galactunoric acids and the like, see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts. The neutral forms of the compounds may be regenerated by contacting the salt with a base or acid and isolating the parent compound in the conventional manner.

The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

iii. Pharmaceutical Compositions and Kits

The compounds disclosed herein can be formulated into various compositions, for use in diagnostic, imaging or therapeutic treatment methods. The compositions (e.g. pharmaceutical compositions) can be assembled as a kit. Generally, a pharmaceutical composition comprises an effective amount (e.g., a pharmaceutically effective amount, or detectably effective amount) of a compound described above.

A presently disclosed composition can be formulated as a pharmaceutical composition, which comprises a presently disclosed compound and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, $18^1$ ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

A pharmaceutical composition or kit of the presently disclosed subject matter can contain other pharmaceuticals, in addition to the compound. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the presently disclosed subject matter.

One skilled in the art will appreciate that a suitable or appropriate formulation can be selected, adapted or developed based upon the particular application at hand. Dosages for presently disclosed compositions can be in unit dosage form. The term "unit dosage form" as used herein refers to physically discrete units suitable as unitary dosages for animal (e.g. human) subjects, each unit containing a predetermined quantity of a presently disclosed agent, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient.

The dose of a presently disclosed composition, administered to an animal, particularly a human, in the context of the presently disclosed subject matter should be sufficient to produce at least a detectable amount of a diagnostic or therapeutic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, and the like. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Other embodiments provide kits including a compound according to the presently disclosed subject matter. In certain embodiments, the kit provides packaged pharmaceutical compositions having a pharmaceutically acceptable carrier and a compound of the presently disclosed subject matter. In some embodiments the packaged pharmaceutical composition will include the reaction precursors necessary to generate the compound of the presently disclosed subject matter upon combination with a radionuclide. Other packaged pharmaceutical compositions provided by the presently disclosed subject matter further comprise indicia comprising at least one of: instructions for preparing compounds according to the presently disclosed subject matter from supplied precursors, instructions for using the composition to image cells or tissues expressing PSMA, or instructions for using the composition to image glutamatergic neurotransmission in a patient suffering from a stress-related disorder, or instructions for using the composition to image prostate cancer.

In certain embodiments, a kit according to the presently disclosed subject matter contains an agent described above in combination with a pharmaceutically acceptable carrier. The agent and carrier may be provided in solution or in lyophilized form. When the agent and carrier of the kit are in lyophilized form, the kit may optionally contain a sterile and physiologically acceptable reconstitution medium such as water, saline, buffered saline, and the like. The kit may provide a compound of the presently disclosed subject matter in solution or in lyophilized form, and these components of the kit of the presently disclosed subject matter may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

Determination and optimization of such stabilizers and stabilization methods are well within the level of skill in the art.

A "pharmaceutically acceptable carrier" refers to a biocompatible solution, having due regard to sterility, p[Eta], isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier also can contain stabilizers, preservatives, antioxidants, or other additives, which are well known to one of skill in the art, or other vehicles as known in the art.

iv. General Definitions

Although specific terms are employed herein, they are used in a generic and descriptive sense only and not for purposes of limitation. Particular definitions are provided herein for clarity. Unless otherwise defined, all technical and scientific terms used herein have the same meaning as commonly understood by one of ordinary skill in the art to which this presently described subject matter belongs.

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells.

The term "therapeutic agent" refers to a non-peptide, small molecule compound that has the potential of affecting the function of an organism. A therapeutic agent may decrease, suppress, attenuate, diminish, arrest, or stabilize the development or progression of disease, disorder, or condition in a host organism or subject.

By "modifies" is meant alters. An agent that modifies a cell, substrate, or cellular environment produces a biochemical alteration in a component (e.g., polypeptide, nucleotide, or molecular component) of the cell, substrate, or cellular environment.

By "control" is meant a standard or reference condition.

By "disease" is meant any condition or disorder that damages or interferes with the normal function of a cell, tissue, organ, organism, or subject.

An "effective amount" of an agent refers to the amount of the agent sufficient to elicit a desired biological response or a measurable difference when compared to a control. As will be appreciated by one of ordinary skill in the art, the absolute amount of a particular agent that is effective for treating a disease, disorder, condition, or injury can vary depending on such factors as the agent to be delivered, the manner of administration, the age, body weight, and general health of the subject, the desired biological endpoint, the desired therapeutic effect, and the like. Ultimately, an attending clinician will decide the appropriate amount and dosage regimen. For example, an "effective amount" of an agent can be an amount sufficient to produce a measurable image when the compound is used for imaging, or an amount sufficient to ameliorate the symptoms of a disease when the compound is used for therapy. One of ordinary skill in the art will further understand that an effective amount of an agent can be administered in a single dose, or can be achieved by administration of multiple doses.

As used herein, the terms "treat," "treating," "treatment," and the like, are used interchangeably and are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy, and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

Further, as used herein, the term "inhibit" or "inhibits" means to decrease, suppress, attenuate, diminish, arrest, or stabilize the development or progression of a disease, disorder, or condition, or the activity of a biological pathway, e.g., by at least 10%, 20%, 30%, 40%, 50%, 60%, 70%, 80%, 90%, 95%, 98%, 99%, or even 100% compared to an untreated control subject, cell, or biological pathway. By the term "decrease" is meant to inhibit, suppress, attenuate, diminish, arrest, or stabilize a symptom of a disease, disorder, or condition. It will be appreciated that, although not precluded, treating a disease, disorder or condition does not require that the disease, disorder, condition or symptoms associated therewith be completely eliminated.

The term "administering" as used herein refers to contacting a subject with a presently disclosed agent.

By "therapeutic delivery device" is meant any device that provides for the release of a therapeutic agent. Exemplary therapeutic delivery devices include tablets and pills, described below, as well as syringes, osmotic pumps, indwelling catheters, delayed-release and sustained-release biomaterials.

In certain embodiments, presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising the presently disclosed compounds. Alternatively, these agents may be part of a single dosage form, mixed together with one or more presently disclosed compounds in a single composition.

By "in combination with" is meant the administration of one or more presently disclosed compounds with one or more therapeutic agents either simultaneously, sequentially, or a combination thereof. Therefore, a cell or a subject can receive one or more presently disclosed compounds and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the one or more presently disclosed compounds and one or more therapeutic agents are administered simultaneously, they can be administered to the cell or administered to the subject as separate pharmaceutical compositions, each comprising either one or more presently disclosed compounds or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

"Administering or introducing" is defined herein as a means of providing an agent or a composition containing the agent to a subject in a manner that results in the agent being inside the subject's body. Such an administration can be by any route including, without limitation, oral, transdermal (e.g., vagina, rectum, oral mucosa), by injection (e.g., subcutaneous, intravenous, parenterally, intraperitoneally, intrathecal, intraocular), by inhalation (e.g., oral or nasal), or topical (e.g., eye drops, cream, etc.). Pharmaceutical preparations are, of course, given by forms suitable for each administration route.

"Contacting" means any action which results in at least one compound comprising the imaging agent of the presently disclosed subject matter physically contacting at least one PSMA-expressing tumor or cell. Contacting can include exposing the cell(s) or tumor(s) to the compound in an amount sufficient to result in contact of at least one compound with at least one cell or tumor. The method can be practiced in vitro or ex vivo by introducing, and preferably mixing, the compound and cell(s) or tumor(s) in a controlled environment, such as a culture dish or tube. The method can be practiced in vivo, in which case contacting means exposing at least one cell or tumor in a subject to at least one compound of the presently disclosed subject matter, such as administering the compound to a subject via any suitable route. According to the presently disclosed subject matter, contacting may comprise introducing, exposing, and the like, the compound at a site distant to the cells to be contacted, and allowing the bodily functions of the subject, or natural (e.g., diffusion) or man-induced (e.g., swirling) movements of fluids to result in contact of the compound and cell(s) or tumor(s). In some embodiments, the tumor or cell is found in vitro, in vivo, or ex vivo.

By "agent" is meant any chemical compound, small molecule chemical compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes a 1%, 5%, 10%, 15%, 20%, etc. change in expression levels, preferably a 25% change, more preferably a 40% change, and most preferably a 50% or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding.

The term "cell or eukaryotic cell" is meant to refer to cells from an organism whose cells contain complex structures enclosed within membranes.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

The term "magnetic resonance imaging (MRI)" is meant to refer to a noninvasive diagnostic process that uses an MR scanner to obtain images of objects, tissues, or bodies. An MR scanner uses nuclear magnetic resonance to obtain images. The MR scanner may include, for example, (1) a body-encircling magnet that generates a strong, uniform magnetic field which interacts with radio waves to excite the nuclei of specific atoms, such as hydrogen, and (2) a detector that detects relaxation of the nuclei and transforms the detected signals into a visual image.

By "marker" is meant any protein or polynucleotide having an alteration in expression level or activity that is associated with a disease.

As used herein, "obtaining" as in "obtaining an agent" includes synthesizing, purchasing, or otherwise acquiring the agent.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

By "reference" is meant a standard or control condition.

By "subject" is meant a mammal, including, but not limited to, a human or non-human mammal, such as a bovine, equine, canine, ovine, or feline.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Salicylic Acid Produces a Much Larger Chemical Shift at a Relatively Low Saturation Field Strength Relative to Conventional Organic Contrast Agents Conventional organic compounds the display CEST contrast include, for example, Barbituric Acid and D-Glucose. These conventional organic compounds display CEST contrast that ranges from 1 ppm to 6 ppm (see e.g, Caravan, *Chem. Soc. Rev.* (2006)). As shown in FIG. 1, the $MTR_{asym}$ spectra of compounds 1, 2, and 3 were compared at the same scale. The phenol proton in compound 1 (salicylic acid) possessed a much larger chemical shift at a relatively low saturation field strength ( )=3.6 µT. The maximum CEST contrast occurred at 9.3 ppm from water. Without being bound by theory, it is believed that at neutral pH the deprotonated carboxylic anion forms a strong hydrogen bond to the phenol proton, which results in this dramatic shift. The signal of compound 1 dropped greatly at either lower pH (<6), when a significant amount of the carboxylate becomes protonated, or at higher pH (>11) when the phenol proton becomes deprotonated.

Example 2

Salicylic Acid has Beneficial Properties for Use as a CEST Contrast Agent

Several CEST properties of compound 1 were measured in vitro. For example, FIG. 2A displays a Z-spectrum and $MTR_{asym}$ spectrum for salicylic acid (compound 1). The proton exchange rate ($k_{sw}$) with water for compound 1 was measured as a function of pH using the QUESP experiment (see e.g., McMahon, et al., *Magn. Reson. Med.* (2006)), with the data shown in FIGS. 2B and 2C. Compound 1 has a $k_{sw}$=1.2 ks$^{-1}$ at 25 mM, pH 7.0, and as seen in FIG. 2B, the $k_{sw}$ is strongly dependent on the pH. Above pH 6.0, $k_{sw}$ is below the chemical shift difference at 11.7 T ($\Delta\omega$=4,650 Hz) placing the rates in the slow exchange NMR regime and making this agent well suited for CEST imaging. As can also be seen, for pH 7.0, maximum contrast was produced by $\omega_1$=10.8 μT, although in practice using 7.2 μT or higher would produce similar results. The use of these saturation conditions resulted in CEST contrast=4% at 1.5 mM concentration (see e.g., FIG. 2D-2E). These data indicate that salicylic acid has an excellent sensitivity, especially considering in vivo tissue background.

Salicylic acid (1) was dissolved in 0.01 M PBS with 10% deuterium oxide at the concentration of 25 mM and titrated with HCl/NaOH to pH 7.0. The $^1$H-NMR was acquired on a 500M Bruker NMR spectrometer at room temperature. The spectra and proton assignment are shown in FIG. 2F. The $C_2$—OH exchangeable proton was clearly observed at chemical shift 14 ppm from TMS.

The effect of pH on the contrast of salicylic acid (1) was tested at a concentration of 25 mM, $\omega$1=7.2 μT. The Z-spectra and $MTR_{asym}$ of pH 5.8, 6.5, 6.8, 7.2, 7.6, 8.1, 11.7 were collected and shown in FIG. 2G. Maximal contrast was observed between pH 6.5 and 7.0.

Additionally, the concentration dependence of the contrast of salicylic acid (1) at pH 7.3-7.4 was measured at a saturation field strength ($\omega$1)=7.2 μT. As shown in FIG. 2H, the Z-spectra and $MTR_{asym}$ spectra at concentrations 1.5 mM, 3.1 mM, 6.3 mM, 12.5 mM, 25.0 mM and 50.0 mM were collected and are shown below. 4% contrast was obtained at 1.50 mM.

The proton exchange rate of salicylic acid (1) was calculated at different pH. QUESP datasets for salicylic acid (1) at 9.3 ppm were collected as a function of pH using $\omega$1=1.2 μT, 2.4 μT, 3.6 μT, 5.4 μT, 7.2 μT, 10.8 μT and 11.4 μT. The solvent to water exchange rate ($k_{sw}$) was calculated according to fitting to a 2-pool Bloch equation model. The parameters for all fitting were: R1w=0.3, R2w=0.6, R1s=0.71, R2s=39, Tsat=3s. The results at pH 5.8, 6.2, 6.5, 7.0, 7.4 and 7.8 are summarized in FIG. 23, which shows the calculated proton exchange rate of salicylic acid (1) at different pH.

Example 3

Salicylic Acid Analogs Also Produce a Much Larger Chemical Shift Relative to Conventional Organic Contrast Agents As shown in FIG. 3, eight analogs of compound 1 were also tested to determine how electronic effects related to the phenol ring would modify this contrast. Placing an OH or NH2 group (4 or 7) at the para position to the phenol C2-OH reduced the chemical shift to 8.7 ppm, which could be slightly increased to 9.6 ppm by attaching an OH or NH2 group (5 or 8) at the $C_4$ position of the salicylic acid. Surprisingly, in the case of 2,6-dihydroxybenzoic acid (6) the contrast dropped dramatically, although the chemical shift remained close. A more interesting result was obtained with 1-hydroxy-2-naphthoic acid (10). The more polarizable naphthene ring helped to shift the CEST pick signal further to 10.8 ppm. Anthranilic acid (11), the substitution of an NH2 for the OH adjacent to the carboxylic acid, did not show any contrast.

As seen in FIGS. 1-3, these analogs possess exchangeable protons with the furthest reported shifts for organic CEST agents. While these protons are not as shifted as the 45 to 52 ppm found for bound water in paramagnetic Eu$^{3+}$ complexes (see e.g., Mani, et al., *Contrast Media Mol. Imaging* (2009)) or the −600 ppm found in paramagnetic Tb$^{3+}$ complexes (see e.g., Aime, et al., *Angew. Chem. Int. Ed.* (2005)), the exchange rates are slow enough relative to the chemical shift difference with water to not produce significant exchange based $T_2$ relaxation, which can darken pixels containing CEST agents (see e.g., Reference 17). The saturation field strengths shown in FIG. 2B can be generated in many imaging coils, making these analogs suitable diaCEST agents. The shifts are approaching, but not quite as large, as those seen for the carbamate protons that generate CEST contrast on Yb$^{3+}$ agents (~−16 ppm; see e.g., Chauvin, et al., *Angew. Chem. Int. Ed.* (2008)), osmotic stressed lipoCEST agents based on Tm$^{3+}$ complexes (~18 ppm) or Dy$^{3+}$ complexes (~45 ppm; see e.g., Terreno, et al., *Angew. Chem. Int. Ed.* (2007)), and larger than the spherical lipoCEST preparations (see e.g., Aime, et al., *Angew. Chem. Int. Ed.* (2005)). In addition, as is shown in FIG. 3, the salicylic acid scaffold can tolerate chemical modification, thereby allowing the conjugation of this type of probe to polymers (see e.g., Ali, et al., *Nanomedicine* (2012)), nanoparticles (see e.g., Winter, et al., *Magn. Reson. Med.* (2006)), or hydrogels (see e.g., Chan, et al., *Nat. Mater.* (2013)), which are suitable for a variety of drug or cell based therapies.

FIG. 3B shows Z-spectra and $MTR_{asym}$ of salicylic acid analogs. 25 mM salicylic acid analogs (4-11) were made at pH 7.1-7.4 and tested with the phantom condition as described above. The Z-spectra were obtained by using Tsat=3 sec, $\omega$1=3.6 μT at 37° C. The Z-spectra, $MTR_{asym}$ and QUESP curve are listed in FIG. 3B.

Example 4

Salicylic Acid Functions as a CEST MRI Contrast Agent In Vivo

To evaluate whether compound 1 could be detected after administration into live animals, two mice were injected with 15 tM of Compound 1 and CEST images were collected. In particular, images consisting of a single axial slice containing both kidneys were collected. Because the $B_0$ inhomogeneity was less than 200 Hz for these animals, a two-point collection scheme was used to limit the scan time, which is also allowed by the use of the 7.2 μT field strength. A pronounced increase in the CEST contrast was observed at 9.3 ppm, which peaked in the kidneys 7 minutes after injection (FIGS. 4B-C), indicative of probe uptake. The average CEST contrast was 6.0±0.8% over the whole kidney (FIGS. 4B-C, E), with the contrast persisting for 8 minutes as displayed in FIG. 4E. The advantage of the large shift is evident from FIG. 4D, where the peak of compound 1 is far removed from the large $MTR_{asym}$ seen in the right kidney between 1-4.5 ppm, which is the chemical shift of many exchangeable protons seen on common metabolites such as glucose, creatine, L-glutamine, L-glutamate, GSH, and the like. In addition, the $S/S_0$=30% pre-injection at 9.3 ppm compared to $S/S_0$=23% at 5 ppm, an increase in signal strength of approximately 1/4.

As an initial test, 100 µl of 250 mM compound 1 solution was injected into the mouse tail vein (i.v.), and CEST images were acquired using a saturation field strength of 5.9 µT. A Z-spectrum was acquired before injection. For the dynamic CEST contrast measurements, a 6-offset scheme (±9.6 ppm, ±9.3 ppm, ±9.0 ppm, 5 min temporal resolution) was used after i.v. injection to ensure robustness to $B_0$ inhomogeneity and high contrast-noise-ratio. The CEST contrast map was calculated with averaging over the 3 offsets (9.6 ppm, 9.3 ppm and 9.0 ppm). The kidney reached maximum CEST contrast at around 5 min, and then the contrast started decaying at 10 min. The resulting Z-spectra are plotted in FIG. 4F, and the pre- and post-injection maps are shown in FIG. 4G.

According to the initial results in FIGS. 4F-4G, the in vivo data collection scheme was modified in order to improve the kinetic data for compound 1 in the kidney. In addition, the dose of the contrast agent was further reduced to 60 µl of 250 mM solution. Instead of time consuming 5.9 µT 6-offset, a 7.2 µT 2 offset at 9.3 ppm and −9.3 ppm was used for the dynamic CEST image acquisition. For the image post-processing, the CEST contrast maps at 9.3 ppm was smoothed by adding a 2×2 medium filter and overlapped to the saturation weighted image at −9.3 ppm. Images at every two adjacent time points were also averaged to increase the contrast-noise-ratio, with a temporal resolution of 3 min. For 2 mice, the dynamic contrast maps at 9.3 ppm are shown in FIG. 4H.

Additional data was also collected at 9.5 ppm, as shown in FIG. 4I. Specifically, in vivo CEST-MR images were acquired on a Bruker Biospec 11.7 T MR scanner. The BALB/c mice weighing 20-25 g (Charles River Laboratories Italia S.r.l., Calco Italia) were maintained under specific pathogen-free conditions in the animal facility of Johns Hopkins University. For MRI mice were anesthetized by 0.5-2% isoflurane and placed in a 23 mm mouse coil for both transmission and receiver. Breath rate was monitored throughout in vivo MRI experiments using a respiratory probe. A 100 µL volume of a 0.1 M beta hydroxy carboxylates solution in water (pH 7) was slowly injected via a catheter into the tail vein. CEST images of one axial slice were acquired at different time-points pre- and post-injection with a temporal resolution of 100 secs. The sequence is similar as in phantom study except a saturation field strength (B1) of 7.2 uT TR/TE=5 s/15 ms, matrix size=64×48, FOV=1.7-cm×2.05-mm and slice thickness of 1.5 mm. At each time point, 2 saturation-weighted images were acquired with saturation frequency at +9.5 ppm and −9.5 ppm from water, respectively. All data were processed using home-written scripts in MATLAB (Mathworks, Waltham, Mass.). CEST contrast was quantified by $MTR_{asym}=(S-\Delta\omega-S+\Delta\omega))/S-\Delta\omega$ and the contrast map was smoothed using 2×2 median filter and overlayed on the saturation-weighted image at −9.5 ppm at the same time point. A threshold was added to the CEST contrast map by filtering the voxels with signal-noise-ratio less than 40:1. An example map displaying CEST contrast in the kidney of a mouse by injecting salicylic acid is shown at FIG. 4I.

The magnitude of the contrast detected is similar to that shown previously for iopamidol, another diaCEST agent (see e.g., Longo, et al., *Magn. Reson. Med.* (2011)), with a difference in the optimal time to observe the contrast (7 min for 15 tM 1 vs 45 min for 48.5 tM iopamidol). In addition, simple continuous wave irradiation was chosen to detect compound 1 because of the robustness of this method. However more advanced saturation schemes such as SAFARI (see e.g., Scheidegger, et al., *Magn. Reson. Med.* (2011)), OPARACHEE (see e.g., Vinogradov, et al., *Magn. Reson. Med.* (2007)), FLEX (see e.g., Friedman, et al., *J. Am. Chem. Soc.* (2010)), CERT (see e.g., Zu, et al., *Magn. Reson. Med.* (2013)), two-frequency irradiation (see e.g., Lee, et al., *J. Chem. Phy.* (2011)) or LOVARS (see e.g., Song, et al., *Mag. Res. Med.* (2012)) may also be used to improve the detection of this contrast agent.

One of the attractive features of compound 1 and its analogs is the wealth of literature on the pharmacokinetics, formulation, and toxicity of this material. Compound 1 is a component of human diets and is found at elevated levels in the serum of vegetarians (see e.g., Paterson, et al., *J. Agr. Food Chem.* (2008); Blacklock, et al., *J. Clin. Pathol.* (2001)). It is also a well-known nonsteroidal anti-inflammatory drug (NSAID). The salts and esters of salicylic acid are known as salicylates, which have been administered to patients so that low millimolar concentrations are achieved in plasma for the treatment of rheumatoid arthritis (see e.g., McCarty, and Block, *Integr. Cancer. Ther.* (2006)). Aspirin, a prodrug of salicylic acid, was first isolated in 1897 and has subsequently been found to have beneficial effects in a variety of conditions including inflammation and cancer (see e.g., Walter, *Br. Med. J.* (2000)). Accordingly, the improved organic CEST contrast agents of the presently disclosed subject matter are expected to be directly translatable to human use on the basis of the widespread testing that has been performed on these and similar compounds in patients over many decades.

The presently disclosed subject matter provides salicylic acid (1) and its analogs (e.g., 4-10) as a new set of diaCEST probes with chemical shifts far downfield from conventional organic CEST agents. As a quick in vivo evaluation, compound 1 was injected into mice and 6% contrast was obtained in kidneys. This type of low-toxicity probe, especially compound 1, may improve sensitivity of the existing CEST method.

Example 5

Screening of Beta Hydroxy Carboxylates Analogs for CEST Contrast

All compounds were dissolved in 0.01M phosphate-buffered saline (PBS) with concentrations of 25 mM, and then titrated by HCl/NaOH to the pH of 6 to 8. The solutions were placed into 1 mm capillary tubes and then assembled in a holder for high throughput CEST MR imaging. CEST experiments were taken on a Bruker Biospec 11.7 T MR scanner, using a RARE sequence with CW saturation pulse length of 3 seconds and saturation field strength (B1) of 3.6 µT. The CEST Z-spectra were acquired by incrementing the saturation frequency every 0.3 ppm from −18 to 18 ppm for phantoms; TR=6 s, effective TE=15-19 ms, matrix size=96× 64. CEST contrast was quantified by $MTR_{asym}=(S-\Delta\omega-S+\Delta\omega))/S0$ after a voxel-by-voxel B0 correction, with characterized mean Z-spectra and $MTR_{asym}$ spectra for sample ROIs plotted and the typical results were summarized in FIG. 3A. Salicylic acid analogs were found to give the excellent CEST contrast with 50% or higher contrast observed at 9.3 ppm at 100 mM concentrations. Additionally, the above screening techniques identified other beta-aminocarboxylate derivatives that displayed beneficial CEST contrast, as summarized in FIG. 6.

Example 6

Methods and Materials

Phantom Preparation and Data Acquisition:

All compounds were purchased from Sigma Aldrich (St. Louis, Mo.). Samples were dissolved in 0.01 M phosphate-buffered saline (PBS) at concentrations from 1.5 mM to 100 mM, and titrated using high concentration HCl/NaOH to various pH values ranging from 6 to 8. The solutions were placed into 1 mm glass capillaries and assembled in a holder for CEST MR imaging. The samples were kept at 37° C. during imaging. Phantom CEST experiments were taken on a Bruker 11.7 T vertical bore MR scanner, using a 20 mm birdcage transmit/receive coil. CEST images were acquired using a RARE (RARE=8) sequence with CW saturation pulse length of 3 sec and saturation field strength ($B_1$) from 1.2 $_tT$ to 14.4 $_tT$. The CEST Z-spectra were acquired by incrementing saturation frequency every 0.3 ppm from −15 to 15 ppm for phantoms; TR=6 s, effective TE=17 ms, matrix size=64*48 and slice thickness=1.2 mm.

Animal Preparation and Data Acquisition:

In vivo images were acquired on a Bruker Biospec 11.7 T horizontal bore MR scanner, with one axial slice of 1.5 mm thickness obtained through the medulla of both kidneys. CEST images with saturation frequencies oft ±9.3 ppm were acquired repeatedly every 100 sec. both pre- and post-injection. Image parameters were similar to those for the phantom except for TR/TE=5 s/15 ms, with optimized B1=7.2 $_tT$. The BALB/c mice (n=2) weighing 20-25 g (Charles River Laboratories, Wilmington, Mass.) were maintained under specific pathogen free conditions in the animal facility of Johns Hopkins University. For MRI mice were anesthetized by using 0.5-2% isoflurane and placed in a 23 mm transmit/receive mouse coil. Breath rate was monitored throughout in vivo MRI experiments using a respiratory probe. A 60 $_tT$, volume of a 0.25 M solution of 1 in PBS (pH=7) was slowly injected via a catheter into the tail vein. CEST contrast was quantified by $MTR_{asym}=(S^{-\Delta\omega}-S^{+\Delta\omega})/S0$ for phantom and $MTR_{asym}=(S^{-\Delta\omega}-S^{+\Delta\omega})/S^{-\Delta\omega}$ in vivo in order to normalize the conventional magnetization transfer of tissue, where $S^{-\Delta\omega}$ and $S^{+\Delta\omega}$ refer to the water signal intensity with a saturation pulse applied at the frequencies −Δω and +Δω, respectively.

Animal Imaging:

BALB/c mice weighing 20-25 g (Charles River Laboratories, Wilmington, Mass.) were maintained under specific pathogen free conditions in the animal facility of Johns Hopkins University. For MRI, mice were anesthetized using 0.5-2% isoflurane and placed in a 23 mm transmit/receive mouse coil. Breath rate was monitored throughout in vivo MRI experiments using a respiratory probe. A 60 μL, volume of a 0.25 M salicylic acid solution in PBS (pH 7) was slowly injected via a catheter into the tail vein. In vivo images were acquired on a Bruker Biospec 11.7 T horizontal MR scanner, with one axial slice (1.5 mm thick) crossing both renal center chosen for CEST screening. CEST images were acquired both pre- and post-injection. Image parameters were similar to those for the phantom except for TR/TE=5 s/15 ms, with optimized $\omega_1$=7.2 μT.

Example 7

Anthranilic Acid Analogs as Diamagnetic CEST MRI Contrast Agents that Feature an Intramolecular-Bond Shifted Hydrogen 7.1 Overview Diamagnetic chemical exchange saturation transfer (di-aCEST) agents are a new class of imaging agents, which have unique magnetic resonance (MR) properties similar to agents used for optical imaging. Presented herein is a series of anthranilic acid analogs as examples of diaCEST agents that feature an exchangeable proton shifted downfield, namely, an intramolecular-bond shifted hydrogen (IM-SHY), which produces significant and tunable contrast at frequencies of 4.8-9.3 ppm from water. Five analogs of N-sulfonyl anthranilic acids are all highly soluble and produced similar CEST contrast at approximately 6-8 ppm. Flufenamic acid, a commercial nonsteroidal anti-inflammatory drug, displayed CEST contrast at 4.8 ppm. For these N—H IM-SHY agents, the contrast produced was insensitive to pH, making them complementary to existing diaCEST probes. This initial IM-SHY library includes the largest reported shifts for N—H protons on small organic diaCEST agents, and should find use as multifrequency MR agents for in vivo applications.

7.2 Introduction

Chemical exchange saturation transfer (CEST) contrast agents, first introduced in 2000 (Ward, et al., *J. Magn. Reson.* (2000)), are an alternative to traditional magnetic resonance (MR) contrast agents, which rely on direct enhancement of water relaxivity. The CEST mechanism involves saturation of labile protons on the agents via selective irradiation at their resonance frequencies. The signal loss is then transferred to surrounding bulk water through chemical exchange, leading to a reduction in water signal (Aime, et al., *Angew. Chem.* (2002); Ward and Balaban, *Magn. Reson. Med.* (2000); De Leon-Rodriguez, et al., *Acc. Chem. Res.* (2009)). This water signal loss (CEST contrast) results in an amplification of the signal from low-concentration protons through the multiple exchange events occurring during the saturation pulse. Because the CEST contrast is derived from irradiation at a specific proton frequency, it is easier to discriminate from other sources of signal change than T1 or T2* contrast. This frequency dependence of contrast also allows the simultaneous detection and discrimination of multiple agents within an image (McMahon, et al., *Magn. Reson. Med.* (2008); Aime, et al., *Angew. Chem. Int. Edn.* (2005); Viswanathan, et al., *Angew. Chem.* (2009)). Diamagnetic CEST (diaCEST) and paramagnetic CEST (paraCEST) agents have been the subjects of several recent reviews (van Zijl and Yadav, *Magn Reson Med* (2011); Liu, et al., *NMR Biomed* (2013); Castelli, et al., *NMR Biomed* 2013); Soesbe, et al., *NMR Biomed* (2013)). DiaCEST agents, such as glucose (Chan, et al., *Magn Reson Med* (2012); Walker-Samuel, et al., *Nat Med* (2013); Jin, et al., *Magn Reson Med* (2011)), glycogen (van Zijl, et al., *Proc Natl Acad Sci USA* (2007)), myoinositol (Hark, et al., *Neuroimage* (2011)), glutamate (Cai, et al., *Nat Med* (2012)), creatine (Haris, et al., *NMR Biomed* (2012); Kogan, et al., *Magn Reson Med* (2013)), L-arginine (Chan, et al., *Nat Mater* (2013); Liu, et al., *Magn Reson Med* (2012)), glycosaminoglycans (Saar, et al., *NMR Biomed* (2012); Ling, et al., *Proc Natl Acad Sci USA* (2008)) and peptides (McMahon, et al., *Magn Reson Med* (2008); Gilad, et al., *Nat Biotechnol* (2007); Zhou, et al., *Magn Reson Med* (2003); Airan, et al., *Magn Reson Med* (2012)), are attractive biocompatible materials, but compared with paraCEST agents (Hancu, et al., *Acta Radiol* (2010)), they suffer from reduced sensitivity owing to the relatively small chemical shift difference between their exchangeable protons and those of water (1-5.0 ppm). To address this issue, diaCEST agents with protons of increased chemical shift have been reported, including the thymidine analogs (5.5 ppm) (Bar-Shir, et al., *J Am Chem Soc* (2013)) and iopamidol (4.2 and 5.5 ppm) (Aime, et al., *Magn Reson Med* (2005); Longo, et al., *Magn Reson Med* (2011)). Most recently, we reported that the $C_2$—OH in 2-hydroxybenzoic acid analogs resonates between 8.7 and 10.8 ppm from water, with solute-to-water exchange rates ($k_{sw}$) that are well suited to CEST imaging. Yang, et al., *Angew Chemie Int Edn* (2013). Described herein are the anthranilic acid analogs: N-aryl derivatives, N-acyl derivatives and N-sulfonyl derivatives, as another class of IntraMolecular-bond Shifted Hydrogens exchangeable proton (IM-SHY) diaCEST agents, based on the exchange of N—H protons instead of O—H (Scheme 1).

Scheme 1.

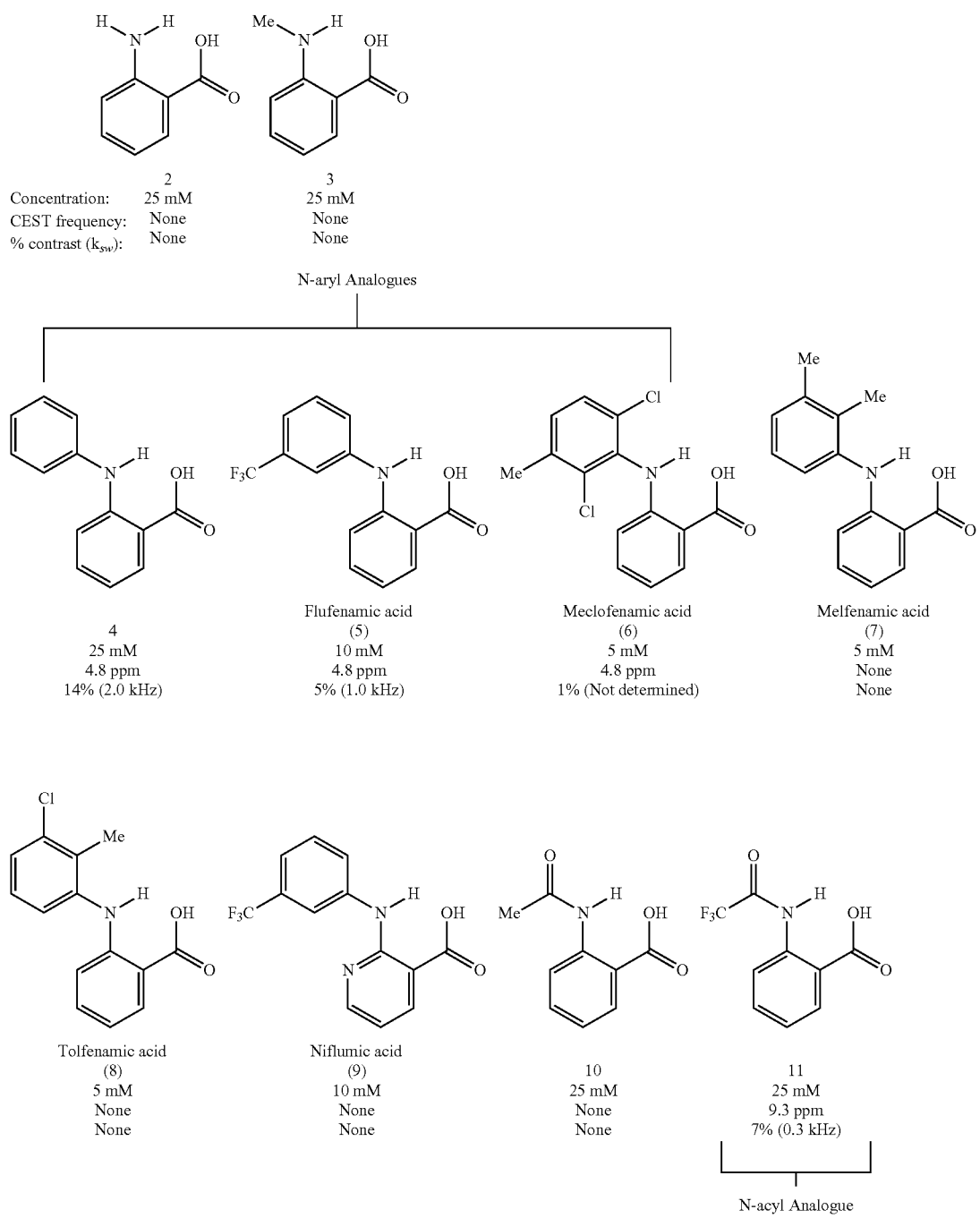

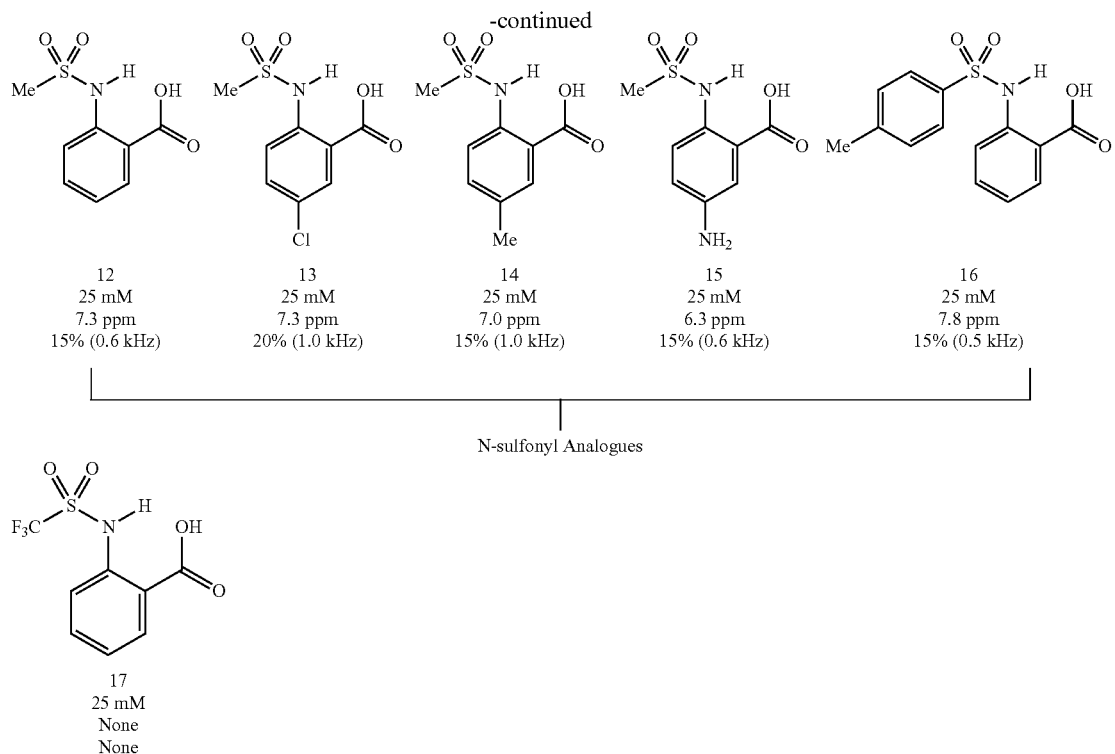

Chemical exchange saturation transfer (CEST) frequency (ppm), contrast (%) and $k_{sw}$ (kHz) of anthranilic acid and its analogs. Experimental conditions: pH 7.1-7.5, using Tsat = 3 s, B1 = 3.6 µT. For Z-spectra, see Tables S1 and S2. All the MR experiments were performed at 37° C.

7.3 Results and Discussion

Salicylic acid (1) displays CEST contrast at 9.3 ppm (Yang, et al., *Angew Chemie Int Edn* (2013)) (FIG. 7). This dramatic chemical shift derives from the low barrier hydrogen bond between the exchangeable phenolic proton and the carboxylate anion at neutral pH. Maciel and Savitsky, *J Phys Chem* (1964); Mock and Morsch, *Tetrahedron* (2001). Similar CEST signals could be observed in other compounds with the 2-hydroxybenzoic acid scaffold, representing a powerful new type of CEST agent, based on the principle of IM-SHY. Yang, et al., *Angew Chemie Int Edn* (2013).

Similar agents with labile anthranilic rather than phenolic protons were prepared to explore further the capabilities of the benzoic acid core for generating CEST contrast. However, anthranilic acid (2), an N—H analog of salicylic acid, failed to produce contrast (Scheme 1, FIG. 7). To understand why, the CEST contrast properties of a wide range of common anthranilic acid analogs were measured, including those with N-alkyl, N-aryl, N-acyl and N-sulfonyl substitutions (Scheme 1). Interestingly, significant contrast was observed in N-phenylanthranilic acid (4), although the labile protons resonate at 4.8 ppm, which is much lower than the 9.3 ppm observed in 1. At a relatively low saturation field strength (B1=3.6 µT), 4 showed a broader peak in the CEST spectrum than 1 and 12 (FIG. 7b), indicating a faster exchange. Using the QUESP (QUantifying Exchange rates using Saturation Power dependence) experiment (McMahon, et al., *Magn Reson Med* (2006)) a $k_{sw}$ equal to 2.0 kHz was measured (Supporting Information, FIG. 11), which is slightly too fast to obtain optimal CEST contrast using the 3-5 µT saturation pulses of the clinical scanners used in the experiments. Comparing the CEST signal between 4 and 2, the loss of CEST signal in 2 indicates that $k_{sw}$ is too high. This is possibly due to the presence of the additional nonhydrogen-bonded C2 N—H proton, which might undergo a fast intramolecular exchange with the hydrogen-bonded proton. In addition, if we modify 2 through substitution of a methyl group for one of the amine protons (3), the CEST contrast is still absent, which implies that stereoelectronic influences are also important (Scheme 1). It is worth mentioning that N-phenylanthranilic acid analogs are commonly used as nonsteroidal anti-inflammatory drugs. The CEST properties were measured on five commercially available drugs: flufenamic acid (5), meclofenamic acid (6), mefenamic acid (7), tolfenamic acid (8) and niflumic acid (9). Their water solubility is generally low (approximately 10 mM or lower). As shown in Scheme 1, flufenamic acid (5) showed similar CEST properties to 4. The exchangeable proton resonates at 4.8 ppm, with $k_{sw}$=1.0 kHz. The CEST data of 6-8 indicated the importance of steric interaction on the proton exchange rate with water. Adding the chloro group ortho to the exchangeable N—H (6) reduced its water accessibility and the CEST contrast dropped to 1%. This is presumably because the exchange is too slow; however, it is difficult to quantify $k_{sw}$ because of the small contrast. Increasing the steric hindrance through addition of methyl (7 and 8) eliminated the CEST signal. Niflumic acid (9), the pyridine analog of 5, did not display any CEST contrast. One possible explanation is that the presence of the pyridine nitrogen tends to strongly hydrogen bond to water and alters the proton exchange of the IM-SHY-NH.

The detection limits of 5 with CEST was determined, because it could potentially be translated into clinical applications. Lovering, et al., *Cancer Res* (2004). The solubility of 5 is quite poor at pH values below 7; however, 10 mM could be achieved in phosphate-buffered saline buffer at pH above 7.2. As shown by the QUESP data in FIG. 8(a), the contrast is near maximal at B1>6 µT, with a smaller $k_{sw}$ (1.0 kHz) than that of 4. The peaks in the Z-spectrum and the MTR$_{asym}$ spectrum are also sharper than those of 4 (FIG. 24), which is also due to a slower $k_{sw}$. The contrast of 5 is nearly linearly dependent with concentration over a range from 0.75 to 10 mM (Ali, et al., *Acc Chem Res* (2009)) (pH 7.4), with 1.2% contrast observed at a concentration of 1.5 mM (FIG. 8b).

Figure 9A:
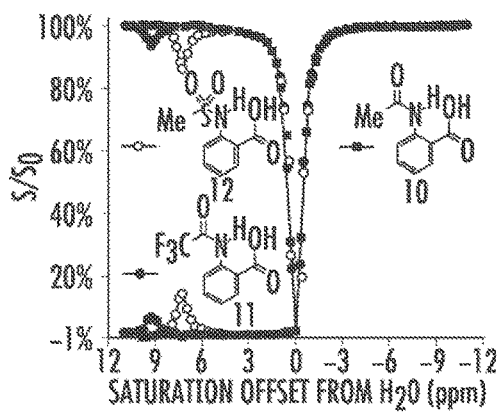
Figure 9B:
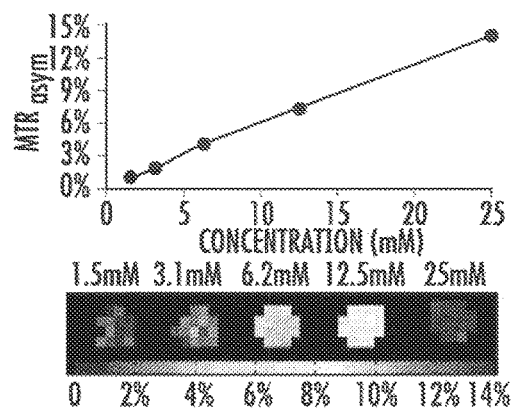
Figure 9C:
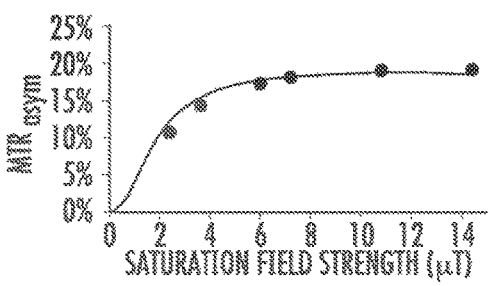
Figure 9D:
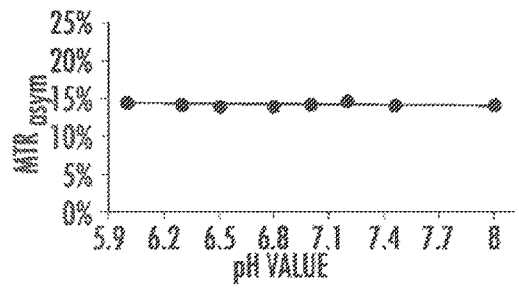
Figure 9E:
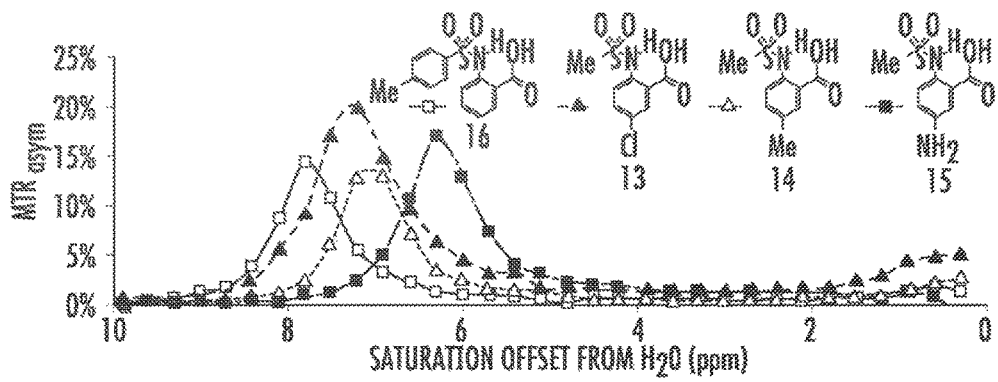

In an attempt to increase the chemical shift further to fit the slow to intermediate detection window of CEST ($k_{sw}<\Delta\omega$) while still keeping $k_{sw}$ slow enough to achieve efficient saturation using a B1 suitable for the MR hardware used in our in vivo scans, the C2 amide analogs of anthranilic acid were investigated. Amide N—H protons tend to be shifted further than amine protons, although they also tend to exchange with water more slowly, as well (5). As expected, 10 did not show any CEST contrast, presumably because the $k_{sw}$ is too slow (FIG. 9a, Scheme 1). However, after modification of the structure to 11, an example of a more acidic N—H proton, CEST contrast with the labile proton resonating at 9.3 ppm was observed, indicating a strong hydrogen bond interaction in water. The contrast produced by 11 is relatively low (6% at 25 mM, B1=3.6 µT), because $k_{sw}$ is relatively slow (0.3 kHz, see Supporting Information, FIGS. 12 and 13 for QUESP/pH details). Further increasing the acidity through 2-(methyl-sulfonamido) benzoic acid (12) resulted in more substantial contrast at 7.3 ppm (~15% at 25 mM, B1=3.6 µT), based on adjusting the proton exchange of the IM-SHY-NH. According to QUESP measurements, 12 displays a $k_{sw}$=0.6 kHz at pH=7.1, which is quite similar to salicylic acid (Yang, et al., *Angew Chemie Int Edn* (2013)) and barbituric acid (Supporting Information, FIG. 15). Maximum contrast was achieved using B1=6 µT or higher with ~90% of this contrast available at B1=3.6 µT (FIG. 9c), which is near the maximum power we can apply using a parallel transmit body coil on our clinical scanners. More interestingly, the contrast and $k_{sw}$ of 11 and 12 remained almost constant between the pH values 6 and 8 (FIG. 9d and FIGS. 12-14 in the Supporting Information).

For comparison, salicylic acid (1), an alternative IM-SHY agent, possesses protons with $k_{sw}$ that decrease dramatically over this range ($k_{sw}$=2.4 kHz at pH 6.5, $k_{sw}$=0.4 kHz at pH 7.8). This pH independence makes 11 and 12 ideal IM-SHY probes for in vivo quantification purposes. As expected, a nearly linear relationship between contrast and concentration was observed for 12 (FIG. 9b), with 1% CEST contrast produced at a concentration of 1.5 mM. Although the chemical shift is not as large as 1 or 11, 12 represents the first diaCEST agent with labile N—H protons resonating at 7-8 ppm from water that produces significant contrast. This compound should be useful for multiple frequency detection and complementary to other existing diaCEST probes. Encouraged by the result from 12, several commercially available analogs were investigated to check if the CEST contrast of this scaffold would tolerate chemical modification. As shown in Scheme 1 and FIG. 9(e), similar contrast was obtained upon chemical modification of the aniline ring (13-15), with the CEST frequency varying from 6 to 7.3 ppm. Placing a strong electron donating —NH2 group (15) at the para-position to the $C_2$—NH reduced the CEST frequency to 6.3 ppm, which is quite similar to the electronic effects observed previously. Yang, et al., *Angew Chemie Int Edn* (2013). Placing a —Cl at the para-position of the $C_2$—NH (13) led to faster $k_{sw}$ (1.0 kHz), and as a result a higher CEST contrast (~20%). Substitution of a phenyl for the methyl (16) resulted in deshielding with the chemical shift increased to 7.8 ppm. In comparison, replacing the methyl group in 12 with a —CF$_3$ (17) resulted in loss of CEST contrast. As this group of agents, 12-16, generated similar contrast to 1 in phantoms, we further chose to monitor in vivo the contrast in kidneys after administration into the tail vein of mice of the most sensitive, 13 (FIG. 10). The contrast was monitored over time, and compared with the pre-injection images (FIG. 10b); a 2-3% increase in the CEST contrast was observed 7.5 min after injection integrating from 7.0 to 7.6 ppm (FIG. 10b, c). The histogram in FIG. 10(d) indicates the pixelwise distribution of MTR$_{asym}$ values for mouse 1 pre- and post-injection. A negative MTR$_{asym}$ was observed as baseline for the kidneys, which is presumably due to strong relayed NOE transfer of signal loss to water. Jones, et al., *Neuroimage* (2013); Pekar, et al., *Magn Reson Med* (1996). As shown in FIG. 10(e), for both mice the contrast reached maximum at approximately 7.5 min post-injection.

As shown hereinabove, anthranilic acid IM-SHY probes have larger shifts for their exchangeable protons than spherical lipoCEST agents (10), and similar shifts to those found for paraCEST probes such as Yb-DO3A-oAA. Liu, et al., *Mol Imag* (2012). The shifts are not nearly as large as some of the Yb, Eu, Tm or Dy complexes described previously (Terreno, et al., *Contrast Media Mol Imag* (2010); Sherry and Woods, *Annu Rev Biomed Eng* (2008); Chauvin, et al., *Angew Chem Int Edn* (2008); Schroder, et al., *Science* (2006)) or the cryptophane cages used for hyperCEST (Schroder, et al., *Science* (2006)); however, because $k_{sw}$ can be tuned to be as slow as 0.5-1 kHz through structure changes and is insensitive to pH in the physiologically relevant range, these IM-SHY probes are well suited for detection using saturation pulses attainable on clinical scanners.

7.4 Conclusion

Anthranilic acid provides a suitable scaffold for tunable IM-SHY diaCEST agents. Labile protons in N-aryl anthranilic acids (4-6) resonate at 4.8 ppm, while those for N-sulfonyl anthranilic acids (12-16) resonate between 6 and 8 ppm, and for 11 labile protons resonate at 9.3 ppm. Anthranilic acid analogs could be used for multicolor MR imaging, with one nonsteroidal anti-inflammatory drug, 5, already administered to patients, having been identified among these analogs. The 2-sulfonamidobenzoic acid scaffold has been shown to allow chemical modification with labile protons that exchange in a non-pH-dependent manner, which could be advantageous for in vivo quantification.

7.5. Experimental Section

7.5.1 Phantom Preparation and Data Acquisition

Compounds 1-12 were purchased from Sigma Aldrich (St Louis, Mo., USA). Compounds 13-17 were purchased from Enamine Ltd (Monmouth, N.J., USA). Samples were dissolved in 0.01 M phosphate-buffered saline at several concentrations from 1.5 to 25 mM depending on the solubility, and titrated using high-concentration HCl/NaOH to various pH values ranging from 6 to 8. The solutions were placed into 1 mm glass capillaries and assembled in a holder for CEST MR imaging. They were kept at 37° C. during imaging. Phantom CEST experiments were performed on a Bruker 11.7 T vertical bore MR scanner, using a 20 mm birdcage transmit/receive coil. CEST images were acquired using a Rapid Acquisition with Refocused Echoes (RARE) (RARE factor=8) sequence with a continuous wave saturation pulse length of 3 s and saturation field strength (B1) from 1.2 to 14.4 µT. The CEST Z-spectra were acquired by incrementing the saturation frequency every 0.3 ppm from −15 to 15 ppm; repetition time (TR)/effective echo time (TE)=6 s/17 ms with linear phase-encoding, matrix size=64×48 and slice thickness=1.2 mm. For determining $k_{sw}$ using QUESP, Z-spectra were collected at B1=1.2, 2.4, 3.6, 5.4, 7.2, 10.8 and 11.4 µT.

7.5.2 In Vivo Mouse Imaging

To evaluate whether the N-sulfonyl derivatives, 12-16, could be detected after administration into live animals, we injected two mice with 60 µL of a 0.25 M solution of compound 13 and collected CEST images. Images consisting of a single axial slice containing both kidneys were collected. To improve the temporal resolution and able to correct the B0 shift, we collected a partial Z-spectrum every 5 min by incrementing $\Delta\omega$ over 10 frequencies (±8.2, ±7.6, ±7.3, ±7 and ±6.6 ppm), and an average $MTR_{asym}$ (at ±7.6, ±7.3 and ±7 ppm). The imaging sequence employed is the same as for the phantoms, with the following parameters: B1=3.6 µT, saturation duration (Tsat) 3 s, TR/effective TE=5 s/16 ms with linear phase-encoding, matrix size 96×64.

7.5.3 Post-Processing

CEST contrast was quantified using $MTR_{asym}$=[S(−$\Delta\omega$)−S(+$\Delta\omega$))]/S0 for phantom and 1−S(+$\Delta\omega$))/S(−$\Delta\omega$) in vivo to increase the temporal resolution and reduce the motion where S(+$\Delta\omega$) represents water signal intensity with a saturation pulse applied at the frequency+$\Delta\omega$ and S0 represents the water signal without a saturation pulse.

The Z-spectra were corrected pixel by pixel using a B0 map acquired using Water Saturation Shift Referencing (WASSR) as described in detail previously. Liu, et al., NMR Biomed (2013). To indicate the kinetics of CEST contrast upon injection of the agents, we subtracted the $MTR_{asym}$ values at each time-point with a reference $MTR_{asym}$ (0) at pre-injection, that is, $\Delta MTR_{asym}$ (t)=$MTR_{asym}$ (t)−$MTR_{asym}$ (0), and plotted the averaged $\Delta MTR_{asym}$ (t) of the whole kidney as a function of minutes post-injection. The solvent to water exchange rate ($k_{sw}$) was calculated according to the QUEST and/or QUESP methods (McMahon, et al., Magn Reson Med (2006)), which were considered as a simple and robust method for estimating $k_{sw}$, especially for the slow to intermediate exchange regime. Randtke, et al., Magn Reson Med; Sun, Magn Reson Med (2012).

In particular, the two-pool model Bloch equations were numerically pooled to fit the measured $MTR_{asym}$ values as a function of different Tsat or $B_1$ as described previously (McMahon, et al., Magn Reson Med (2006)), with the following relaxation parameters for water and solute respectively, where $R_{1w}$ is the longitudinal relaxation time for water and $R_{2w}$ is the transverse relaxation time for water: $R_{2w}$=0.9 s$^{-1}$, $R_{1s}$=0.71 s$^{-1}$, $R_{2s}$=39 s$^{-1}$. $R_{1w}$ was allowed to float between 0.33 and s$^{-1}$ to obtain the best fit. The QUESP/QUEST fittings are shown in the Supporting Information, FIGS. 11-15.

As compound 4 is not soluble at 25 mM at acidic pH values (pH<7). As a result we titrated samples at a 15 mM concentration of 4 to measure $k_{sw}$. See FIG. 11.

Example 8

Tuning Intra-Molecular Hydrogen-Bonded Phenols as diaCEST Probes 8.1 Overview

The optimal exchange properties for CEST contrast agents were characterized on 3 T clinical scanners using CW saturation transfer. It was demonstrated that the exchangeable protons in phenols can be tuned to reach these criteria through proper ring substitution. Systematic modification allows the chemical shift of the exchangeable protons to be positioned between 4.8 ppm to 12 ppm from water and enables adjustment of the proton exchange rate to maximize CEST contrast at these shifts. In particular, 44 hydrogen-bonded phenols are investigated for their potential as CEST MRI contrast agents and the stereoelectronic effects on their CEST properties summarized. Furthermore, a pair of compounds, 2,5-dihydroxyterephthalic acid (42) and 4,6-dihydroxyisophthalic acid (43), were identified which produce the highest sensitivity through incorporating two exchangeable protons per ring, and determine that as low as 200 µM of 42 could be detected.

8.2 Introduction

Due to its exquisite soft tissue contrast and high spatial resolution, magnetic resonance imaging (MRI) is a preeminent clinical diagnostic tool. In over one third of clinical MRI scans, exogenous contrast agents such as gadolinium complexes are administered to improve sensitivity. Caravan, et al., *Chemical Reviews* (1999). Those compounds work by enhancing the water relaxation ($T_1$) in tissue, with ongoing efforts in the design of analogs that enhance relaxivity at high fields. Caravan, et al., *Contrast Media & Molecular Imaging* (1999); Livramento, et al., *Dalton Transactions* (2008). Relaxation-based agents, including gadolinium complexes, manganese, Pautler, et al., *Magnetic Resonance in Medicine* (1998), and iron oxides, Laurent, et al., *Chemical Reviews* (2008); Harisinghani, et al., *New England Journal of Medicine* (2003), were the status quo for exogenous MRI contrast until Ward and Balaban suggested as an alternative using exchangeable solute protons in diamagnetic compounds to produce MRI contrast. Ward, et al., *Journal of Magnetic Resonance* (2000)]. Soon after, van Zijl and colleagues focused on detecting diamagnetic peptides and nucleic acid based CEST agents, Zhou, et al., *Magnetic resonance in medicine: official journal of the Society of Magnetic Resonance in Medicine/Society of Magnetic Resonance in Medicine* (2003); Snoussi, et al., *Magn Reson Med* (2003); Goffeney, et al., *Journal of the American Chemical Society* (2001), while Sherry and Aime and colleagues developed paramagnetic lanthanide chelates which could also generate contrast based on proton exchange with water. Zhang, et al., *Journal of the American Chemical Society* (2001); Aime, et al., *Angewandte Chemie* (2002). Importantly, unlike relaxation agents, such contrast can be modulated by selectively irradiating the labile protons using a radiofrequency pulse corresponding to the chemical shift of the exchangeable proton in the system under study. Other significant advantages of the method, termed chemical exchange saturation transfer (CEST), are that the signal of the solute molecules, which are in relatively low concentration, can be enhanced by several orders of magnitude, Hancu, et al., *Acta Radiologica* (2010); Liu, et al., *Nmr in Biomedicine* (2013); Castelli, et al., *NMR in Biomedicine* (2013); van Zijl and Yadav, *Magnetic Resonance in Medicine* (2011), and that the contrast produced is sensitive to environmental parameters such as temperature, pH, membrane fluidity and cation concentration. Schroeder, et al., *Physical Review Letters* (2008); Ward and Balaban, *Magnetic resonance in medicine: official journal of the Society of Magnetic Resonance in Medicine/Society of Magnetic Resonance in Medicine* (2000); Schnurr, et al., *Physical Chemistry Chemical Physics* (2013); Trokowski, et al., *Ang-* ewandte Chemie-International Edition (2005)]. Several common metabolites have been reported to produce significant CEST contrast including glucose, glycogen, myo-inositol, glutamate, creatine, L-arginine, glycosaminoglycans, nucleic acids and peptides. Zhou, et al., *Magnetic resonance in medicine: official journal of the Society of Magnetic Resonance in Medicine/Society of Magnetic Resonance in Medicine* (2003); Gilad, et al., *Nature Biotechnology* (2007); Chan, et al., *Nature materials* (2013); Chan, et al., *Magnetic resonance in medicine: official journal of the Society of Magnetic Resonance in Medicine/Society of Magnetic Resonance in Medicine* (2012); Ling, et al., *Proceedings of the National Academy of Sciences of the United States of America* (2008); Cai, et al., *Nature Medicine* (2012); Haris, et al., *NeuroImage* (2011); Kogan, et al., *Magnetic resonance in medicine: official journal of the Society of Magnetic Resonance in Medicine/Society of Magnetic Resonance in Medicine* (2013); McMahon, et al., *Magnetic Resonance in Medicine* (2008); Walker-Samuel, et al., *Nature Medicine* (2013); Liu, et al., *Journal of the American Chemical Society* (2011)].

Further, to date, several human studies with administration of exogenous diamagnetic CEST agents, Mueller-Lutz, et al., *Proc. Intl. Soc. Mag. Reason. Med.* (2013); Keupp, et al., *Proc. Intl. Soc. Mag. Reason. Med* (2011), have been reported, with more under way.

A key requirement for CEST MRI experiments is to selectively irradiate solute protons and avoid perturbing the bulk water signal. Consequently, the chemical shift frequency of the labile solute protons must be distinct from the bulk water resonance to enable their detection through saturation transfer. On the NMR chemical shift time scale, that implies the exchangeable solute protons need to be in the slow-intermediate exchange regime. i.e., the rate of exchange ($k_{ex}$) must preferably be less than the difference in frequency between the exchangeable solute protons and the water protons ($\Delta\omega$):

$$\Delta\omega \geq k_{ex} \quad \text{(eq. 3)}$$

The importance in balancing chemical shift and exchange rate of the labile protons has been discussed extensively in several reviews. Hancu, et al., *Acta Radiologica* (2010); Liu, et al., *NMR in Biomedicine* (2013); Castelli, et al., *NMR in Biomedicine* (2013). To define properly which exchange rates and chemical shifts are desirable for exogenous CEST contrast agents, we numerically solved the Bloch-McConnell equations, McMahon, et al., *Magnetic Resonance in Medicine* (2006), for a two-pool system for a long continuous wave saturation pulse over a range of solute proton exchange rates and chemical shifts with the results displayed at $\omega_1=2$ μT, 4 μT in FIG. 19.

The simulations represent imaging conditions currently feasible on 3 T clinical scanners, and show the great advantage of increasing the chemical shift beyond 4 ppm with respect to the water proton resonance, with diminishing gains occurring by approximately 12 ppm, provided that a 4 μT saturation pulse is utilized. The optimum $k_{ex}$ is about 1,050 s$^{-1}$ for that saturation field strength. A 55% improvement could be realized should it be feasible to increase the labile proton chemical shift to 20 ppm and apply long 8 μT saturation pulses on clinical scanners, but this is currently not feasible using a clinically relevant body coil. Diamagnetic CEST (diaCEST) contrast agents such as glucose, creatine and other common metabolites are very attractive biomarkers. However, their exchangeable protons fall within 3.6 ppm from bulk water, which as shown in FIG. 19 results in reduced sensitivity at 3 T through saturation transfer. Further shifted labile protons (up to approximately 6 ppm) have been reported in barbituric acid, Ward, et al., *Journal of Magnetic Resonance* (2000), iopamidol analogues, Aime, et al., *Magnetic Resonance in Medicine* (2005); Chen, et al., *Magnetic Resonance in Medicine* (2013)] and thymidine analogues, [Bar-Shir, et al., *Journal of the American Chemical Society* (2013)] and represent improvements, but as shown by these simulations are still not ideal.

Large chemical shift diaCEST contrast agents potentially could enable EST imaging on clinical scanners. It was reported previously that the intra-molecular hydrogen bond in salicylic acid (1) helped to shift its phenyl CEST signal to 9.3 ppm. Yah, et al., *Angewandte Chemie-International Edition* (2013). Prolonged retention of the exchangeable phenolic proton through intra-molecular hydrogen bonding resulted in an exchange rate of 600 s$^{-1}$ at neutral pH. At pH values between 6.5 and 7.4, salicylic acid gave the ideal exchange rate (2,400-400 s$^{-1}$) for imaging at low saturation power. Its far down field chemical shift and optimum exchange rate at neutral pH is a combination effect from hydrogen bonding strength, phenolic proton pKa, aromatic deshielding and water solvation of the exchangeable protons. To understand the role of these factors, we systematically investigate how chemical structure can affect the CEST properties of hydrogen bonded, phenol-based Intra-Molecular bond-Shifted Hydrogens (IM-SHY) diaCEST agents. Forty-four related compounds, which adhere to the general scaffold shown in Scheme 2, are characterized with the factors that enable optimization for CEST for this series are also summarized.

Scheme 2. General scaffold for phenol based IM-SHY CEST agents.

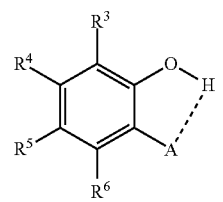

A = Hydrogen Bond Acceptor 8.3 Results and Discussion

Based on the CEST properties of salicylic acid 1, it was of interest to develop a coherent strategy to refine the basic phenol scaffold to maximize the sensitivity of this class of CEST contrast agents. As the intra-molecular hydrogen bond is a key feature, of particular interest was investigating the influence of the hydrogen bond acceptor on the phenol protons. To measure the exchange rates, QUESP, McMahon, et al., *Magnetic Resonance in Medicine* (2006), measurements were performed at 17.6 T, the highest field scanner readily available, where the slow-to-intermediate exchange condition holds for the most compounds. Eight different intra-molecular hydrogen bond acceptors were characterized for water soluble phenols in Table 1.

TABLE 1

Effect of hydrogen bond acceptor on the CEST property of phenol based IM-SHYs

| Compound | Signal (ppm) | Contrast (%) | $k_{ex}$ (s$^{-1}$) |
|---|---|---|---|
| 1 (salicylic acid) | 9.3 | 6.8 | 400 |
| 2 (phenol) | ~5.0 | <0.4 | NA |
| 3 (salicyluric acid derivative) | None | 0 | NA |
| 4 (2-nitrophenol) | None | 0 | NA |
| 5 (8-hydroxyquinoline N-oxide) | 9.5 | 0.7 | 32 |
| 6 | None | 0 | NA |
| 7 (salicylaldoxime) | None | 0 | NA |
| 8 | 7.8 | 1.7 | 15,400 |

TABLE 1-continued

Effect of hydrogen bond acceptor on the CEST property of phenol based IM-SHYs

| Compound | Signal (ppm) | Contrast (%) | $k_{ex}$ (s$^{-1}$) |
|---|---|---|---|
| 9 (2-(1H-tetrazol-5-yl)phenol) | None | 0 | NA |

Conditions: CEST data were obtained at 10 mM concetration,
pH 7.3-7.4,
$t_{sat}$ = 3 sec,
$\omega_1$ = 3.6 μT and 37° C.

Note:
As discussed in an earlier section, the $k_{ex}$ of phenol based protons drops dramatically with an increase in pH (from 6-8). The direct comparison of $k_{ex}$ also needs to take this into account. All pH values in this paper were titrated to 7.3-7.4 for consistency.

Compound 1 showed an exchange rate of 400 s$^{-1}$, which is slightly different from our earlier reported number at neutral pH. The exchange rate on phenol (2) proved too fast to allow detection through saturation transfer (Table 1), and was estimated to be 50,000 s$^{-1}$ at 5.0 ppm. Changing 1 to its glycine conjugate, salicyluric acid (3), gave no contrast at 9.3 ppm, presumably because kex is too fast (Table 1). o-Nitrophenol (4) and 8-hydroxylquinoline N-oxide (5), which were reported to form strong intra-molecular hydrogen bonds, Brzezinski and Zundel, *Journal of Magnetic Resonance* (1969); Abraham and Mobli, *Magnetic Resonance in Chemistry* (2007), failed to produce significant contrast (Table 1) as well. Water soluble salicylaldehyde and its derivatives were also investigated. 3-Formyl-4-hydroxybenzoic acid (6) and salicylaldoxime (7) exchanged too fast to provide contrast. Interestingly, imine groups could attenuate the exchange rate of phenol to a detectable level. N,N'-bis(4-carboxysalicylidene)-1,2-diaminoethane (8) resonated at 7.8 ppm, although the exchange rate was still quite fast at 15,400 s$^{-1}$. Salen ligands such as 8 are commonly used as metal chelators and are widely applied in catalysis. Cozzi, *Chemical Society Reviews* (2004); Tokunaga, et al., *Science* (1997)]. Their IM-SHY signals could potentially be applied for cation sensing, because the phenol protons would be exchanged upon formation of a metal complex. Tetrazole (9), which is commonly used as an isostere for the carboxylate function, was also studied, but failed to provide any contrast due to excessively rapid exchange. The results suggest that the success of salicylic acid is due to the balance of the strength of hydrogen bond between phenol and carboxylate and solvation of water. The carboxylate anion in salicylic acid at neutral pH forms a hydrogen bond which helped to shift the IM-SHY proton further downfield relative to phenol (and water) while maintaining $k_{ex}$ appropriate for detection. Other acceptors tested were either too strong or weak to provide significant contrast.

After accumulating the data in Table 1, the stereo-electronic effects of aromatic ring substitution on salicylic acid were investigated, starting with an investigation of substitution at the 4- and 5-positions (Table 2). Most inductive electron donating (hydroxyl-, amino-) and withdrawing (chloro-, carboxyl-, sulfonyl- and nitro-) groups did not dramatically change the contrast at those positions (Table 2, compounds 10-14 and 16-18).

TABLE 2

Electronic effect of 4- and 5- substituted 2-hydroxybenzoic acids

| Compound | Signal (ppm) | Contrast (%) | $k_{ex}$ (s$^{-1}$) |
|---|---|---|---|
| 10 (5-hydroxy-salicylic acid) | 8.5 | 7.7 | 400 |
| 11 (5-amino-salicylic acid) | 8.5 | 7.0 | 380 |
| 12 (5-chloro-salicylic acid) | 9.0 | 6.2 | 290 |
| 13 (5-sulfo-salicylic acid) | 9.5 | 5.7 | 340 |
| 14 (5-nitro-salicylic acid) | 10.3 | 3.1 | 5660 |

TABLE 2-continued

Electronic effect of 4- and 5- substituted 2-hydroxybenzoic acids

| Compound | Signal (ppm) | Contrast (%) | $k_{ex}$ ($s^{-1}$) |
|---|---|---|---|
| 15 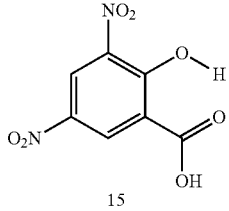 | None | 0 | NA |
| 16 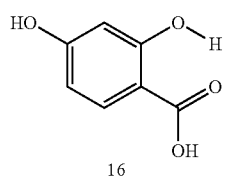 | 9.5 | 7.2 | 460 |
| 17 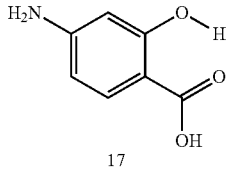 | 9.5 | 6.6 | 384 |
| 18 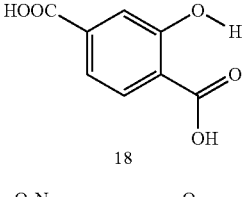 | 9.3 | 6.7 | 420 |
| 19 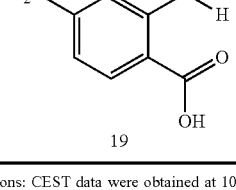 | 9.5 | 6.7 | 1500 |

Conditions: CEST data were obtained at 10 mM concetration,
pH 7.3-7.4,
$t_{sat}$ = 3 sec,
$\omega_1$ = 3.6 µT and 37° C.

The electronic effects on the IM-SHY phenol proton were clearly reflected on the chemical shift of the peak CEST signal. 2,5-Dihydroxybenzoic acid (10) and 5-aminosalicylic acid (11) with electron donating groups para to the position of the IM-SHY proton showed peak signals at 8.5 ppm, compared with the 9.3 ppm in salicylic acid (1), which resulted from their higher pKa values. (Table 2) Electron withdrawing groups in the para-position (Table 2) and meta inductive substitutions (Table 2, compounds 16-18) shifted the IM-SHY signal slightly downfield, because of their lower pKa values. 3,5-Dinitrosalicylic acid (15) failed to give any contrast, because it exists predominantly in its deprotonated form at neutral pH. In contrast to the clear trend in chemical shift, the exchange rates of IM-SHY protons were quite similar to salicylic acid at neutral pH, which indicated the carboxy late anion helped to buffer the moderate pKa changes (Table 2, compounds 10-13 and 16-18). In the case of 5-nitrosalicylic acid (14) and 2-hydroxy-4-nitrobenzoic acid (19), the phenol protons exchanged faster at 5,660 $s^{-1}$ respectively, which indicated their pKa's are quite close to the limit and the O—H bond is quite weak at neutral pH. (Table 2) The chemical shift observed for 5-nitrosalicylic acid (14) was 10.3 ppm and it was close to the maximum that could be achieved by tuning only the pKa of R2-OH.

With improved understanding of the pure electronic effects on the IM-SHY signal, more complicated 3- and 6-substituted 2-hydroxybenzoic acids, which produce ortho effects on the core hydroxyl and carboxylate substituents, were investigated. As shown in Table 3, substitution at the 6-position results in a more nuanced behavior. Any subtle stereo bulky modification can produce a dramatic change in the hydrogen bonding between the carboxylate and IM-SHY proton. Although 2-hydroxy-l-naphthoic acid (20) (Table 3) and 6-methoxysalicylic acid (21) (Table 3) still gave IM-SHY contrast at 9.5 ppm and 9.0 ppm, the exchange rates were around 11-12 times faster compared with salicylic acid, making them less useful for low field MR applications. Interestingly, 2,6-dihydroxybenzoic acid (22) (Table 3) with two 0-H hydrogen-bonded to the carboxylate anion, exchanged with water at the slow rate of 30 $s^{-1}$. That result seems to suggest the importance of the solvation effects of the carboxylate on buffering the IM-SHY exchange rate.

TABLE 3

Stereo-electronic effect of 6-substituted 2-hydroxybenzoic acids

| Compound | Signal (ppm) | Contrast (%) | $k_{ex}$ ($s^{-1}$) |
|---|---|---|---|
| 20 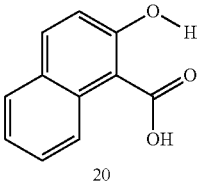 | 9.5 | 3.4 | 4400 |
| 21 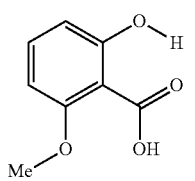 [SMILES: COc1cccc(O)c1C(=O)O] | 9.0 | 3.2 | 4900 |
| 22 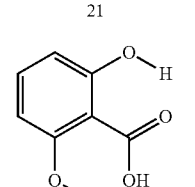 | 9.3 | 0.4 | 30 |

Conditions: CEST data were obtained at 10 mM concetration,
pH 7.3-7.4,
$t_{sat}$ = 3 sec,
$\omega_1$ = 3.6 µT and 37° C.

In contrast to the 6-position, 2-hydroxybenzoic acids with 3-position substituents can result in larger chemical shift phenolic protons than salicylic acid (1) with tunable $k_{ex}$. 3-Methylsalicylic acid (23) (Table 4) showed peak contrast at 9.5 ppm at a slightly slower exchange rate of 250 $s^{-1}$, compared to 400 $s^{-1}$ for 1. Increasing the size of the substituent at the 3-position likely would prevent access to water needed for solvation, and the phenol proton in 3,5- di-tert-butylsalicylic acid (24) (Table 4) exchanged with water slowly at 9.3 ppm (22 s$^{-1}$). 3-Halo substitution affected the IM-SHY signal through a combination of steric and electronic de-shielding effects. The electronic de-shielding trend was shown clearly changing from fluoro to chloro, bromo and iodo, with an increase in the size of the polarizable electron cloud. The chemical shifts were observed at 9.5, 10.3, 10.5 and 10.8 ppm respectively. (Table 4, compounds 25-28) The combination of inductive and steric effects was reflected in the drop in exchange rate from 750, to 1070, 580 and 310 s$^{-1}$. 3,5-Dibromosalicylic acid (27) proved to be the optimum with both a large chemical shift and suitable exchange rate for low-field power MR imaging.

TABLE 4

Stereo-electronic effect of 3-substituted 2-hydroxybenzoic acids

| Compound | Signal (ppm) | Contrast (%) | $k_{ex}$ (s$^{-1}$) |
|---|---|---|---|
| 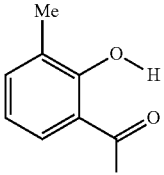 23 | 9.5 | 6.2 | 250 |
| 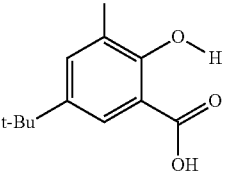 24 | 9.3 | 1.5$^a$ | 22 |
| 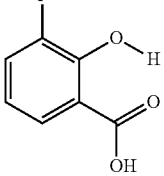 25 | 9.5 | 7.4 | 750 |
| 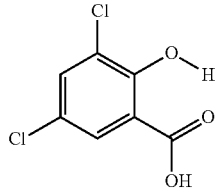 [SMILES: O=C(O)c1cc(Cl)cc(Cl)c1O] 26 | 10.3 | 6.7 | 1070 |
| 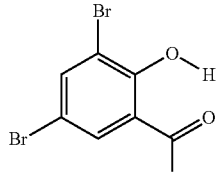 27 | 10.5 | 9.1 | 580 |
| 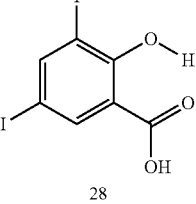 28 | 10.8 | 5.3 | 310 |
| 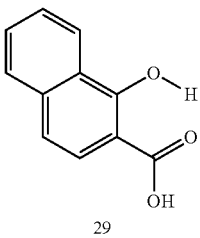 29 | 10.5 | 3.4 | 220 |
| 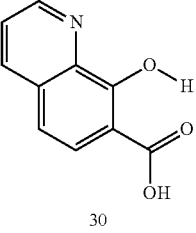 30 | 10.3 | 6.4 | 1530 |
| 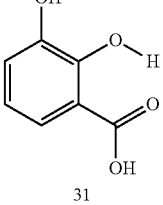 31 | 9.0 | 5.3 | 2000 |
| 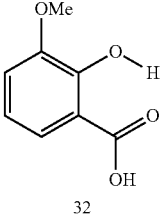 32 | 9.3 | 6.5 | 480 |
| 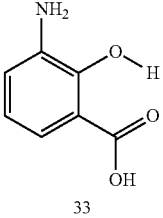 33 | 9.0 | 6.3 | 410 |

TABLE 4-continued

Stereo-electronic effect of 3-substituted 2-hydroxybenzoic acids

| Compound | Signal (ppm) | Contrast (%) | $k_{ex}$ (s$^{-1}$) |
|---|---|---|---|
| 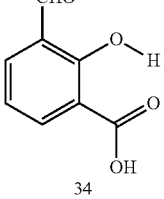 34 | 10.5 | 7.7 | 510 |
| 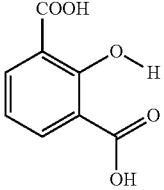 [SMILES: O=C(O)c1cccc(C(=O)O)c1O] 35 | 9.5 | 3.9 | 6680 |
| 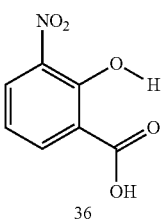 36 | 12.0 | 5.4 | 1430 |

Conditions: CEST data were obtained at 10 mM concetration,
pH 7.3-7.4,
$t_{sat}$ = 3 sec,
$\omega_1$ = 3.6 µT and 37° C.
$^a$20 mM was used because of the low contrast.

3-Aryl substituted salicylic acids were also studied. 1-Hydroxy-2-naphthoic acid (29) did possess a larger chemical shift at 10.5 ppm, but the exchange rate dropped to 220 s$^{-1}$, from introduction of extra steric factors (Table 4). In 8-hydroxy-7-quinolinecarboxylic acid (30), the carboxylate anion was less effective in attenuating the exchange rate of the phenolic proton and the exchange rate was 1,530 s$^{-1}$ at a chemical shift of 10.3 ppm. Without wishing to be bound to any one particular theory, it is thought that the presence of hydrogen bonding of the quinoline nitrogen to water, inducing a faster proton exchange rate, although solvation could also play a role (Table 4). That is similar to behavior seen for amide protons near lysine or arginine sidechains in small peptides. McMahon, *Magnetic Resonance* in Medicine (2008). A similar effect was also observed in 2,3-dihydroxybenzoic acid (31), which resonated at 9.0 ppm with an exchange rate of 2,000 s$^{-1}$ (Table 4). In contrast, its close analogue, 3-methoxysalicylic acid (32), demonstrated the expected IM-SHY signal at 9.3 ppm and 480 s$^{-1}$ (Table 4). However, in 3-aminosalicylic acid (33), that acceleration effect was not observed with the exchange rate 410 s-1 (Table 4). The effect of electron withdrawing groups was also studied. 3-Formylsalicylic acid (34) generated CEST signal at 10.5 ppm with an exchange rate of 510 s$^{-1}$, but 2-hydroxyisophthalic acid (35) resonated more rapidly at 6,680 s-1, decreasing available signal (Table 4). The best de-shielding effect was achieved on 3-nitrosalicylic acid (36) while retaining some balance between the pKa of the phenolic proton. This compound resonated at 12.0 ppm, which is the farthest we have measured for a diaCEST probe, and the exchange rate was 1,430 s$^{-1}$ (Table 4).

A remaining issue to consider is the role of the phenolic)-H group in 2-hydroxybenzoic acid. A series of N—H groups was identified as alternatives, including: arylamino (4.8 ppm for compound 37), sulfoamido (6.3-7.8 ppm for compounds 38-40) and trifluoroacetamido (9.3 ppm for compound 41) groups, Song, et al., *Contrast Media & Molecular Imaging* (Table 5). They behaved in a tunable and pH independent manner as described previously, complementary to the 2-hydroxybenzoic acids discussed here.

TABLE 5

Anthranillic acid derivatives as IM-SHY diaCEST probes.

| Compound | Signal (ppm) | Contrast (%) | $k_{ex}$ (s$^{-1}$) |
|---|---|---|---|
| 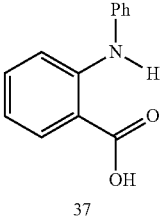 37 | 4.8 | 7.4 | 670 |
| 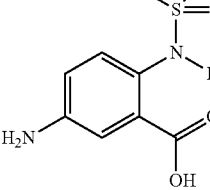 38 | 6.3 | 8.4 | 550 |
| 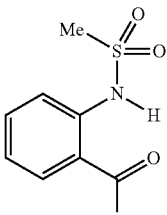 39 | 7.3 | 7.7 | 470 |
| 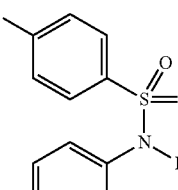 40 | 7.8 | 6.8 | 440 |

TABLE 5-continued

Anthranillic acid derivatives as IM-SHY diaCEST probes.

| Compound | Signal (ppm) | Contrast (%) | $k_{ex}$ ($s^{-1}$) |
|---|---|---|---|
| 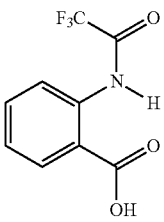 [SMILES: O=C(O)c1ccccc1NC(=O)C(F)(F)F] 41 | 9.3 | 3.5 | 190 |

Conditions: CEST data were obtained at 10 mM concetration,
pH 7.3-7.4,
$t_{sat}$ = 3 sec,
$\omega_1$ = 3.6 µT and 37° C.

The current understanding of the CEST properties of the 2-hydroxybenzoic acid scaffold is summarized in Scheme 2. A) The carboxylate anion is critical to buffer the proton exchange rate of the ortho phenol. It provides the hydrogen bonding and appropriate water solvation environment around the exchangeable proton. B) Substitutions at the 4- and 5-positions on 2-hydroxybenzoic acid slightly affect the chemical shift through electronic effects. Those normally do not change the exchange rate significantly, with the exception of the 5-nitro and 4-nitro groups. They present the best positions at which to conjugate targeting agents and other functions while maintaining CEST signal. C) Modification of the 6-position is not suggested. Maintenance of a R-6 proton is required to provide the correct exchange rate for low field CEST imaging. D) The 3-position is less predictable. Bulky modification at R-3 could reduce the exchange rate too much. That position is also sensitive to fast exchangeable proton substitutions, such as O—H and pyridinium. Extra de-shielding effects, such as on bromo, iodo, aryl, carbonyl and nitro groups, are also tolerated at R-3 position. It is the ideal position to design smart, switchable IM-SHY probes. E) The R-2-OH group could be switched to several N—H groups.

With the basic properties of IM-SHY 2-hydroxybenzoic acid probes discussed above, we decided to investigate if we could improve the detection limit further through increasing the number of IM-SHY cores. To avoid the ortho substitution close to the primary IM-SHY core, 2,5-dihydroxyterephthalic acid (42) and 4,6-dihydroxyisophthalic acid (43) were tested (Table 6). Both of those compounds were high sensitivity diaCEST probes. 2,5-Dihydroxyterephthalic acid (42) IM-SHY protons resonated at 8.3 ppm with exchange rate of 990 s$^{-1}$, making it a higher sensitivity probe when high saturation fields (4 µT) are employed. 4,6-Dihydroxyisophthalic acid IM-SHY protons resonated at 9.8 ppm and exchanged with water at 460 s$^{-1}$, making this compound suitable for use with lower saturation field strengths (2 µT). They can generate 17.1% and 13.0% contrast respectively, at 10 mM concentration using 3.6 µT, making these the highest sensitivity diamagnetic contrast probes developed to date. Pamoic acid (44), a FDA proved drug additive, Saesmaa and Tatterman, *Journal of Pharmaceutical and Biomedical Analysis* (1990), was also tested. But the IM-SHY protons exchanged too slowly (130 s$^{-1}$), producing only 5.7% contrast at 10 mM, because of the bulky ortho substitution to the phenolic O—H.

TABLE 6

Substituted 2-hydroxybenzoic acids with increased IM-SHY signal density

| Compound | Signal (ppm) | Contrast (% at 3.6 uT) | $k_{ex}$ ($s^{-1}$) |
|---|---|---|---|
| 42 | 8.3 | 17.1 | 990 |
| 43 | 9.8 | 13.0 | 460 |
| 44 | 9.5 | 5.7 | 130 |

Conditions: CEST data were obtained at 10 mM concetration,
pH 7.3-7.4,
$t_{sat}$ = 3 sec,
$\omega_1$ = 3.6 µT and 37° C.

The detection limit of the agent generating the highest contrast, 2,5-dihydroxyterephthalic acid (42), was tested at 3 T to determine whether it could be applied easily to scanning at clinical field strengths (3 T). Below 10 mM, the contrast was linearly dependent on concentration, as shown in FIG. 20. At 2.1 µT, 0.5 mM of 42 still produced 0.6% contrast at 8.5 ppm, as shown in FIG. 20. Because of its higher exchange rate at T=37° C., the detection limit could be pushed down to 0.2 mM with around 0.5% contrast when using 8 µT. The contrast was approximately 60% higher than salicylic acid at 2.1 µT on the 3 T scanners, with this sensitivity increasing substantially stronger saturation fields, and is as large as 300% higher using 8 µT on our 17/0.6 T scanner.

Hydrogen bonded phenols exist widely as natural products and also as therapeutics. For example, aspirin is the most commonly used nonsteroidal anti-inflammatory drug (NSAID), which works as a prodrug of salicylic acid. Doxorubicin and mitoxantrone are used commonly as anti-tumor drugs. Tetracycline is one of the oldest antibiotics. Enterobacin exists as the strongest iron binding compound in bacteria. The toxicity for a number of those compounds has been determined, and they are generally not toxic at doses suitable for diaCEST imaging. For example, 4-amino salicylic acid has a median LD$_{50}$ of 4,250 mg/kg. 2,4-Dihydroxy benzoic acid, salicylic acid, flufenamic acid also have relatively high $LD_{50}$ values at 800 mg/kg, 500 mg/kg and 150 mg/kg, respectively. As described above, criteria were defined that enable phenols to produce substantial CEST contrast at 3 T, which involve a balance between chemical shift and water exchange rate. As shown in FIG. 21, compounds were identified that produce strong contrast from 4.8 ppm to 12 ppm from water based on modifications at the R3, R4, R5, R6 positions in addition to modification of the OH hydrogen bonding partner.

Lanthanide, Iron, Cobalt and Nickel complexes can also feature exchangeable protons with large chemical shifts from water (on the order of 30-700 ppm) and suitable exchange rates. Hancu, et al., *Acta Radiologica* (2010); Terreno, et al., *Contrast Media and Molecular Imaging* (2010); Yoo and Pagel, *Journal of the American Chemical Society* (2006); Dorazio, et al., *Journal of the American Chemical Society* (2011); 20d) Olatunde, et al., *Journal of the American Chemical Society* (2012); Dorazio, et al., *Chemical Communications* (2013). The large chemical shift difference with water for those paramagnetic CEST (paraCEST) agents supports the use of stronger saturation pulses to detect protons with faster exchange rates as mentioned in Eq. 3. Despite the advantages of the larger allowed exchange rates for CEST agents, their contrast is limited to 8.5% at 10 mM exchangeable protons when utilizing a 4 µT saturation field. Larger contrast could therefore be realized using transmission coils capable of keeping the Specific Absorption Rate (SAR) produced by long>8 µT pulses to within heating limits.

While the performance of the IM-SHY scaffold using continuous wave saturation transfer preparation was determined, the measurements included do not represent the performance of these compounds using pulsed exchange transfer methods, such as two frequency irradiation, Lee, et al., *Journal of Magnetic Resonance* (2012), CERT, Zu, et al., *Magnetic Resonance in Medicine* (2012), Frequency labeled EXchange transfer (FLEX), Yadav, et al., *Magnetic Resonance in Medicine* (2012); Friedman, et al., *Journal of the American Chemical Society* (2010), or Variable Delay Multiple Pulse (VDMP) transfer [Xu, et al., *Magnetic Resonance in Medicine* (2013), as these sequences are still under development at 3 T. The use of a limited series of short selective high-power pulses has major advantages for detecting rapidly exchanging compounds, van Zijl and Yadav, *Magnetic Resonance in Medicine* (2011), as recently demonstrated using FLEX on a paraCEST agent with a water exchange rate of 19,000 Hz. That will be the subject of future studies. It is expected that the set of compounds described here will perform well using these new schemes.

8.4 Conclusion

In conclusion, a general scaffold for producing strong CEST contrast is described based on analysis of 44 analogs of 2-hydroxybenzoic acid. Steroelectronic effects of substitutions on the aromatic ring on CEST properties are summarized, with the phenol IM-SHY agents producing strong contrast from 4.8 ppm to 12 ppm. Compounds can be tuned with respect both to their pKa values and proton exchange rates, the key determinants of CEST signal by enabling control of chemical shift and degree of water saturation, which impact on overall sensitivity. These probes were designed with multi-frequency CEST imaging in mind, with frequencies spanning a range that should allow discrimination between multiple agents within an image. As small molecules, we identify 42 and 43 as the highest sensitivity contrast agents through incorporating two IM-SHY protons with suitable exchange rates and could be detected down to 200 µM for 42 at clinically useful field strengths.

8.5 Experimental Section

8.5.1 Phantom Preparation:

Samples were dissolved in 0.01 M phosphate-buffered saline (PBS) at concentrations from 0.1 mM to 10 mM, and titrated using high concentration HCl/NaOH to obtain physiologically relevant pH values approximately 7.4. The solutions were placed into 1 mm glass capillaries and assembled in a holder for CEST MR imaging.

8.5.2 Data Acquisition:

Phantom CEST experiments were performed on a Bruker Avance III 17.6 T vertical bore MR scanner using a 20 mm SAW type microimaging transmit/receive coil. The samples were kept at 37° C. during imaging. CEST images were acquired using a RARE (RARE factor=32) sequence with a continuous wave (CW) saturation pulse length of 6 s and saturation field strengths of 1.0, 3.6, and 8.0 µT. The CEST Z-spectra were acquired by incrementing the saturation frequency every 0.25 ppm from −15.0 to 15.0 ppm. TR=15 s, TE=8 ms, matrix size=64×32, slice thickness=3 mm.

For compound 42, CEST experiments were also performed on a 3.0 T Philips Medical Systems human MRI scanner using a parallel transmit body coil for RF transmission and a 32-channel head coil for reception. The CEST images were acquired using a Turbo Spin echo sequence with a CW saturation pulse length of 3 s. The CEST Z-spectra were acquired by incrementing the saturation frequency every 0.38 ppm from −15.0 to 15.0 ppm. TR=12 s, TE=6.4 ms, matrix size=64×58, slice thickness=10 mm.

8.5.3 Post-Processing:

CEST contrast was quantified using $MTR_{asym}$ [Guivel-Scharen, et al., *Journal of Magnetic Resonance* (1998)]. Prior to performing $MTR_{asym}$, the effects from B0 variations were corrected for using the WASSR, Kim, et al., *Magnetic resonance in medicine: official journal of the Society of Magnetic Resonance in Medicine/Society of Magnetic Resonance in Medicine* (2009), method. Exchange rates were determined by fitting a 2-pool Bloch model, McMahon, et al., *Magnetic Resonance in Medicine* (2006), Forsén and Hoffman, *The Journal of Chemical Physics* (1963), to the entire Z-spectra acquired from CEST experiments saturation pulse amplitudes of 1.0, 3.6, and 8.0 µT. The relaxation parameters for each fit were: $R_{1w}$=0.26 s$^{-1}$, $R_{2w}$=0.43 s-1, R1s=0.71 s$^{-1}$, $R_{2s}$=39 s$^{-1}$. These were determined by fitting the direct water saturation line for PBS and were fixed for subsequent fits of each compound with the exchange rate allowed to vary. All data was processed using Python, Scipy, and Numpy (www.python.org, scipy.org, and numpy.scipy.org, respectively).

Example 9

Salicylic Acid and its Analogs for MRI Contrast

The presently disclosed subject matter, in some embodiments, demonstrates that beta-hydroxycarboxylates, including, but not limited to, salicylic acid, salicylates, salicylic acid prodrugs, and any aromatic compound with a hydroxyl (—OH) group ortho to the carboxylic acid, are a general type of MRI organic contrast agent that produce significantly improved contrast in MR images detectable through chemical exchange saturation transfer (CEST) or frequency labeled exchange (FLEX) imaging. The agents can be used for various purposes, including, but not limited to, tumor detection, MRI visualization of nanoparticles, receptor imaging, MRI sensing the concentration of cations, MR imaging of metabolic changes, and MR visualization of transplanted cells.

More particularly, the presently disclosed subject matter includes the development of salicylic acid and salicylic acid analogs with aromatic OH group ortho to the carboxylic acid group that exhibit improved CEST contrast properties and their application for cation sensing and in vivo imaging and the application of prodrugs of salicylic acid to improve MR image quality.

9.1 Representative Beta-Hydroxy Carboxylate Analogs

In particular embodiments, the presently disclosed subject matter provides MRI contrast agents and their use for a variety of clinical or non-clinical purposes. Compared with paraCEST contrast agents, organic CEST contrast agents have several potential advantages, such as lower toxicity due to the absence of lanthanide metals, ease of modification, and clearance through breakdown during natural biochemical processes. Organic CEST agents known in the art, however, suffer from sensitivity drawbacks, especially due to a small chemical shift difference between exchangeable

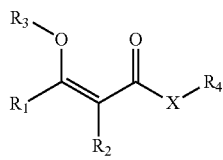

R1 = any carbon and function group, any heteroatoms and proton
R2 = any carbon and function group, any heteroatoms and proton
R3 = any carbon and function group, any heteroatoms and proton
R4 = any carbon and function group, any heteroatoms and proton and any metal or ammonium salts
X = O, NH, NR, C, S

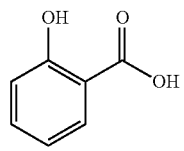 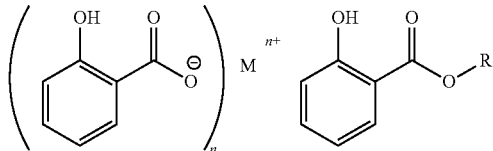

salicylic acid and salicylic acid based drugs including but not limited to Diflunisal, Balsalazide, 4-Aminosalicyclic acid, 5-Aminosalicylic acid (Mesalazine) Olsalazine, Sulfasalazin, 4-(2-hydroxybenzoyl) salicylate salicylates
$M^{n+}$ including but not limited to any metal and ammonium salts
e.g. choline magnesium trisalicylate

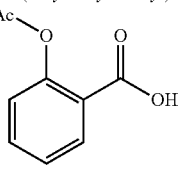 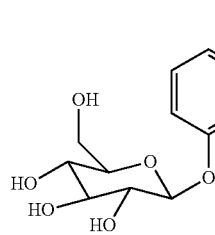 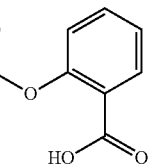

Aspirin                    Salicin                    Salsalate salicylic acid prodrugs including but not limited to Aspirin, Salicin, Salsalate

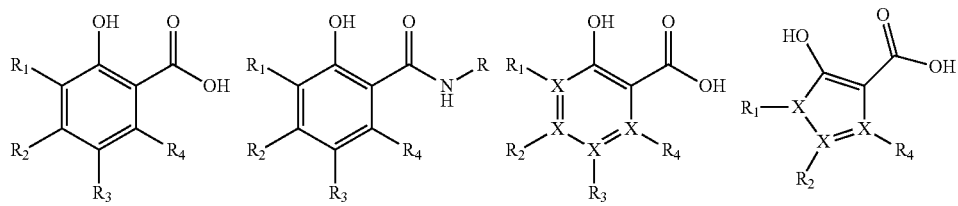

R1 = any carbon and function group, any heteroatoms and proton
R2 = any carbon and function group, any heteroatoms and proton
R3 = any carbon and function group, any heteroatoms and proton
R4 = any carbon and function group, any heteroatoms and proton and any metal or ammonium salts
X = C, N, O, S salicylic acid metabolized products and analogs proton and water. Many challenges exist with respect to detecting CEST contrast agents, including low spatial/temporal resolution, artifacts and low contrast-noise-ratio, and difficulties separating CEST contrast from other sources of water signal loss. In contrast, the presently disclosed MRI organic contrast agents produce significantly improved contrast in MR images in a pH dependent manner detectable through CEST or FLEX imaging. Representative beta-hydroxy carboxylate analogs are provided in Table 4A.

TABLE 4A

Screening of beta-hydroxy carboxylate analogs for CEST contrast

| Entry | Compound | Signal (ppm) | Contrast (%) | $k_{ex}$ (s$^{-1}$) | Concentration (mM) |
|---|---|---|---|---|---|
| 1 | salicylic acid | 9.3 | 6.8 | 400 | 10 |
| 2 | phenol | ~5.0 | <0.4 | NA | 10 |
| 3 | salicyloylglycine | None | 0 | NA | 10 |
| 4 | methyl salicylate | None | 0 | NA | 10 |
| 5 | methyl 5-nitrosalicylate | None | 0 | NA | 10 |
| 6 | 2-nitrophenol | None | 0 | NA | 10 |
| 7 | methyl 4-hydroxy-3-nitrobenzoate | None | 0 | NA | 10 |
| 8 | 8-hydroxyquinoline N-oxide | 9.5 | 0.7 | 32 | 10 |

TABLE 4A-continued

Screening of beta-hydroxy carboxylate analogs for CEST contrast

| Entry | Compound | Signal (ppm) | Contrast (%) | kex (s$^{-1}$) | Concentration (mM) |
|---|---|---|---|---|---|
| 9 | (structure) | None | 0 | NA | 10 |
| 10 | (structure) | None | 0 | NA | 10 |
| 11 | (structure) | 7.8 | 1.7 | 15400 | 10 |
| 12 | (structure) | None | 0 | NA | 10 |
| 13 | (structure) | None | 0 | NA | 10 |
| 14 | (structure) | None | 0 | NA | 10 |
| 15 | (structure) | 8.5 | 7.7 | 400 | 10 |
| 16 | (structure) | 8.5 | 7.0 | 380 | 10 |

TABLE 4A-continued

Screening of beta-hydroxy carboxylate analogs for CEST contrast

| Entry | Compound | Signal (ppm) | Contrast (%) | kex (s$^{-1}$) | Concentration (mM) |
|---|---|---|---|---|---|
| 17 | 5-chlorosalicylic acid | 9.0 | 6.2 | 290 | 10 |
| 18 | 5-sulfosalicylic acid | 9.5 | 5.7 | 340 | 10 |
| 19 | 5-nitrosalicylic acid | 10.3 | 3.1 | 5660 | 10 |
| 20 | 3,5-dinitrosalicylic acid | None | 0 | NA | 10 |
| 21 | 2,4-dihydroxybenzoic acid | 9.5 | 7.2 | 462 | 10 |
| 22 | 4-amino-2-hydroxybenzoic acid | 9.5 | 6.6 | 384 | 10 |
| 23 | 2-hydroxyterephthalic acid | 9.3 | 6.7 | 420 | 10 |
| 24 | 4-nitrosalicylic acid | 9.5 | 6.7 | 1500 | 10 |
| 25 | 2-hydroxy-1-naphthoic acid | 9.5 | 3.4 | 4400 | 10 |

TABLE 4A-continued
Screening of beta-hydroxy carboxylate analogs for CEST contrast
| Entry | Compound | Signal (ppm) | Contrast (%) | kex (s⁻¹) | Concentration (mM) |
|---|---|---|---|---|---|
| 26 | 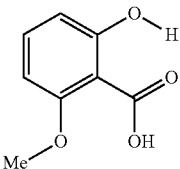 | 9.0 | 3.2 | 4900 | 10 |
| 27 | 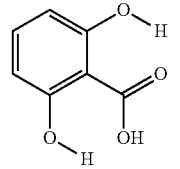 [SMILES: O=C(O)c1c(O)cccc1O] | 9.3 | 0.4 | 30 | 10 |
| 28 | 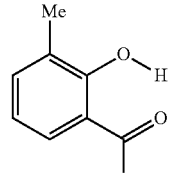 | 9.5 | 6.2 | 250 | 10 |
| 29 | 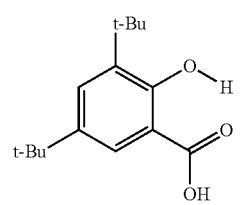 [SMILES: CC(C)(C)c1cc(C(=O)O)c(O)c(C(C)(C)C)c1] | 9.3 | 1.5 | 22 | 20 |
| 30 | 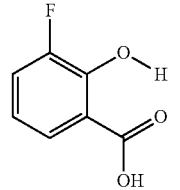 [SMILES: O=C(O)c1cccc(F)c1O] | 9.5 | 7.4 | 750 | 10 |
| 31 | 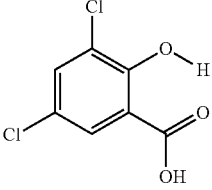 [SMILES: O=C(O)c1cc(Cl)cc(Cl)c1O] | 10.3 | 6.7 | 1070 | 10 |
| 32 | 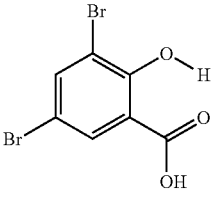 [SMILES: O=C(O)c1cc(Br)cc(Br)c1O] | 10.5 | 9.1 | 580 | 10 |

TABLE 4A-continued
Screening of beta-hydroxy carboxylate analogs for CEST contrast
| Entry | Compound | Signal (ppm) | Contrast (%) | kex (s$^{-1}$) | Concentration (mM) |
|---|---|---|---|---|---|
| 33 | 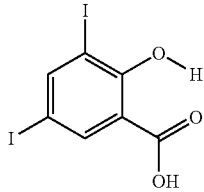 | 10.8 | 5.3 | 310 | 10 |
| 34 | 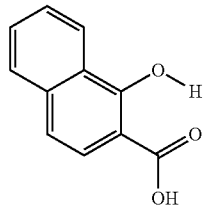 [SMILES: O=C(O)c1ccc2ccccc2c1O] | 10.5 | 3.4 | 220 | 10 |
| 35 | 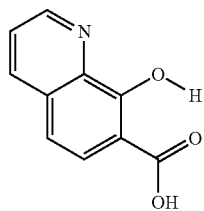 [SMILES: O=C(O)c1ccc2cccnc2c1O] | 10.3 | 6.4 | 1530 | 10 |
| 36 | 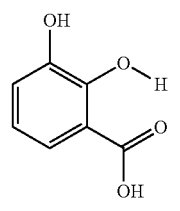 [SMILES: O=C(O)c1cccc(O)c1O] | 9.0 | 5.3 | 2000 | 10 |
| 37 | 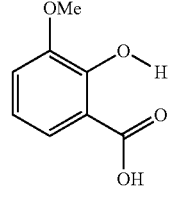 [SMILES: COc1cccc(C(=O)O)c1O] | 9.3 | 6.5 | 480 | 10 |
| 38 | 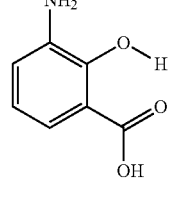 | 9.0 | 6.3 | 410 | 10 |
| 39 | 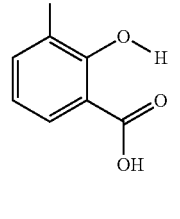 | 10.5 | 7.7 | 510 | 10 |

TABLE 4A-continued

Screening of beta-hydroxy carboxylate analogs for CEST contrast

| Entry | Compound | Signal (ppm) | Contrast (%) | kex (s$^{-1}$) | Concentration (mM) |
|---|---|---|---|---|---|
| 40 | (structure) | 9.5 | 3.9 | 6680 | 10 |
| 41 | (structure) | 12.0 | 5.4 | 1430 | 10 |
| 42 | (structure) | 8.3 | 17.1 | 990 | 10 |
| 43 | (structure) | 9.8 | 13.0 | 460 | 10 |
| 44 | (structure) | 9.5 | 5.7 | 130 | 10 |
| 45 | (structure) | 9.3 | 19.0 | 650 | 25 |

TABLE 4A-continued

Screening of beta-hydroxy carboxylate analogs for CEST contrast

| Entry | Compound | Signal (ppm) | Contrast (%) | kex (s$^{-1}$) | Concentration (mM) |
|---|---|---|---|---|---|
| 46 | (structure) | 9.6 | 20 | 1000 | 25 |
| 47 | (structure) | None | 0 | ND | 25 |
| 48 | (structure) | None | 0 | ND | 25 |
| 49 | (structure) | 4.8 | 7.4 | 674 | 10 |
| 50 | (structure) | 4.8 | 5 | 1000 | 10 |
| 51 | (structure) | 4.8 | 1 | ND | 5 |

TABLE 4A-continued

Screening of beta-hydroxy carboxylate analogs for CEST contrast

| Entry | Compound | Signal (ppm) | Contrast (%) | kex (s⁻¹) | Concentration (mM) |
|---|---|---|---|---|---|
| 52 | 2,3-dimethylphenyl anthranilic acid derivative | None | 0 | ND | 5 |
| 53 | 3-methyl-2-chlorophenyl anthranilic acid derivative | None | 0 | ND | 5 |
| 54 | 3-trifluoromethylphenyl 2-aminonicotinic acid derivative | None | 0 | ND | 10 |
| 55 | N-acetyl anthranilic acid | None | 0 | ND | 25 |
| 56 | N-Boc anthranilic acid | None | 0 | ND | 25 |
| 57 | N-trifluoroacetyl anthranilic acid | 9.3 | 3.5 | 190 | 10 |

TABLE 4A-continued

Screening of beta-hydroxy carboxylate analogs for CEST contrast

| Entry | Compound | Signal (ppm) | Contrast (%) | kex (s⁻¹) | Concentration (mM) |
|---|---|---|---|---|---|
| 58 | [2-(methylsulfonamido)benzoic acid] | 7.3 | 7.7 | 470 | 10 |
| 59 | [5-chloro-2-(methylsulfonamido)benzoic acid] | 7.3 | 20 | 1000 | 25 |
| 60 | [5-methyl-2-(methylsulfonamido)benzoic acid] | 7.0 | 15 | 500 | 25 |
| 61 | [5-amino-2-(methylsulfonamido)benzoic acid] | 6.3 | 8.4 | 550 | 10 |
| 62 | [2-(4-methylphenylsulfonamido)benzoic acid] | 7.8 | 6.8 | 440 | 10 |
| 63 | [2-(trifluoromethylsulfonamido)benzoic acid] | None | 0 | ND | 25 |

TABLE 4A-continued

Screening of beta-hydroxy carboxylate analogs for CEST contrast

| Entry | Compound | Signal (ppm) | Contrast (%) | kex (s$^{-1}$) | Concentration (mM) |
|---|---|---|---|---|---|
| 64 | | None | 0 | ND | 25 |

All compounds were dissolved in 0.01M phosphate-buffered saline (PBS) with concentrations of 100 mM. They were then titrated by HCl/NaOH to the pH of 6 to 8. The solutions were placed into 1-mm capillary tubes and then assembled in a holder for high throughput CEST MR imaging. CEST experiments were taken on a Bruker Biospec 11.7 T MR scanner, using a RARE sequence with CW saturation pulse length of 3 seconds and saturation field strength (B1) of 3.6 μT. The CEST Z-spectra were acquired by incrementing the saturation frequency every 0.3 ppm from −18 ppm to 18 ppm for phantoms; TR=6 s, effective TE=15-19 ms, matrix size=96×64. CEST contrast was quantified by:

$$MTR_{asym} = (S_{-\Delta\omega} - S_{+\Delta\omega})/S0$$

after a voxel-by-voxel B0 correction, with characterized mean Z-spectra and MTR$_{asym}$ spectra for sample ROIs plotted in FIG. 22. Salicylic acid analogs were found to give the excellent CEST contrast with 50% or higher contrast observed at 10 ppm at 100-mM concentrations.

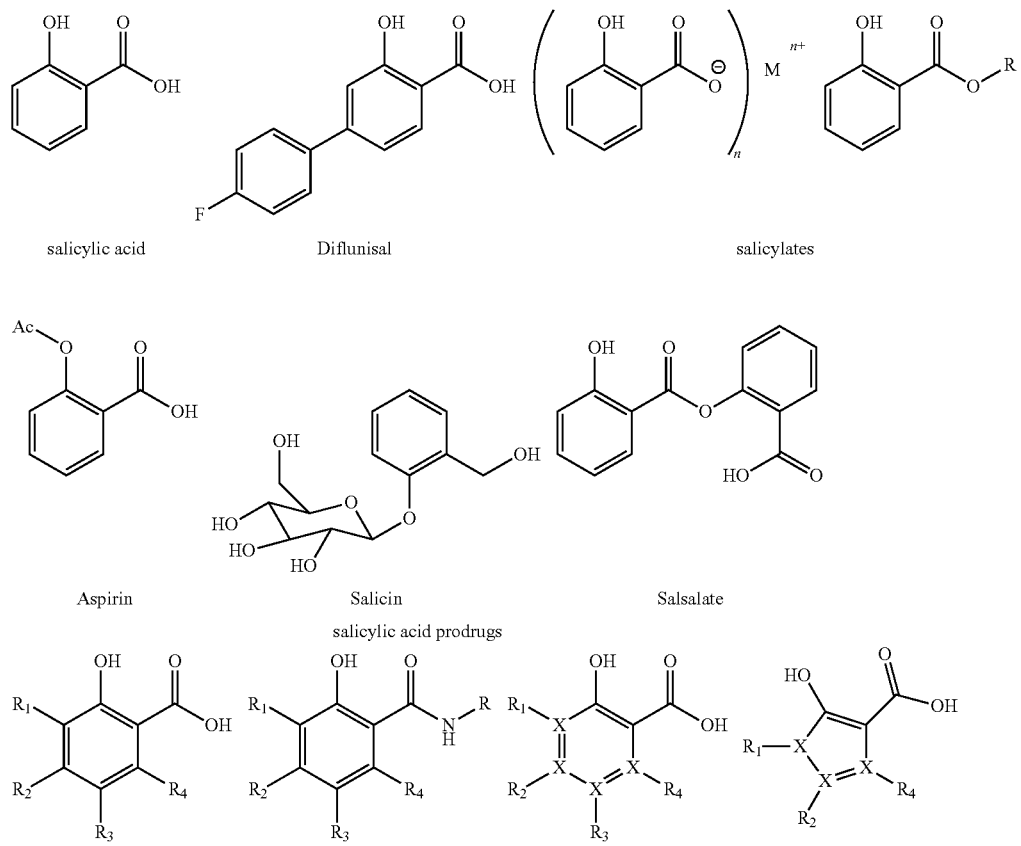

salicylic acid    Diflunisal    salicylates

Aspirin    Salicin    Salsalate salicylic acid prodrugs

R1 = any carbon and function group, any heteroatoms and proton
R2 = any carbon and function group, any heteroatoms and proton
R3 = any carbon and function group, any heteroatoms and proton
R4 = any carbon and function group, any heteroatoms and proton and any metal or ammonium salts
X = C, N, O, S salicylic acid metabolized products and analogs 9.2 Determination of the In Vivo Behavior of Salicylic Acid by Detecting the Contrast Agent in the Kidney Upon Imaging:

In vivo CEST-MR images were acquired on a Bruker Biospec 11.7 T MR scanner. The BALB/c mice weighing 20-25 g (Charles River Laboratories Italia S.r.l., Calco Italia) were maintained under specific pathogen-free conditions in the animal facility of Johns Hopkins University. For MRI, mice were anesthetized by 0.5-2% isoflurane and placed in a 23-mm mouse coil for both transmission and receiver. Breath rate was monitored throughout in vivo MRI experiments using a respiratory probe. A 100 □L volume of a 0.1-M beta hydroxy carboxylates solution in water (pH 7) was slowly injected via a catheter into the tail vein. CEST images of one axial slice were acquired at different time-points pre- and post-injection with a temporal resolution of 100 secs. The sequence is similar as in phantom study except a saturation field strength (B1) of 7.2 uT TR/TE=5 s/15 ms, matrix size=64×48, FOV=1.7 cm×2.05 mm and slice thickness of 1.5 mm. At each time point, 2 saturation-weighted images were acquired with saturation frequency at +9.5 ppm and −9.5 ppm from water, respectively. All data were processed using home-written scripts in MATLAB (Mathworks, Waltham, Mass.). CEST contrast was quantified by $MTR_{asym}=(S_{-\Delta\omega}-S_{+\Delta\omega})/S_{-\Delta\omega}$, and the contrast map was smoothed using 2×2 median filter and overlayed on the saturation-weighted image at −9.5 ppm at the same time point. A threshold was added to the CEST contrast map by filtering the voxels with signal-noise-ratio less than 40:1. An example map displaying CEST contrast in the kidney of a mouse by injecting salicylic acid is shown below.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

R. J. Abraham and M. Mobli, *Magnetic Resonance in Chemistry* 2007, 45, 865-877.

S. Aime, D. Delli Castelli and E. Terreno, *Angewandte Chemie* 2002, 114, 4510-4512.

S. Aime, C. Carrera, D. D. Castelli, S. G. Crich, E. Terreno, Angew. Chem. Int. Ed. 2005, 44, 1813-1815.

S. Aime, D. D. Castelli, E. Terreno, Angew. Chem. Int. Ed. 2005, 44, 5513-5515.

S. Aime, L. Calabi, L. Biondi, M. De Miranda, S. Ghelli, L. Paleari, C. Rebaudengo, E. Terreno, Magn. Reson. Med. 2005, 53, 830-834.

R. D. Airan, A. Bar-Shir, G. S. Liu, G. Pelted, M. T. McMahon, P. C. M. van Zijl, J. W. M. Butte, A. A. Gilad, Magn. Reson. Med. 2012, 68, 1919-1923; c) A. Salhotra, B. Lal, J. Laterra, P. Z. Sun, P. C. M. van Zijl, J. Y. Zhou, NMR Biomed 2008, 21, 489-497.

M. M. Ali, M. P. I. Bhuiyan, B. Janic, N. R. S. Varma, T. Mikkelsen, J. R. Ewing, R. A. Knight, M. D. Pagel, A. S. Arbab, Nanomedicine 2012, 7, 1827-1837.

A. Bar-Shir, G. S. Liu, Y. J. Liang, N. N. Yadav, M. T. McMahon, P. Walczak, S. Nimmagadda, M. G. Pomper, K. A. Tallman, M. M. Greenberg, P. C. M. van Zijl, J. W. M. Bulte, A. A. Gilad, J. Am. Chem. Soc. 2013, 135, 1617-1624.

C. J. Blacklock, J. R. Lawrence, D. Wiles, E. A. Malcolm, I. H. Gibson, C. J. Kelly, J. R. Paterson, J. Clin. Pathol. 2001, 54, 553-555.

B. Brzezinski and G. Zundel, *Journal of Magnetic Resonance* (1969) 1982, 48, 361-366.

K. J. Cai, M. Haris, A. Singh, F. Kogan, J. H. Greenberg, H. Hariharan, J. A. Detre, R. Reddy, Nat. Med. 2012, 18, 302-306.

P. Caravan, J. J. Ellison, T. J. McMurry and R. B. Lauffer, *Chemical Reviews* 1999, 99, 2293-2352.

P. Caravan, C. T. Farrar, L. Frullano and R. Uppal, *Contrast Media & Molecular Imaging* 2009, 4, 89-100.

D. D. Castelli, E. Terreno, D. Longo and S. Aime, *Nmr in Biomedicine* 2013, 26, 839-849.

P. Caravan, Chem. Soc. Rev. 2006, 35, 512-523.

K. W. Chan, M. T. McMahon, Y. Kato, G. Liu, J. W. Bulte, Z. M. Bhujwalla, D. Artemov and P. C. van Zijl, *Magnetic resonance in medicine: official journal of the Society of Magnetic Resonance in Medicine/Society of Magnetic Resonance in Medicine* 2012, 68, 1764-1773.

K. W. Y. Chan, G. Liu, X. Song, H. Kim, T. Yu, D. R. Arifin, A. A. Gilad, J. Hanes, P. Walczak, P. C. M. van Zijl, Nat Mater 2013, 12, 268-275.

T. Chauvin, P. Durand, M. Bernier, H. Meudal, B-T. Doan, F. Noury, B. Badet, J-C. Beloeil, E. Toth, Angew. Chem. Int. Ed. 2008, 47, 4370-4372.

L. Q. Chen, C. M. Howison, J. J. Jeffrey, I. F. Robey, P. H. Kuo and M. D. Pagel, *Magnetic Resonance in Medicine* 2013, n/a-n/a.

P. G. Cozzi, *Chemical Society Reviews* 2004, 33, 410-421; b) M. Tokunaga, J. F. Larrow, F. Kakiuchi and E. N. Jacobsen, *Science* 1997, 277, 936-938.

S. J. Dorazio, P. B. Tsitovich, K. E. Siters, J. A. Spernyak and J. R. Morrow, *Journal of the American Chemical Society* 2011, 133, 14154-14156.

S. J. Dorazio, A. O. Olatunde, J. A. Spernyak and J. R. Morrow, *Chemical Communications* 2013, 49, 10025-10027.

S. Forsén and R. A. Hoffman, *The Journal of Chemical Physics* 1963, 39, 2892.

J. I. Friedman, M. T. McMahon, J. T. Stivers, P. C. M. Van Zijl, J. Am. Chem. Soc. 2010, 132, 1813-1815.

A. A. Gilad, M. T. McMahon, P. Walczak, P. T. Winnard, Jr., V. Raman, H. W. van Laarhoven, C. M. Skoglund, J. W. Bulte and P. C. van Zijl, *Nature Biotechnology* 2007, 25, 217-219.

N. Goffeney, J. W. Bulte, J. Duyn, L. H. Bryant, Jr. and P. C. van Zijl, *Journal of the American Chemical Society* 2001, 123, 8628-8629.

V. Guivel-Scharen, T. Sinnwell, S. D. Wolff and R. S. Balaban, *Journal of Magnetic Resonance* 1998, 133, 36-45.

I. Hancu, W. T. Dixon, M. Woods, E. Vinogradov, A. D. Sherry, R. E. Lenkinski. Acta Radiol. 2010, 51, 910-923.

M. Haris, K. Cai, A. Singh, H. Hariharan and R. Reddy, *NeuroImage* 2011, 54, 2079-2085.

M. Haris, R. P. R. Nanga, A. Singh, K. Cai, F. Kogan, H. Hariharan, R. Reddy, NMR Biomed., 2012, 25, 1305-1309.

M. Haris, A. Singh, K. Cai, K. Nath, R. Crescenzi, F. Kogan, H. Hariharan, R. Reddy, J. Neurosci. Meth. 2013, 212, 87-93.

M. G. Harisinghani, J. Barentsz, P. F. Hahn, W. M. Deserno, S. Tabatabaei, C. H. van de Kaa, J. de la Rosette and R. Weissleder, *New England Journal of Medicine* 2003, 348, 2491-U2495.

T. Jin, J. Autio, T. Obata, S. G. Kim, Magn. Reson. Med. 2011, 65, 1448-1460. F. Torrealdea, S. Walker-Samuel, R. Ramasawmy, M. Rega, S. P. Johnson, V. Rajkumar, S. Richardson, M. Goncalves, D. L. Thomas, R. B. Pedley, E. Arstad, H. Parkes, M. F. Lythgoe, X. Golay, Contrast Media Mol. Imaging 2013 doi: 10.1002/cmmi.1522.

J. Keupp, I. Dimitrov, S. Langereis, O. Togao, M. Takahashi and A. D. Sherry, *Proc. Intl. Soc. Mag. Reson. Med* (Montreal, Quebec, Canada) 2011, p. 828.

M. Kim, J. Gillen, B. A. Landman, J. Zhou and P. C. van Zijl, *Magnetic resonance in medicine: official journal of the Society of Magnetic Resonance in Medicine/Society of Magnetic Resonance in Medicine* 2009, 61, 1441-1450.

F. Kogan, M. Haris, A. Singh, K. Cai, C. Debrosse, R. P. Nanga, H. Hariharan and R. Reddy, *Magnetic resonance in medicine: official journal of the Society of Magnetic Resonance in Medicine/Society of Magnetic Resonance in Medicine* 2013.

V. Kubicek, E. Toth, in Advances in Inorganic Chemistry, Vol 61 (Eds R. VanEldik, C. D. Hubbard), Elsevier Academic Press Inc, San Diego, 2009, pp. 63-129.

S. Laurent, D. Forge, M. Port, A. Roch, C. Robic, L. V. Elst and R. N. Muller, *Chemical Reviews* 2008, 108, 2064-2110.

J-S. Lee, A. K. Khitrin, R. R. Regatte, J. Chem. Phy. 2011, 134, 234504-234506.

J. S. Lee, R. R. Regatte and A. Jerschow, *Journal of Magnetic Resonance* 2012, 215, 56-63.

W. Ling, R. R. Regatte, G. Navon, A. Jerschow, Proc Natl Acad Sci USA 2008, 105, 2266-2270.

G. S. Liu, Y. J. Liang, A. Bar-Shir, K. W. Y. Chan, C. S. Galpoththawela, S. M. Bernard, T. Tse, N. N. Yadav, P. Walczak, M. T. McMahon, J. W. M. Bulte, P. C. M. van Zijl and A. A. Gilad, *Journal of the American Chemical Society* 2011, 133, 16326-16329.

G. S. Liu, M. Moake, Y. E. Har-el, C. M. Long, K. W. Y. Chan, A. Cardona, M. Jamil, P. Walczak, A. A. Gilad, G. Sgouros, P. C. M. van Zijl, J. W. M. Bulte, M. T. McMahon, Magn. Reson. Med. 2012, 67, 1106-1113.

G. S. Liu, K. W. Y. Chan, X. L. Song, J. Y. Zhang, A. A. Gilad, J. W. M. Bulte, P. C. M. van Zijl, M. T. McMahon, Magn. Reson. Med. 2013, 69, 516-523.

G. S. Liu, X. L. Song, K. W. Y. Chan and M. T. McMahon, *Nmr in Biomedicine* 2013, 26, 810-828.

J. B. Livramento, L. Helm, A. Sour, C. O'Neil, A. E. Merbach and E. Toth, *Dalton Transactions* 2008, 1195-1202.

D. L. Longo, W. Dastru, G. Digilio, J. Keupp, S. Langereis, S. Lanzardo, S. Prestigio, O. Steinbach, E. Terreno, F. Uggeri, S. Aime, Magn. Reson. Med. 2011, 65, 202-211.

T. Mani, G. Tircso, O. Togao, P. Zhao, T. C. Soesbe, M. Takahashi, A. D. Sherry, Contrast Media Mol. Imaging 2009, 4, 183-191.

M. F. McCarty, K. I. Block, Integr. Cancer Ther. 2006, 5, 252-268.

M. T. McMahon, A. A. Gilad, J. Zhou, P. Z. Sun, J. W. M. Bulte, P. C. M. van Zijl, Magn. Reson. Med. 2006, 55, 836-847.

M. T. McMahon, A. A. Gilad, M. A. DeLiso, S. D. C. Berman, J. W. M. Bulte, P. C. M. van Zijl. Magn. Reson. Med. 2008, 60, 803-812.

A. Mueller-Lutz, N. Khalil, R. S. Lanzman, G. Oeltzschner, G. Pentag, V. Jellus, B. Schmitt, G. Antoch, and H.-J. Wittsack, *Proc. Intl. Soc. Mag. Reason. Med.* (Salt Lake City, Utah) 2013, p. 4220.

A. O. Olatunde, S. J. Dorazio, J. A. Spernyak and J. R. Morrow, *Journal of the American Chemical Society* 2012, 134, 18503-18505.

J. R. Paterson, G. Baxter, J. S. Dreyer, J. M. Halket, R. Flynn, J. R. Lawrence, *J. Agr. Food Chem.* 2008, 56, 11648-11652.

R. G. Pautler, A. C. Silva and A. P. Koretsky, *Magnetic Resonance in Medicine* 1998, 40, 740-748.

T. Saesmaa and A. M. Tatterman, *Journal of Pharmaceutical and Biomedical Analysis* 1990, 8, 61-65.

R. Scheidegger, E. Vinogradov, D. C. Alsop, Magn. Reson. Med. 2011, 66, 1275-1285.

M. Schnurr, C. Witte and L. Schroder, *Physical Chemistry Chemical Physics* 2013, 15, 14178-14181.

L. Schroeder, T. Meldrum, M. Smith, T. J. Lowery, D. E. Wemmer and A. Pines, *Physical Review Letters* 2008, 100.

K. Snoussi, J. W. Bulte, M. Gueron and P. C. van Zijl, *Magn Reson Med* 2003, 49, 998-1005.

T. C. Soesbe, Y. Wu, A. D. Sherry, NMR in Biomedicine 2012 doi:10.1002/nbm.2874.

X. Song, A. A. Gilad, S. Joel, G. Liu, A. Bar-Shir, Y. Liang, M. Gorelik, J. J. Pekar, P. C. van Zijl, J. W. Bulte, M. T. McMahon, Mag. Res. Med. 2012 68, 1074-1086.

X. Song, X. Yang, S. Ray Banerjee, M. G. Pomper and M. T. McMahon, *Contrast Media & Molecular Imaging* doi: 10.1002/cmmi.1597.

E. Terreno, C. Cabella, C. Carrera, D. D. Castelli, R. Mazzon, S. Rollet, J. Stancanello, M. Visigalli, S. Aime, Angew. Chem. Int. Ed. 2007, 46, 966-968.

E. Terreno, D. D. Castelli, S. Aime, Contrast Media Mol. Imaging 2010, 5, 78-98.

R. Trokowski, J. M. Ren, F. K. Kalman and A. D. Sherry, *Angewandte Chemie-International Edition* 2005, 44, 6920-6923.

P. C. M. van Zijl, C. K. Jones, J. Ren, C. R. Malloy, A. D. Sherry, Proc. Natl. Acad. Sci. USA 2007, 104, 4359-4364.

P. C. M. van Zijl, N. N. Yadav, Magn. Reson. Med. 2011, 65, 927-948.

E. Vinogradov, H. He, A. Lubag, J. A. Balschi, A. D. Sherry, R. E. Lenkinski, Magn. Reson. Med. 2007, 58, 650-655.

S. Walter, Br. Med. J. 2000, 321.

S. Walker-Samuel, R. Ramasawmy, F. Torrealdea, M. Rega, V. Rajkumar, S. P. Johnson, S. Richardson, M. Goncalves, H. G. Parkes, E. Arstad, D. L. Thomas, R. B. Pedley, M. F. Lythgoe and X. Golay, *Nature Medicine* 2013.

K. M. Ward, A. H. Aletras, R. S. Balaban, J. Magn. Reson. 2000, 143, 79-87.

K. M. Ward and R. S. Balaban, *Magnetic resonance in medicine: official journal of the Society of Magnetic Resonance in Medicine/Society of Magnetic Resonance in Medicine* 2000, 44, 799-802.

P. M. Winter, K. Cai, J. Chen, C. R. Adair, G. E. Kiefer, P. S. Athey, P. J. Gaffney, C. E. Buff, J. D. Robertson, S. D. Caruthers, S. A. Wickline, G. M. Lanza, Magn. Reson. Med. 2006, 56, 1384-1388.

J. Xu, N. N. Yadav, A. Bar-Shir, C. K. Jones, K. W. Y. Chan, J. Zhang, P. Walczak, M. T. McMahon and P. C. M. van Zijl, *Magnetic Resonance in Medicine* 2013, n/a-n/a.

N. N. Yadav, C. K. Jones, J. D. Xu, A. Bar-Shir, A. A. Gilad, M. T. McMahon and P. C. M. van Zijl, *Magnetic Resonance in Medicine* 2012, 68, 1048-1055.

X. Yang, X. L. Song, Y. G. Li, G. S. Liu, S. R. Banerjee, M. G. Pomper and M. T. McMahon, *Angewandte Chemie-International Edition* 2013, 52, 8116-8119.

B. Yoo and M. D. Pagel, *Journal of the American Chemical Society* 2006, 128, 14032-14033.

S. Zhang, P. Winter, K. Wu and A. D. Sherry, *Journal of the American Chemical Society* 2001, 123, 1517-1518.

J. Zhou, B. Lal, D. A. Wilson, J. Laterra and P. C. van Zijl, *Magnetic resonance in medicine: official journal of the Society of Magnetic Resonance in Medicine/Society of Magnetic Resonance in Medicine* 2003, 50, 1120-1126.

Z. L. Zu, V. A. Janve, K. Li, M. D. Does, J. C. Gore and D. F. Gochberg, *Magnetic Resonance in Medicine* 2012, 68, 711-719.

Z. Zu, V. A. Janve, J. Xu, M. D. Does, J. C. Gore, D. F. Gochberg, *Magn. Reson. Med.* 2013, 69. 637-647.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method of producing a magnetic resonance (MR) image of a target, comprising:
    introducing a magnetic resonance imaging (MRI) contrast agent to the target; and
    imaging the target using a Chemical Exchange Saturation Transfer (CEST) or frequency labeled exchange (FLEX) based MRI technique to produce the MR image of the target,
    wherein the MRI contrast agent is a compound of Formula (I), or a salt or stereoisomer thereof:

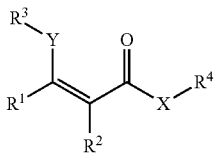

(I)

wherein:
  $R^1$ and $R^2$ are each independently H, SR, phosphorus, alkyl, amino, alkoxyl, cycloalkyl, arylalkyl, cycloalkyl-alkyl, heterocyclic, heteroaryl-alkyl, aryl, heteroaryl, —C(O)-alkyl, or —C(O)O-alkyl; or $R^1$, and $R^2$, taken together with the bonds they are attached to, form an aryl or heteroaryl group; wherein said amino, alkyl, alkoxyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted;
  when Y is O, $R^3$ is H, and when Y is $NR^5$, $R^3$ is selected from the group consisting of H, phosphorus, alkyl, —S(O)$_2$R, cycloalkyl, arylalkyl, cycloalkyl-alkyl, heterocyclic, heteroaryl-alkyl, aryl, heteroaryl, —C(O)-alkyl, or —C(O)O-alkyl, wherein said alkyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted, provided that at least one of $R^3$ and $R^5$ is H;
  $R^4$ is H, phosphorus, halogen, SR, hydroxyl, amino, alkoxyl, alkyl, cycloalkyl, arylalkyl, cycloalkyl-alkyl, heterocyclic, heteroaryl-alkyl, aryl, heteroaryl, —C(O)-alkyl, or —C(O)O-alkyl, wherein said alkyl, amino, alkoxyl, cycloalkyl, arylalkyl, cycloalkyl-alkyl, heterocyclic, heteroaryl-alkyl, aryl, heteroaryl, —C(O)-alkyl, —C(O)O-alkyl moiety is optionally substituted; and X is O, $NR^5$, alkyl, or S;

Y is O or $NR^5$; and wherein each $R^5$ is independently selected from the group consisting of H, alkyl, cycloalkyl, arylalkyl, cycloalkyl-alkyl, heterocyclic, heteroaryl-alkyl, aryl, heteroaryl, —C(O)— alkyl, or —C(O)O-alkyl, wherein said alkyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted.

2. The method of claim 1, wherein the compound of formula (I) is selected from the group consisting of:

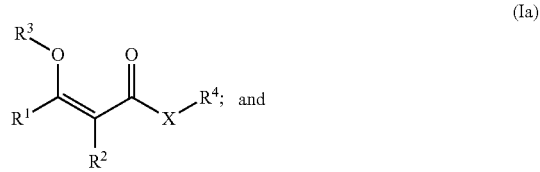

(Ia)

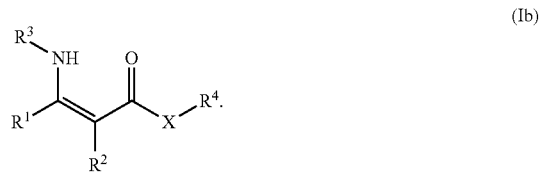

(Ib)

3. The method of claim 2, wherein the compound of formula (Ib) is selected from the group consisting of:

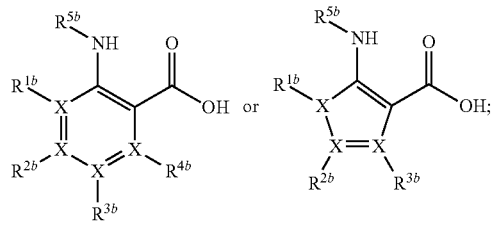

wherein:
  $R^{1b}$, $R^{1b}$ and $R^{3b}$, independently, are absent, H, amino, alkoxyl, phosphorus, halogen, alkyl, alkyl-S—, cycloalkyl, arylalkyl, cycloalkyl-alkyl, heterocyclic, heteroaryl-alkyl, hydroxyl, aryl, heteroaryl, —C(O)-alkyl, or —C(O)O-alkyl, wherein said alkyl, amino, alkoxyl, alkyl-S—, cycloalkyl, arylalkyl, cycloalkyl-alkyl, heterocyclic, heteroaryl-alkyl, aryl, heteroaryl, —C(O)— alkyl, or —C(O)O-alkyl moiety is optionally substituted;
  $R^{4b}$ is H, phosphorus, halogen, amino, alkoxyl, alkyl, alkyl-S—, cycloalkyl, arylalkyl, cycloalkyl-alkyl, heterocyclic, heteroaryl-alkyl, hydroxyl, aryl, heteroaryl, —C(O)-alkyl, or —C(O)O-alkyl, wherein said alkyl, amino, alkoxyl, alkyl-S—, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted;
  $R^{5b}$ is H, —S(O)$_2$—$R^{6b}$, alkyl, alkyl, cycloalkyl, arylalkyl, cycloalkyl-alkyl, heterocyclic, heteroaryl-alkyl, aryl, heteroaryl, —C(O)-alkyl, or —C(O)O-alkyl, wherein said alkyl, cycloalkyl, arylalkyl, cycloalkyl-alkyl, heterocyclic, heteroaryl-alkyl, aryl, heteroaryl, —C(O)-alkyl, or —C(O)O-alkyl moiety is optionally substituted;

$R^{6b}$ is H, amino, halogen, alkyl, cycloalkyl, arylalkyl, cycloalkyl-alkyl, heterocyclic, heteroaryl-alkyl, aryl, heteroaryl, —C(O)-alkyl, or —C(O)O-alkyl, wherein said amino, alkyl, cycloalkyl, arylalkyl, cycloalkyl-alkyl, heterocyclic, heteroaryl-alkyl, aryl, heteroaryl, —C(O)— alkyl, or —C(O)O-alkyl moiety is optionally substituted;

each X is independently C, NR, O, or S; and

R is H, alkyl, cycloalkyl, arylalkyl, cycloalkyl-alkyl, heterocyclic, heteroaryl-alkyl, aryl, heteroaryl, or —C(O)-alkyl, wherein said alkyl, cycloalkyl, arylalkyl, cycloalkyl-alkyl, heterocyclic, heteroaryl-alkyl, aryl, heteroaryl, or —C(O)-alkyl moiety is optionally substituted.

4. The method of claim 2, wherein the compound of formula (Ia) or (Ib) is selected from the group consisting of:

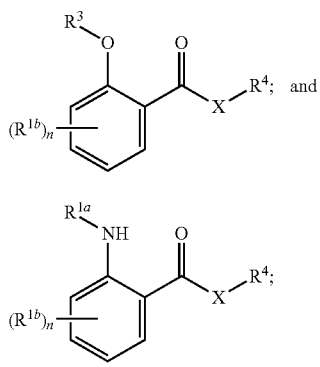

wherein:

each n is independently an integer selected from the group consisting of 0, 1, 2, 3, and 4;

each $R^{1b}$ is independently selected from the group consisting of hydrogen, substituted or unsubstituted alkyl, alkoxyl, hydroxyl, hydroxyalkyl, carboxyl, acyl, carbonyl, carbamoyl, alkylcarbamoyl, halogen, amino, nitro, nitrile, amide, haloalkyl, aryl, cycloalkyl, aralkyloxyl, and —SO₃H.

5. The method of claim 1, wherein the target is selected from the group consisting of a cell, a biological tissue, an organ, a tumor, a ligand, a biomarker, a therapeutically active agent, a metal ion, a chemotherapeutic, an antigen, a nanoparticle, a receptor, and a cation.

6. The method of claim 1, further comprising measuring a chemical shift change of exchangeable protons in said MRI contrast agent.

7. The method of claim 1, wherein the target is imaged using CEST MRI.

8. The method of claim 1, wherein the target is imaged using FLEX MRI.

9. The method of claim 1, further comprising diagnosing, based on the MR image of the target, a disease or disorder in a subject.

10. The method of claim 1, further comprising monitoring, based on the MR image of the target, progression or regression of a disease disorder in a subject.

11. The method of claim 9, wherein the disease or disorder is selected from the group consisting of infectious diseases, neoplasms, endocrine, nutritional, and metabolic diseases, diseases of the blood and blood-forming organs, inflammatory diseases, immune diseases, including autoimmune diseases, diseases of the nervous system, diseases of the circulatory system, diseases of the respiratory system, diseases of the digestive system, diseases of the skin, diseases of the musculoskeletal system.

12. The method of claim 11, wherein the disease or disorder is selected from the group consisting of cancer, diabetes and epilepsy.

13. The method of claim 1, wherein the MR imaging is performed in combination with positron emission tomography (PET).

* * * * *